United States Patent
Landau et al.

(10) Patent No.: US 12,037,619 B2
(45) Date of Patent: Jul. 16, 2024

(54) ANGIOTENSIN-CONVERTING ENZYME 2 (ACE2) IMMUNOADHESIN MICROBODY

(71) Applicant: New York University, New York, NY (US)

(72) Inventors: Nathaniel R. Landau, New York, NY (US); Takuya Tada, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 305 days.

(21) Appl. No.: 17/405,104

(22) Filed: Aug. 18, 2021

(65) Prior Publication Data

US 2022/0056429 A1 Feb. 24, 2022

Related U.S. Application Data

(60) Provisional application No. 63/067,304, filed on Aug. 18, 2020.

(51) Int. Cl.
C12N 9/48 (2006.01)
A61K 38/48 (2006.01)
A61P 31/14 (2006.01)

(52) U.S. Cl.
CPC .......... *C12N 9/485* (2013.01); *A61K 38/4813* (2013.01); *A61P 31/14* (2018.01); *C12Y 304/17023* (2013.01); *C07K 2319/21* (2013.01); *C07K 2319/30* (2013.01)

(58) Field of Classification Search
None
See application file for complete search history.

(56) References Cited

FOREIGN PATENT DOCUMENTS

WO  WO-2021217120 A2 * 10/2021 ............. A61K 38/00

* cited by examiner

*Primary Examiner* — Brad Duffy
(74) *Attorney, Agent, or Firm* — Hodgson Russ LLP

(57) ABSTRACT

Provided are polypeptides comprising an enzymatically inactive angiotensin-converting enzyme 2 (ACE2) ectodomain, a segment of an immunoglobulin Fc and optionally a purification tag. A cDNA or an expression vector encoding the polypeptide along with a method of culturing cells comprising the expression vector is also provided. The disclosure also provides a method for prophylaxis or therapy for a Coronavirus infection by administering the polypeptide to an individual in need thereof.

5 Claims, 36 Drawing Sheets

Specification includes a Sequence Listing.

A

B

E

A

B

A

B

B (continued)

| | IC50 (ng/mL) | | | | | | |
|---|---|---|---|---|---|---|---|
| | D614G | B.1.1.7 | B.1.351 | B.1.1.248 | E484K | NY1(E484K) | NY2(S477N) |
| ACE2 microbody | 137.7 | 28.73 | 41.6 | 34.3 | 149.7 | 102.9 | 92.9 |
| ACE2.v2.4 microbody | 25.8 | 14 | 17.1 | 17.5 | 26.1 | 26.4 | 25.2 |
| sACE2 | 834.9 | 312.2 | 265.9 | 260.1 | 771.9 | 951.6 | 1094 |

Figure 10 (continued)

|  | IC50 (nM) | | | | |
|---|---|---|---|---|---|
|  | D614G | B.1.1.7 | B.1.351 | B.1.617.1 | B.1.617.2 |
| ACE2.v2.4 | 0.21 | 0.13 | 0.15 | 0.05 | 0.03 |
| REGN10933 | 0.046 | 0.05 | 4.28 | 0.21 | 0.60 |
| REGN10987 | 0.38 | 0.34 | 0.57 | 0.19 | 0.31 |
| REGN COV2 | 0.05 | 0.04 | 0.14 | 0.16 | 0.15 |
| REGN10933+ACE2.v2.4 | 0.04 | 0.02 | 0.39 | 0.02 | 0.06 |
| REGN10987+ACE2.v2.4 | 0.21 | 0.19 | 0.57 | 0.03 | 0.04 |
| REGN COV2+ACE2.v2.4 | 0.003 | 0.008 | 0.15 | 0.002 | 0.005 |

His tag(8 amino acid): Green

HHHHHHHH (SEQ ID NO:4)

ACE2.H345A-microbody (879 amino acid)
Expected protein size 105kDa

MSSSWLLLSLVAVTAAQSTIEQAKTFLDKFNHEAEDLFYQSSLASWNYNTNITEENVQNMNNAGDKWSAFLKEQSTLAQMYPLQEIQNLTVKLQLQALQQNGSS
VLSEDKSKRLNTILNTMSTIYSTGKVCNPDNPQECLLLEPGLNEIMANSLDYNERLWAWESWRSEVGKQLRPLYEEYVVLKNEMARANHYEDYGDYWRGDYEV
NGVDGYDYSRGQLIEDVEHTFEEIKPLYEHLHAYVRAKLMNAYPSYISPIGCLPAHLLGDMWGRFWTNLYSLTVPFGQKPNIDVTDAMVDQAWDAQRIFKEAEKFFVSV
GLPNMTQGFWENSMLTDPGNVQKAVCHPTAWDLGKGDFRILMCTKVTMDDFLTAHHEMGHIQYDMAYAAQPFLLRNGANEGFHEAVGEIMSLSAATPKHLKSIGLL
SPDFQEDNETEINFLLKQALTIVGTLPFTYMLEKWRWMVFKGEIPKDQWMKKWWEMKREIVGVVEPVPHDETYCDPASLFHVSNDYSFIRYYTRTLYQFQFQEALC
QAAKHEGPLHKCDISNSTEAGQKLFNMLRLGKSEPWTLALENVVGAKNMNVRPLLNYFEPLFTWLKDQNKNSFVGWSTDWSPYADQSIKVRISLKSALGDKAYEWN
DNEMYLFRSSVAYAMRQYFLKVKNQMILFGEEDVRVANLKPRISFNFFVTAPKNVSDIIPRTEVEKAIRMSRSRINDAFRINDAFRLNDAFRLLGLQPTLGPPNQPPVSIW
KSCDKRTHTCPGGSGSGGSGGSGQPREPQVYTLPPSREEMTKNQVSLTCLVKGFYPSDIAVEWESNGQPENNYKTTPPVLDSDGSFFLYSKLTVDKSRWQQGNVFS
CSVMHEALHNHYTQKSLSLSPGKHHHHHHHH (SEQ ID NO:5)

Mutation in ACE2 (345aa)

Figure 17 (continued)

ANGIOTENSIN-CONVERTING ENZYME 2 (ACE2) IMMUNOADHESIN MICROBODY

CROSS-REFERENCE TO RELATED APPLICATIONS

This application claims priority to U.S. provisional application No. 63/067,304, filed on Aug. 18, 2020, the disclosure of which is incorporated herein by reference.

STATEMENT REGARDING FEDERALLY SPONSORED RESEARCH

This invention was made with government support under grant no. DP1 DA04611 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 16, 2021, is named 058636_00367_ST25.txt and is 107,000 bytes in size.

FIELD

The present disclosure relates to compositions and methods for prophylaxis and/or therapy of COVID-19. The compositions comprise a soluble, enzymatically inactive ACE2 receptor as a component of a fusion protein that also comprises a segment of an Fc region of an antibody.

BACKGROUND

As the novel severe acute respiratory syndrome coronavirus 2 (SARS-CoV-2) continues to spread worldwide, there is an urgent need for preventative vaccine and improved therapeutics for treatment of COVID-19. The development of therapeutic agents that block specific steps of the coronavirus replication cycle will be highly valuable. Coronavirus replication includes attachment, uncoating, replication, translation, assembly, and release, all of which are potential drug targets. Virus entry is particularly advantageous because as the first step in virus replication, it spares target cells from becoming infected and because drugs that block entry do not need to be cell permeable as the targets are externally exposed. In SARS-CoV-2 entry, the virus attaches to the target cell through the interaction of the spike glycoprotein (S) with its receptor, the angiotensin-converting enzyme 2 (ACE2) (Li, Moore et al. 2003, Li, Li et al. 2005, Li 2015), a plasma membrane protein with catalytic function that converts angiotensin I (Ang I) into the angiotensin-(1-7) [Ang-(1-7)] to promote sodium transport that regulates cardiac function and blood pressure (Riordan 2003, Kuba, Imai et al. 2010, Tikellis and Thomas 2012).

ACE2 binding triggers S protein-mediated fusion of the viral envelope with the cell plasma membrane or intracellular endosomal membranes. The S protein is synthesized as a single polypeptide that is cleaved by cellular proteases such as furin into S1 and S2 subunits in the endoplasmic reticulum. The S1 subunit contains the receptor binding domain (RBD) which binds to ACE2 while S2 mediates virus-cell fusion (Li, Choe et al. 2006, Belouzard, Millet et al. 2012, Heald-Sargent and Gallagher 2012, Fehr and Perlman 2015, Shang, Wan et al. 2020). Cells that express ACE2 are potential targets of the virus. These include cells in the lungs, arteries, heart, kidney, and intestines (Harmer, Gilbert et al. 2002, Ksiazek, Erdman et al. 2003, Leung, To et al. 2003).

The use of soluble receptors to prevent virus entry by competitively binding to viral envelope glycoproteins was first explored for HIV-1 with soluble CD4. In early studies, a soluble form of CD4 deleted for the transmembrane and cytoplasmic domains was found to block virus entry in vitro (Daar, Li et al. 1990, Orloff, Kennedy et al. 1993, Sullivan, Sun et al. 1998, Schenten, Marcon et al. 1999, Haim, Si et al. 2009). Fusion of the protein to an immunoglobulin Fc region, termed an "immunoadhesin", increased the avidity for gp120 by dimerizing the protein and secondly acted to increase the half-life of the protein in vivo. An enhanced soluble CD4-Ig containing a peptide derived from the HIV-1 coreceptor CCR5 was found to potently block infection and to protect rhesus macaques from infection (Chiang, Gardner et al. 2012). The soluble receptor approach to blocking virus entry has been recently applied to SARS-CoV-2 through the use of recombinant human soluble ACE2 protein (hrsACE2) (Kuba, Imai et al. 2005, Wysocki, Ye et al. 2010, Monteil, Kwon et al. 2020) or hrsACE2-IgG which encodes soluble ACE2 and the Fc region of the human immunoglobulin G (IgG) (Case, Rothlauf et al. 2020, Lei, Qian et al. 2020) which were shown to inhibit of SARS-CoV and SARS-CoV-2 entry in a mouse model. In phase 1 and phase 2 clinical trials (Haschke, Schuster et al. 2013, Khan, Benthin et al. 2017), the protein showed partial antiviral activity but short half-life. Addition of the Fc region increased the half-life of the protein in vivo. A potential concern with the addition of the Ig Fc region is the possibility of enhancement, similar to what occurs with antibody-dependent enhancement in which anti-spike protein antibody attaches to Fc receptors on immune cells, facilitating infection rather than preventing it (Eroshenko, Gill et al. 2020). Thus, there is an ongoing and unmet need for improved compositions and methods for therapy of COVID-19. The present disclosure is pertinent to this and other needs.

SUMMARY

The present disclosure provides compositions and methods for prophylaxis and therapy for Coronavirus infections. In an embodiment, a fusion protein that is used in the compositions and methods is provided. In an embodiment, the fusion protein comprises a contiguous polypeptide comprising an enzymatically inactive angiotensin-converting enzyme 2 (ACE2) ectodomain without an intact ACE2 transmembrane domain or an intact cytoplasmic tail. The polypeptide further comprises a segment of an immunoglobulin Fc that is not an intact Fc region. The polypeptide may also comprise a purification tag, which may be positioned at the C-terminus of the polypeptide.

In embodiments, the polypeptide is enzymatically inactive due to a mutation of an amino acid in the ACE2 catalytic active site. In one example, the mutation is at position 345 of SEQ ID NO:2 such that the amino acid at said position is not histidine. In an embodiment, the amino acid at position 345 is changed to an alanine.

In an embodiment, the segment of the immunoglobulin Fc that is not an intact Fc region comprises a microbody. The microbody may further comprise an Fc IgG-CH3 segment.

The disclosure also provides pharmaceutical formulations comprising the described polypeptide. In an embodiment, the polypeptide comprises or consists of the sequence of SEQ ID NO:5.

The disclosure also provides a cDNA or an expression vector encoding the polypeptide. The disclosure further provides a method of culturing cells comprising the cDNA or expression vector encoding the polypeptide such that the polypeptide is expressed, and separating the expressed polypeptide from the cells.

In another aspect, the disclosure provides a method for prophylaxis and/or therapy for a Coronavirus infection. The method comprises comprising introducing into an individual in need thereof the polypeptide, or a pharmaceutical formulation comprising the polypeptide. In embodiments, the individual in need of therapy is a human and is infected with a SARS-CoV-2 infection, and/or has been diagnosed with COVID-19. In embodiments, the disclosure provides a synergistic anti-viral effect by administering to an individual a combination of the described polypeptide and one or more additional anti-viral agents, such as anti-SARS-CoV-2 targeted antibodies.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

Figure 5:
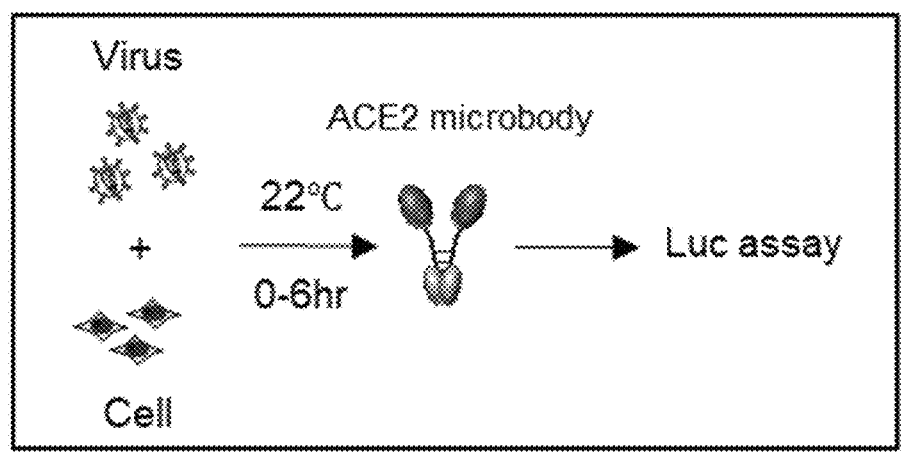
Figure 5:
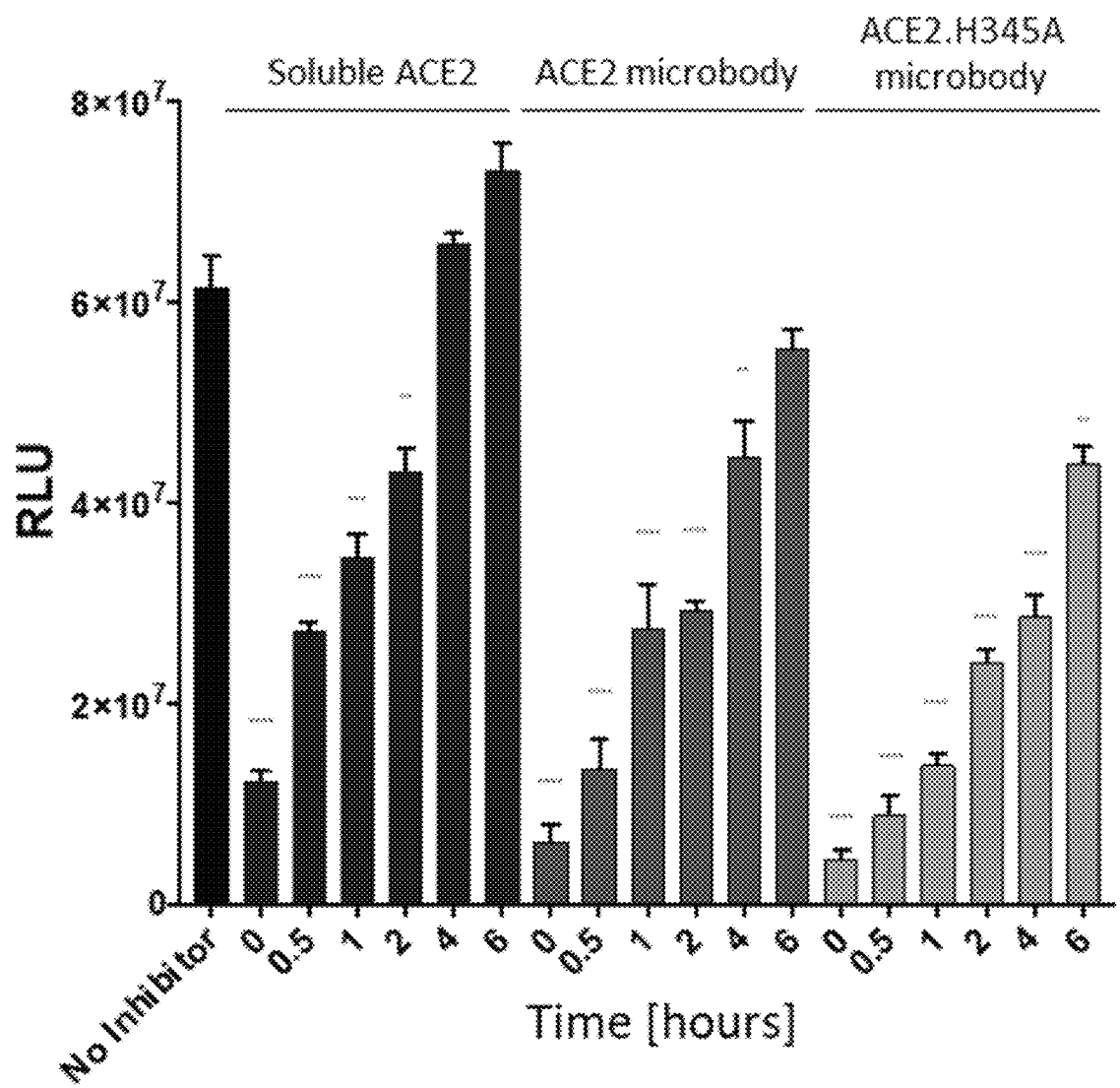
Figure 5:
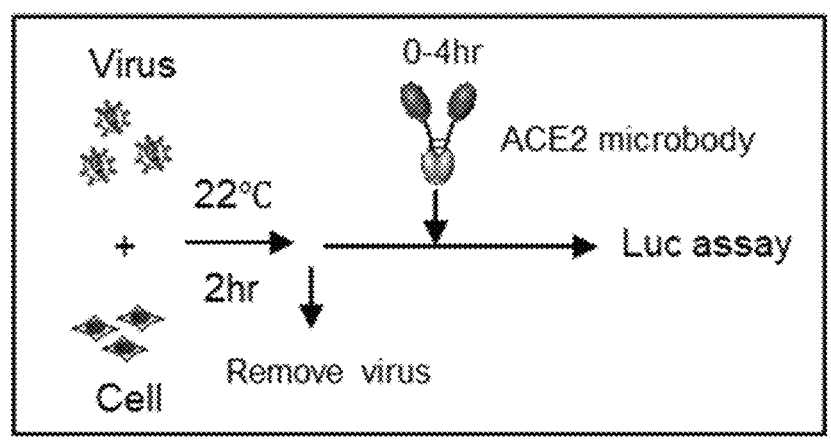
Figure 5:
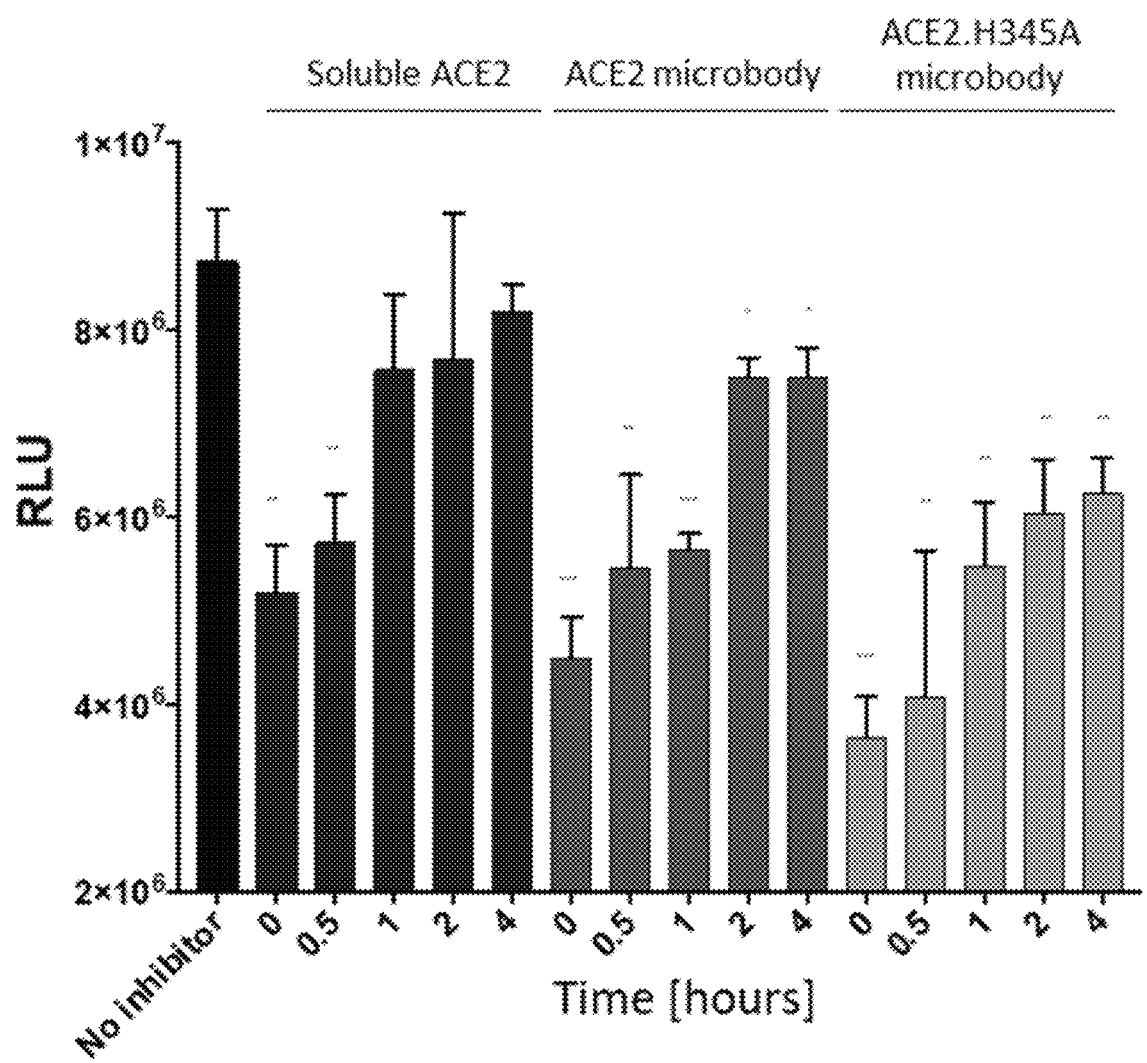

FIG. 5. ACE2 microbody can act post-virus:cell binding. The kinetics of ACE2 microbody inhibition were analyzed in an escape from inhibition escape assay. (A) The experimental scheme is diagrammed. SARS-CoV-2 Δ19.S-pseudotyped virus was added to ACE2.293T cells. Soluble ACE2 proteins were added immediately or at time points up to 6 hours later. Luciferase activity was measured 2 days post-infection. (B) As diagrammed, virus was bound to target cells for 2 hours at 22° C. and unbound virus was then removed. Soluble ACE2 proteins were added as in (A). The data are displayed as the mean±SD and statistical significance determined by student-t tests.

Figure 6:
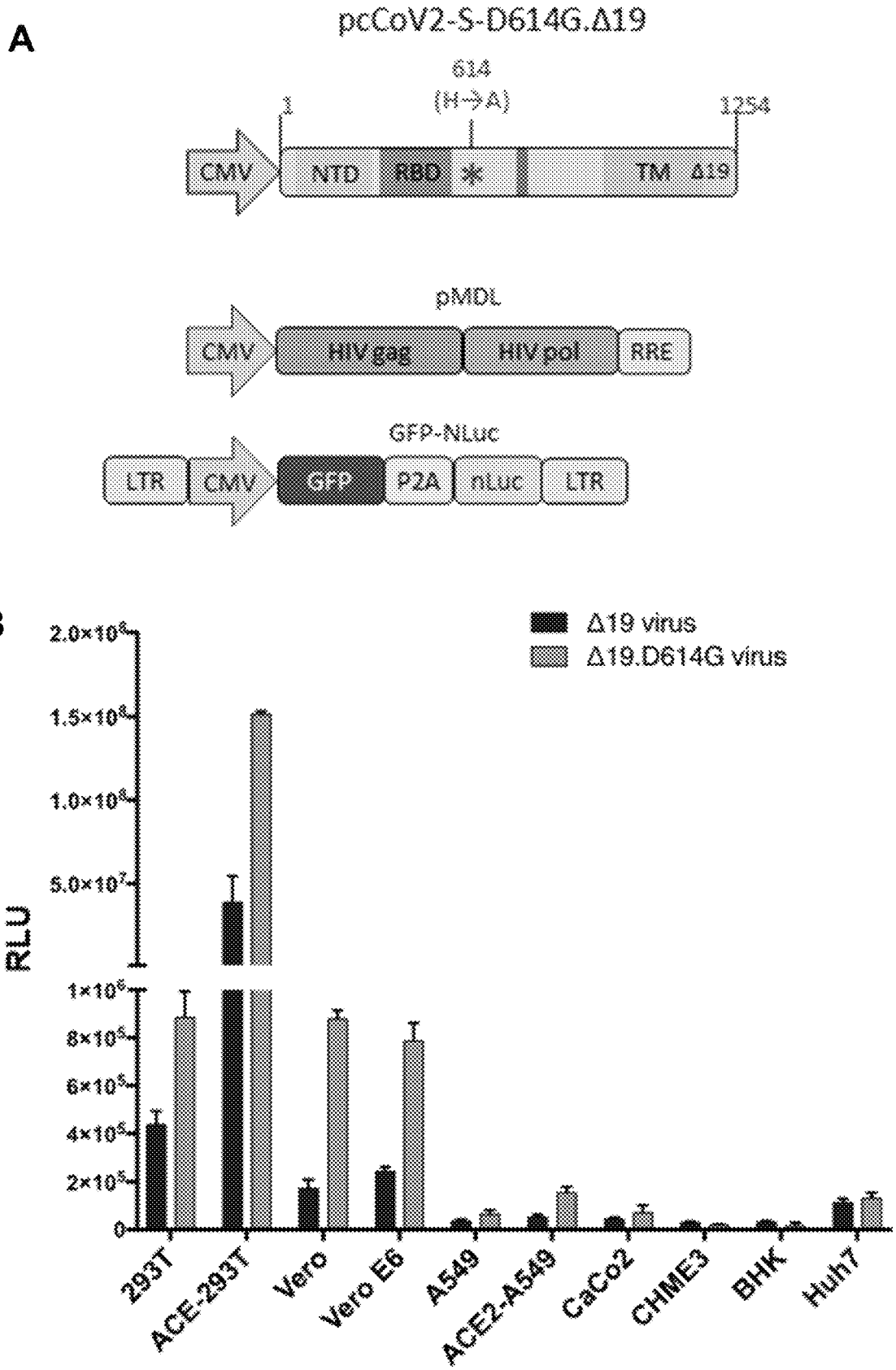
Figure 6:
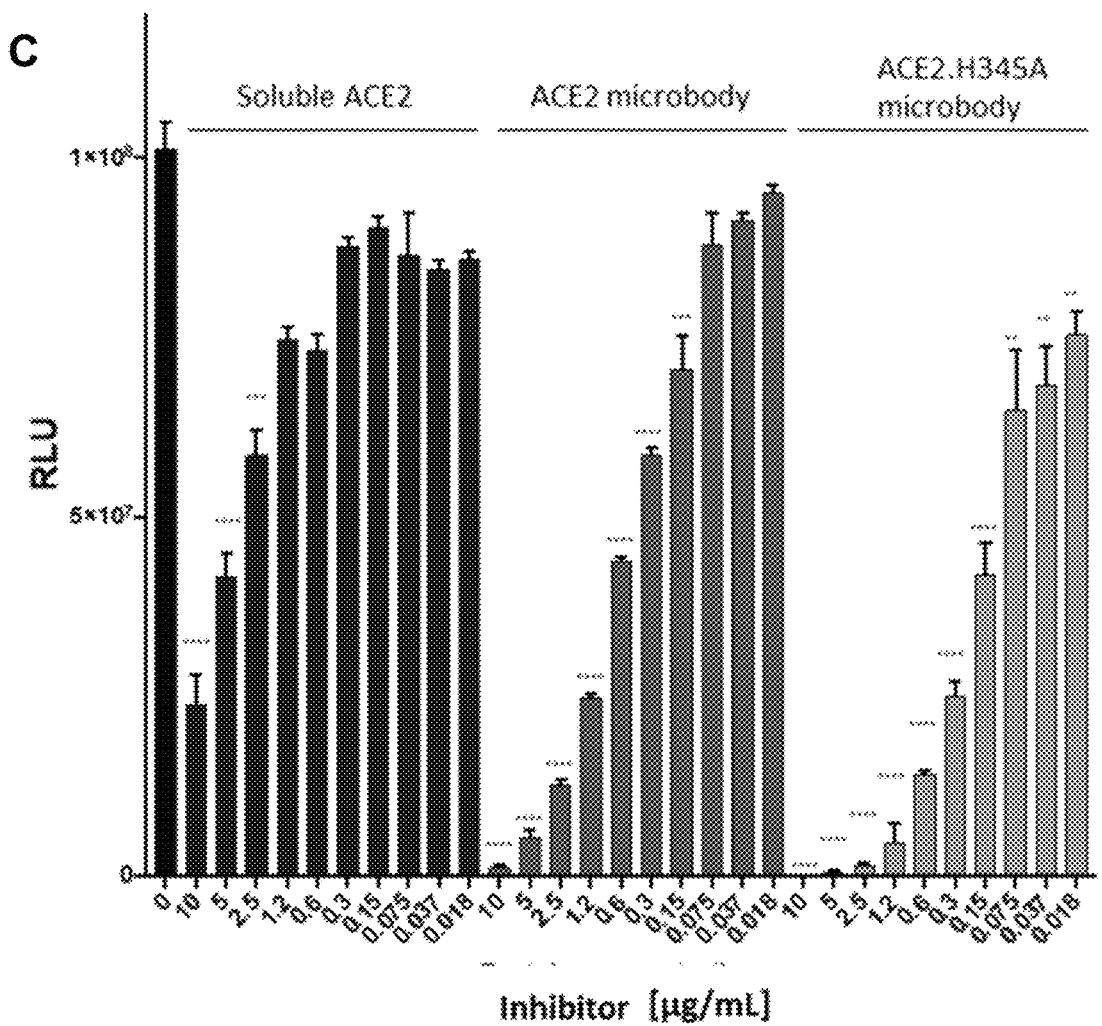
Figure 6:
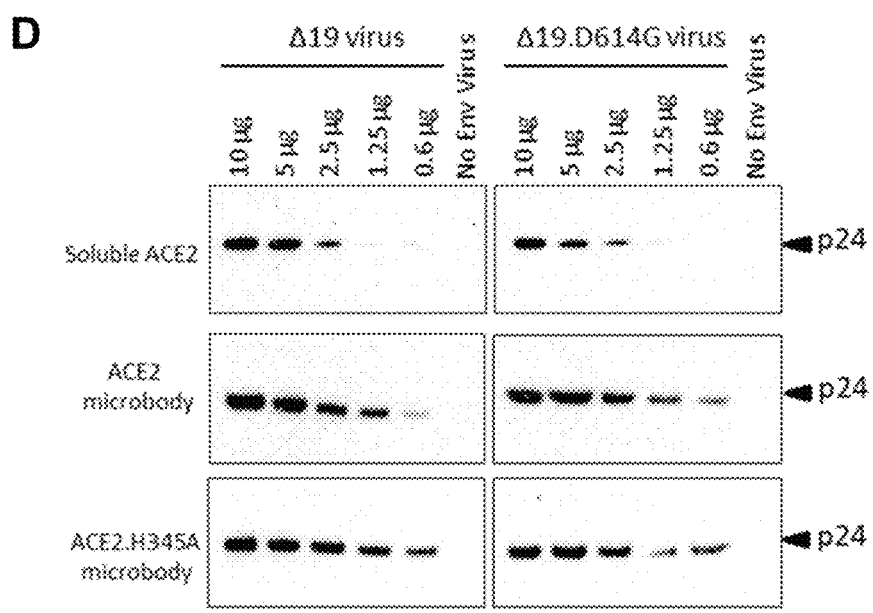

FIG. 6. ACE2 microbody blocks entry of the D614G variant S protein pseudotyped virus infection. (A) The domain structure of the SARS-CoV-2 D614G Δ19 S expression vector is diagrammed. Red star indicates the D614G mutation in the S protein. (B) A panel of cell-lines was infected with equivalent amounts of wild-type and D614G Δ19 S protein pseudotyped virus. (C) Serially diluted ACE2 and ACE2 microbody proteins were mixed with D614G Δ19 S protein pseudotyped virus and added to target cells. Luciferase activity was measured 2 days post-infection. The data are shown as the mean of triplicates±SD. The statistical significance of the data was calculated with the student-t test. (D) Ni-NTA agarose beads were coated with serially diluted soluble ACE2 and ACE2 microbody proteins. Wild-type and Δ19 S protein pseudotyped virions were added and allowed to bind. Unbound virions were removed after 30 min and the bound virions were detected by immunoblot analysis with anti-p24 antibody.

Figure 7:
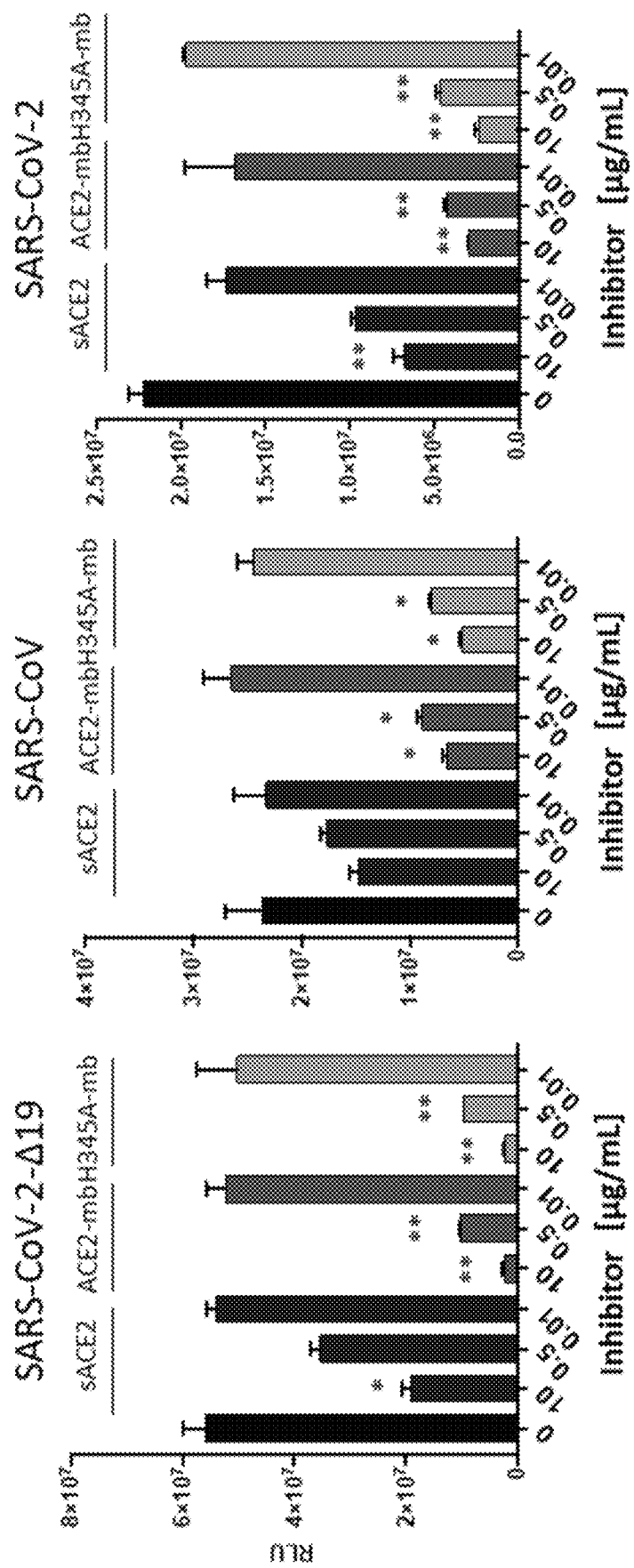
Figure 7:
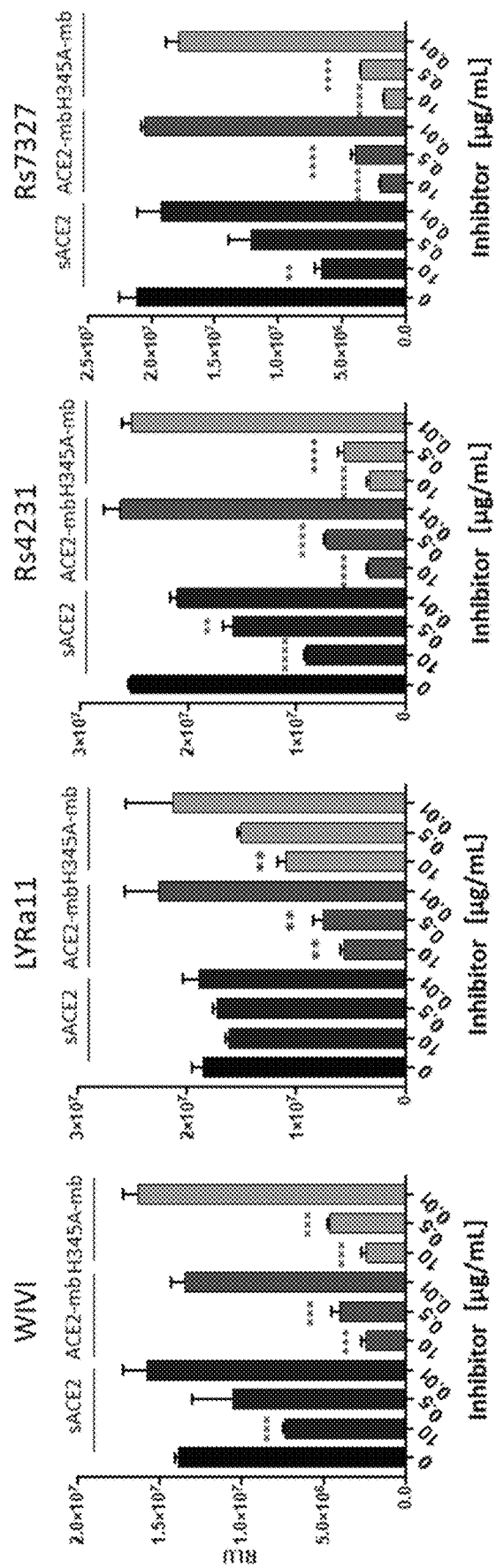
Figure 7:
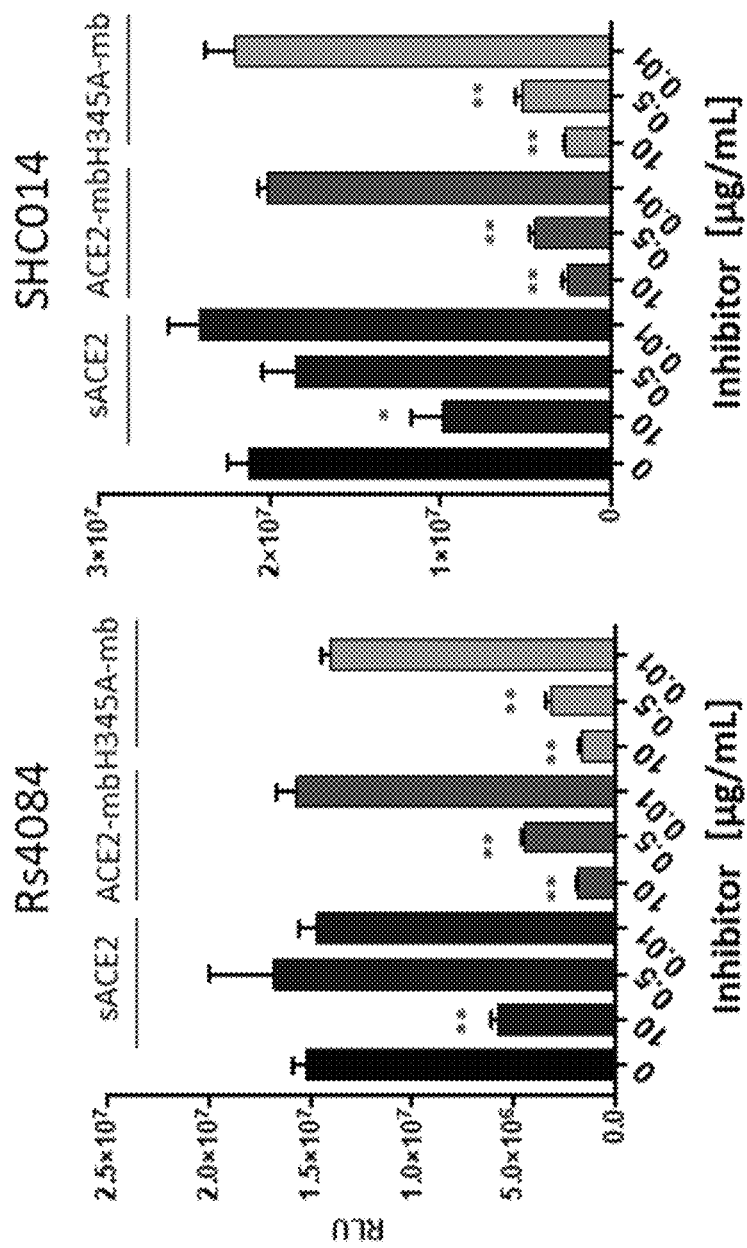

FIG. 7. ACE2 microbody is effective against ACE2-using β coronavirus S proteins. Lentiviral virions pseudotyped by β coronavirus lineage 2 S proteins were treated with serially diluted soluble ACE2 proteins and then used to infect ACE2.293T cells. The identity of the virus from which the S protein RBD is derived is indicated above each histogram. Luciferase activity was measured after 2 days. The data are displayed as the mean±SD and significance is determined by student-t tests.

Figure 8:
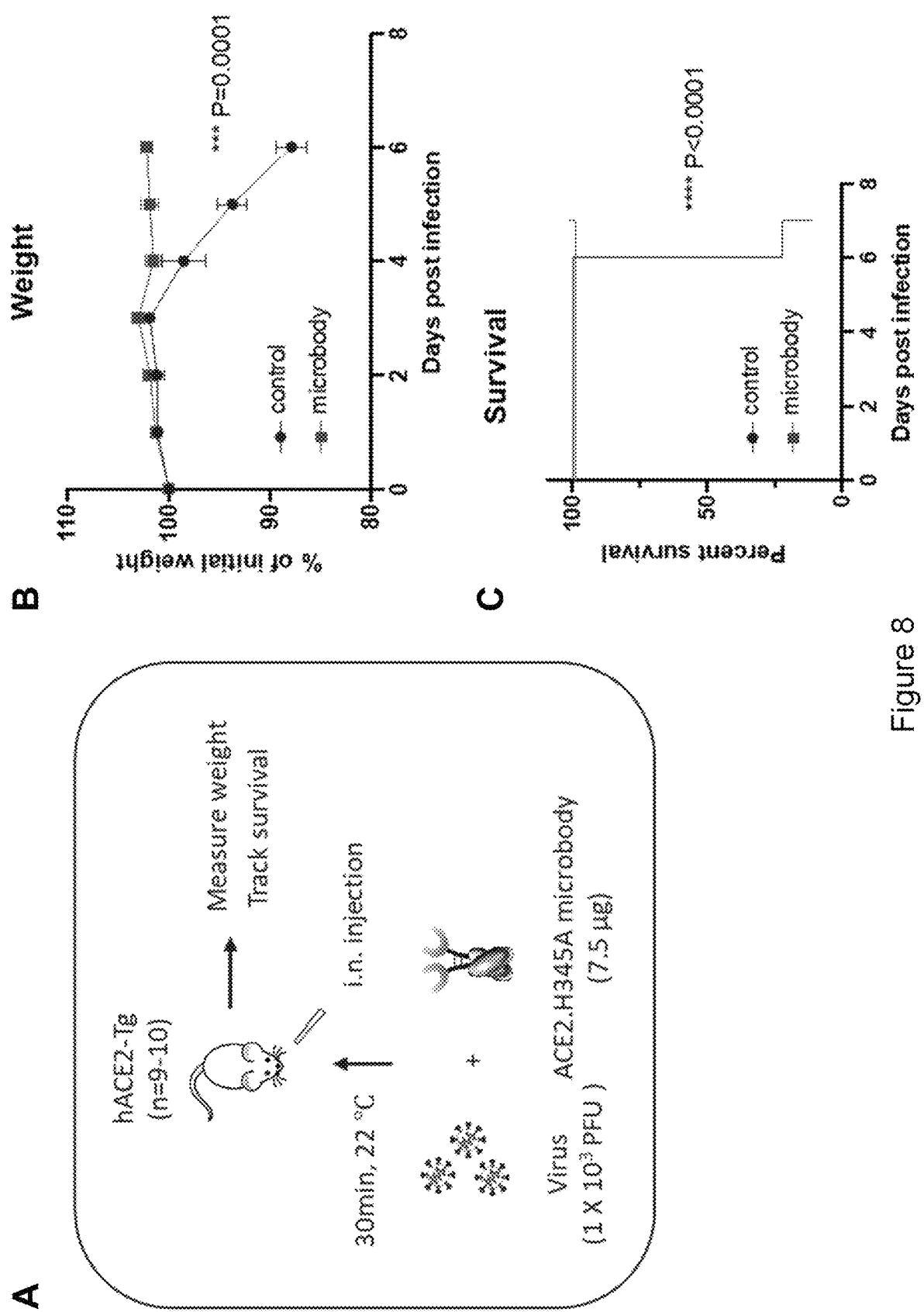

FIG. 8. ACE2.H345A microbody protects K18-hACE2 transgenic mice from SARS-CoV-2. ACE2.H345A microbody (7.5 μg) or control buffer was incubated for 30 minutes with viral inoculum (1×10³ PFU SARS-CoV-2). The virus was administered intranasally (i.n.) to K18h-ACE2 littermates (control n=9 and microbody n=10). (A) Cartoon related to (B) and (C). The mice were then monitored for weight loss (B) and survival (C). Data are pooled from two independent experiments. Weight loss was analyzed by a mixed-effects model. Survival was analyzed by a Logrank (Mantel-Cox) test. ****P<0.0001.

Figure 9:
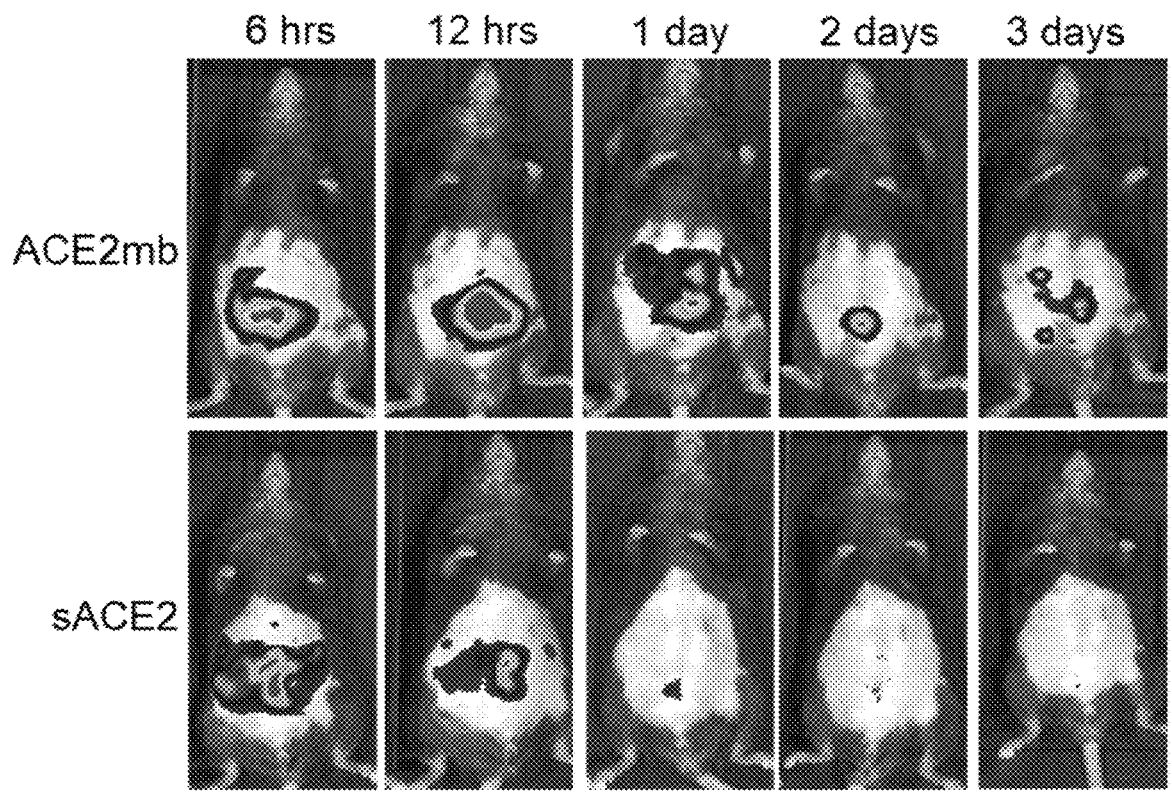
Figure 9:
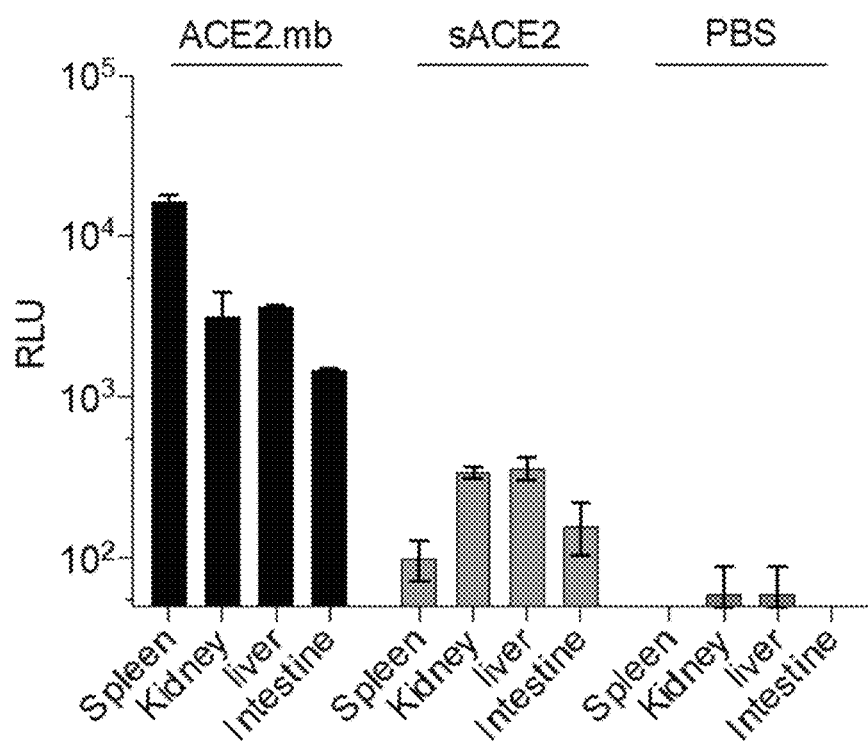

FIG. 9. ACE2 microbody has an extended in vivo half-life. (A) 5 μg/g ACE2 microbody-NLuc or sACE2 protein was injected into mice intraperitoneal (IP). The proteins were visualized in live mice 6, 12, 24, 48, 72 hours post-injection on an IVIS machine. (B) 3 days post-injection, the mice were sacrificed and nano-luciferase activity in spleen, kidney, liver and intestine was measured by enzymatic assay.

Figure 10:
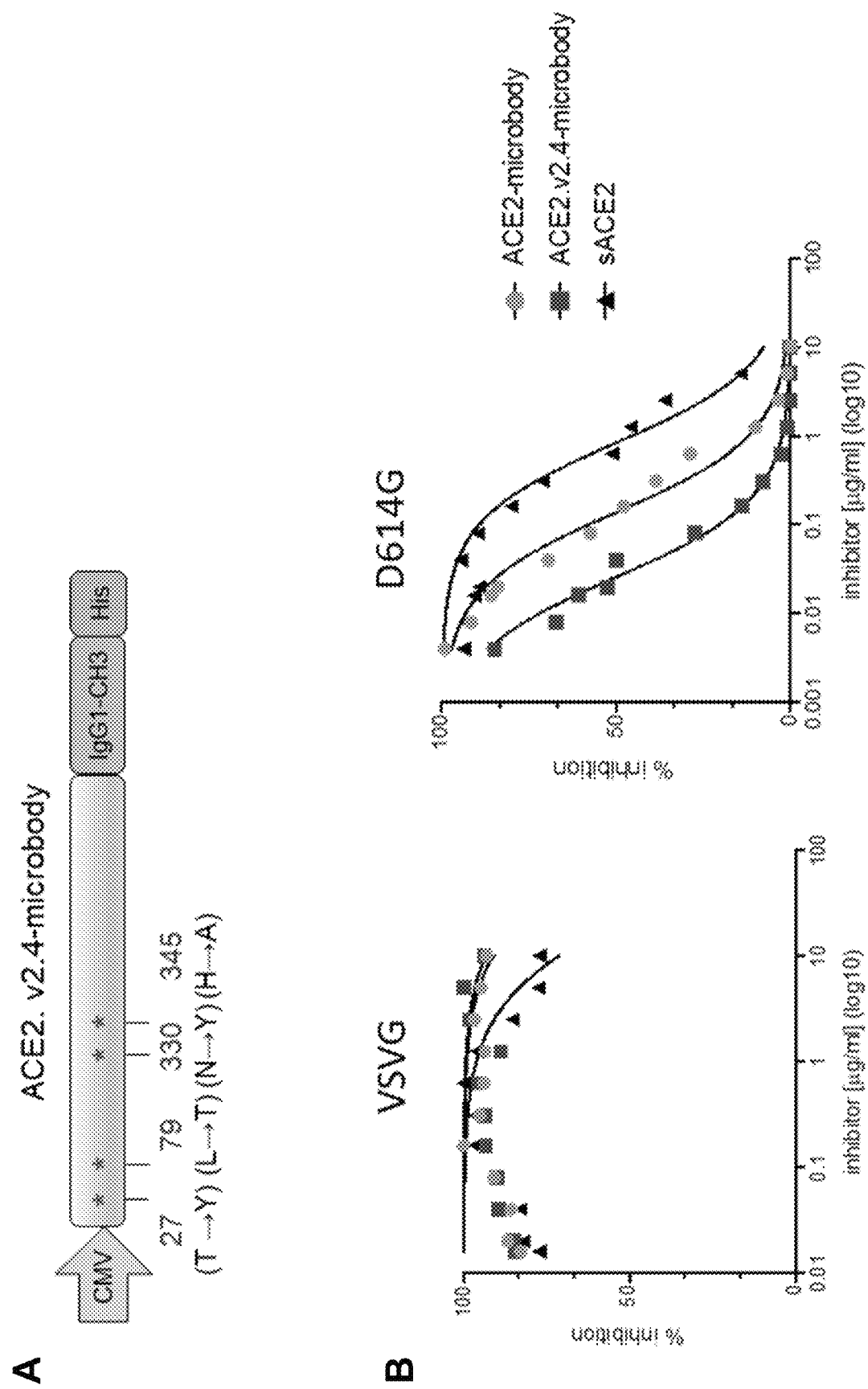
Figure 10:
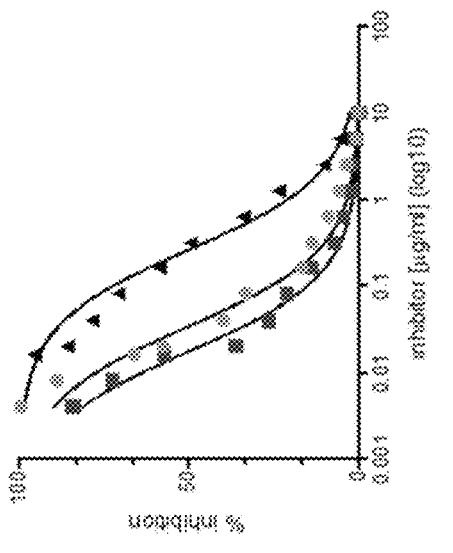
Figure 10:
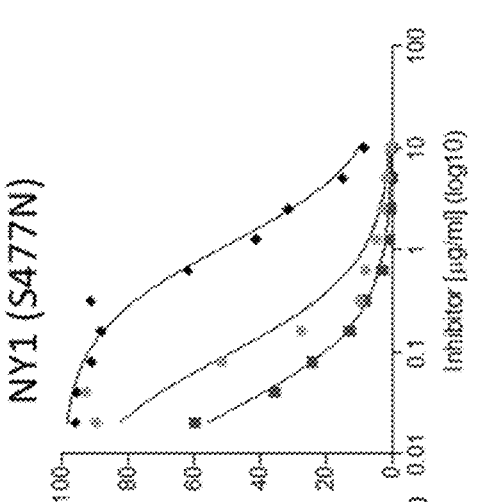
Figure 10:
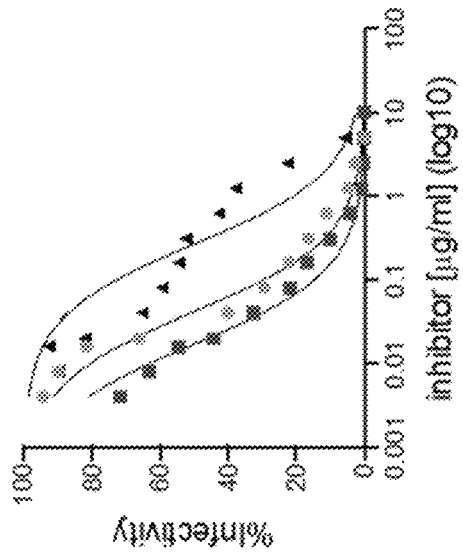
Figure 10:
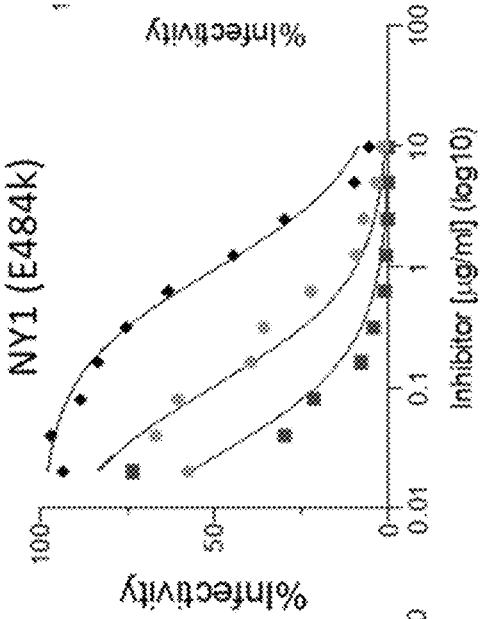
Figure 10:
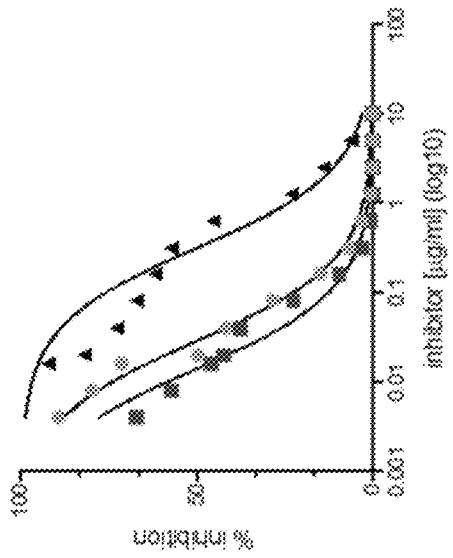
Figure 10:
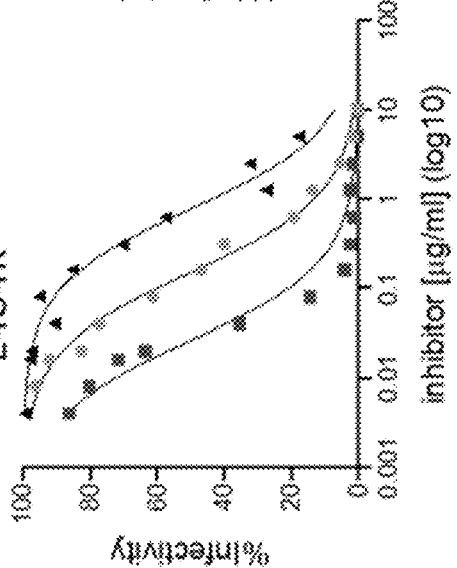

FIG. 10. ACE2.v2.4 microbody potently blocks viruses with the SARS-CoV-2 variant spike proteins. (A) The mutations in the ACE2.v2.4 microbody are shown. (B) Serially diluted soluble ACE2, ACE2 and ACE2.v2.4 microbody proteins were incubated for 30 minutes with SARS-CoV-2 variant pseudotyped viruses (B.1.1.7, B.1.351, B.1.1.248, NY1 (E484K), NY1 (S477N)) and then added to ACE2.293T cells. Luciferase activity was measured 2 days post-infection and IC50 (ng/ml) was calculated (table).

Figure 11:
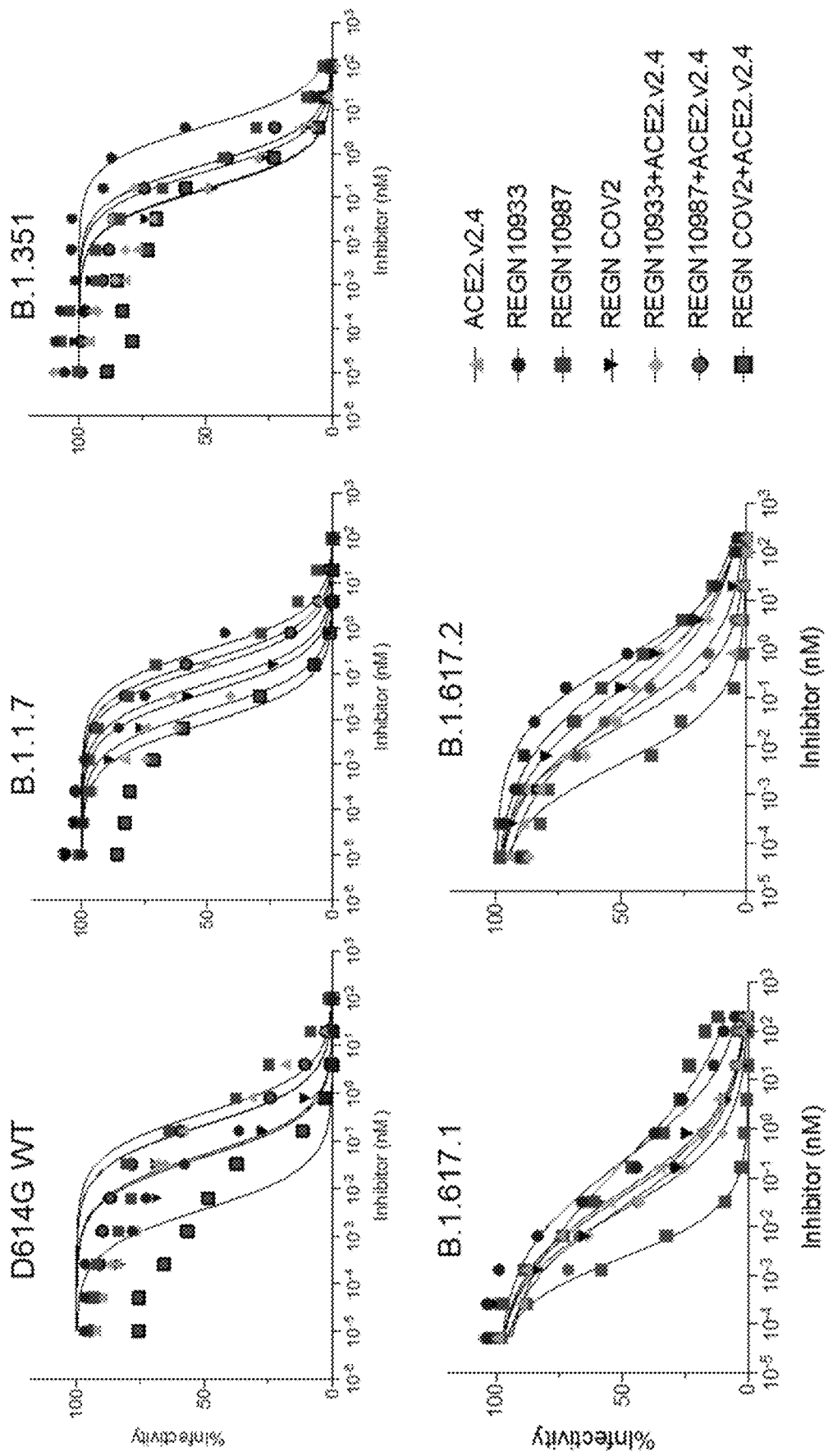

FIG. 11. ACE2.v2.4 microbody synergizes with Regeneron therapeutic monoclonal anti-spike protein antibodies to neutralize virus with variant SARS-CoV-2 spikes. ACE2.v2.4 microbody and Regeneron antibodies REGN10933 and REGN10987 and a cocktail with both were mixed at a 1:1 ratio. A serially diluted mixture was incubated for 30 minutes with SARS-CoV-2 variant pseudotyped viruses (B.1.1.7, B.1.351, B.1.617.1, B.1.617.2) and then added to ACE2.293T cells. Luciferase activity was measured 2 days post-infection and the IC50 (ng/ml) was calculated (table).

Figure 12:
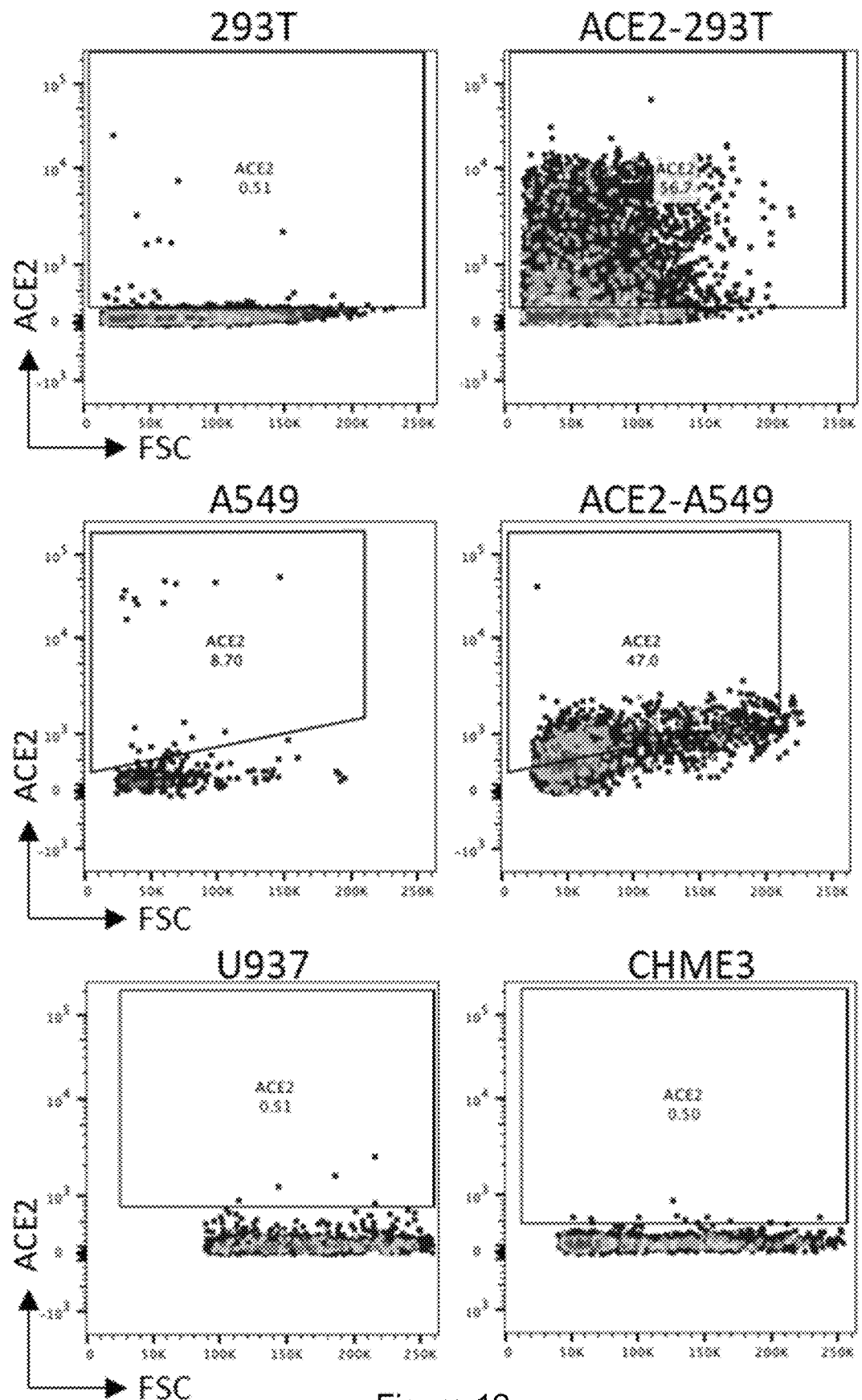
Figure 12:
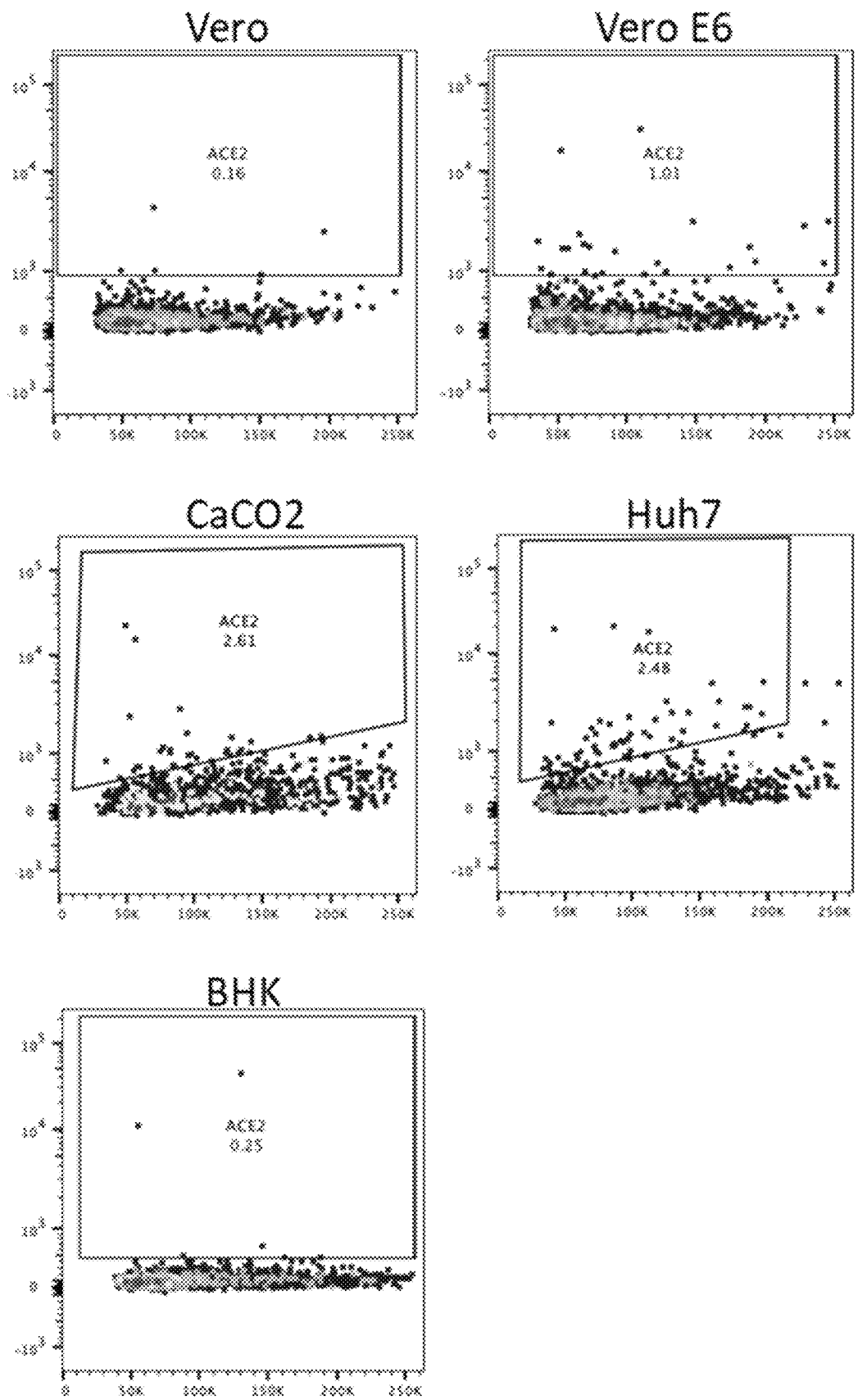

FIG. 12. ACE2 expression levels in cell-lines. The indicated cell lines were stained with anti-ACE2 antibody and Alexa fluor 594-conjugated anti-mouse IgG secondary antibody and analyzed by flow cytometry.

Figure 13:
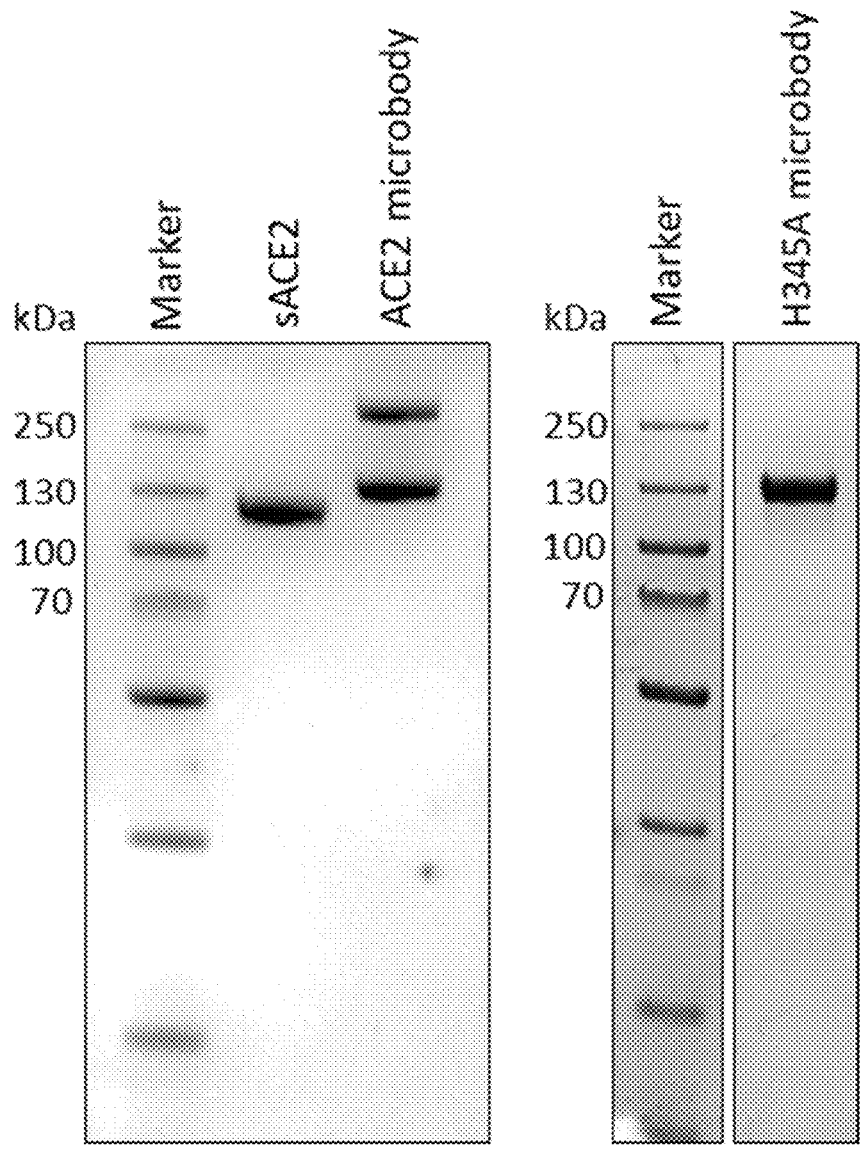

FIG. 13. SDS-PAGE analysis of purified proteins. 30 μg of soluble ACE2, ACE2 microbody (left) and ACE2.H345A microbody (right) were analyzed by Coomassie blue stained SDS-PAGE under reducing conditions. Note, the ACE2 microbody dimer is partially resistant to reduction.

Figure 14:
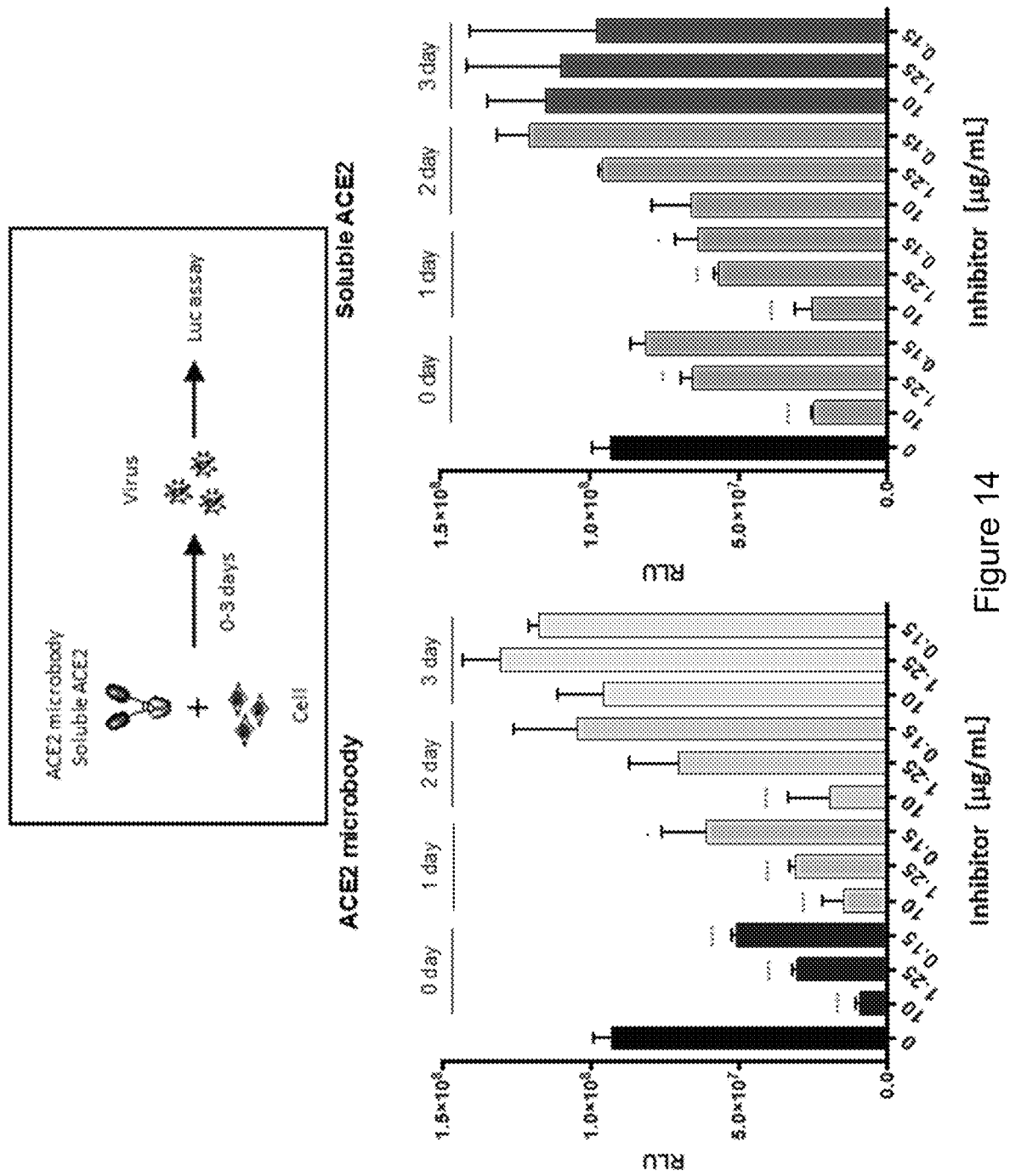

FIG. 14. Increased stability of the ACE2 microbody. Serially diluted sACE2 and ACE2 microbody proteins were added to ACE2.293T target cell cultures. The cells were infected either immediately with SARS-CoV-2 pseudotyped lentivirus or 1, 2 or 3 days later. Luciferase activity was measured 2 days post-infection. The data are presented as the mean of triplicates±SD. Statistical significance was calculated by the student-t test.

Figure 15:
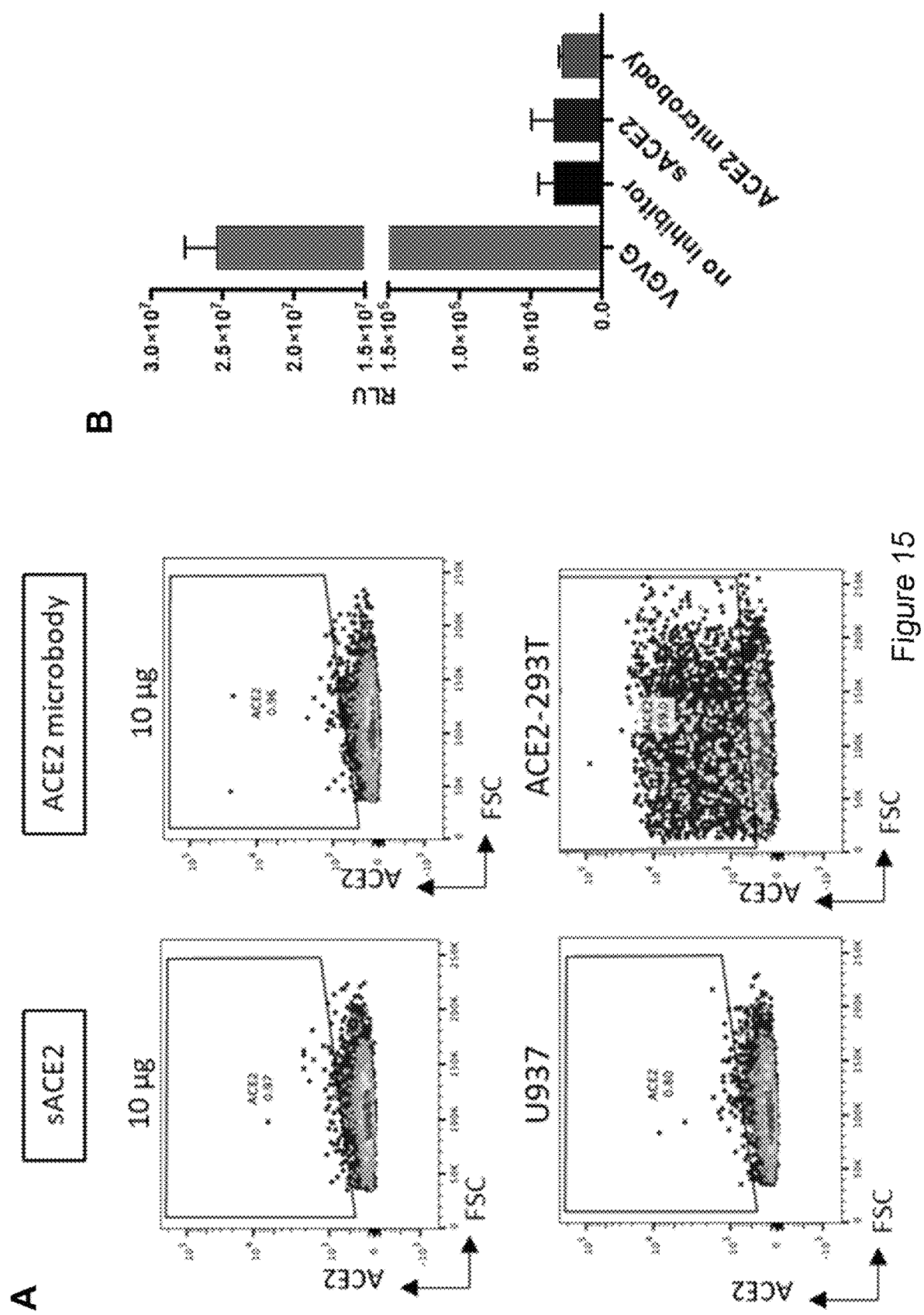

FIG. 15. ACE2 microbody does not bind to Fc receptors. (A) U937 cells were incubated for 30 min. with serially diluted soluble ACE2 or ACE2 microbody. Unbound soluble ACE2 proteins were removed and cell surface-bound proteins were detected by flow cytometry with anti-ACE2 antibody and Alexa fluor 594-conjugated anti-mouse IgG secondary antibody. ACE2.293T cells were analyzed as a positive control for ACE2 staining. (B) Graph related to (A).

Figure 16:
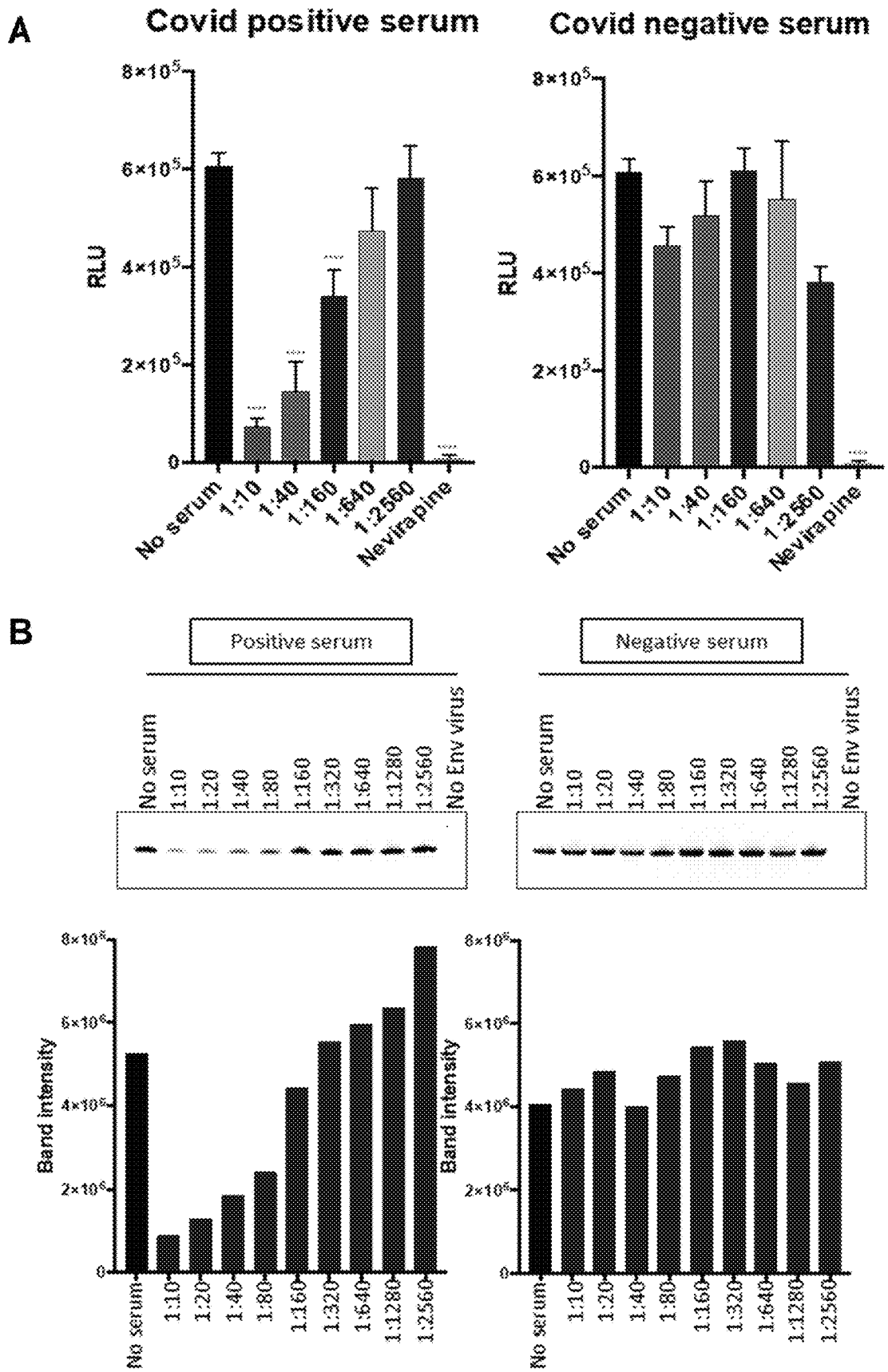

FIG. 16. Titer of convalescent patient serum with SARS-CoV-2 lentiviral pseudotyped virus and effect of serum in virion binding assay. (A) Serially diluted serum from a COVID-19 patient (left) and healthy donor (right) was incubated for 30 minutes with pseudotyped virus and then added to Vero E6 cells. Two days post-infection, luciferase activity was measured. Nevirapine was added to one sample to confirm that signals were the result of bone fide infection. The data are displayed as the mean of triplicates±SD. Statistical significance was calculated by the student-t tests. (B) The ability of convalescent patient serum to block virus binding to ACE2 was tested. Ni-NTA agarose beads were coated with ACE2 microbody proteins. Serially diluted convalescent patient serum or healthy donor serum was incubated for 30 minutes with pseudotyped virions. The virions were then incubated for 1 hour with ACE2 microbody coated-beads. Free virions were removed and the bound protein was analyzed on an immunoblot probed with anti-p24 antibody. A histogram showing band intensities is shown.

Figure 17:
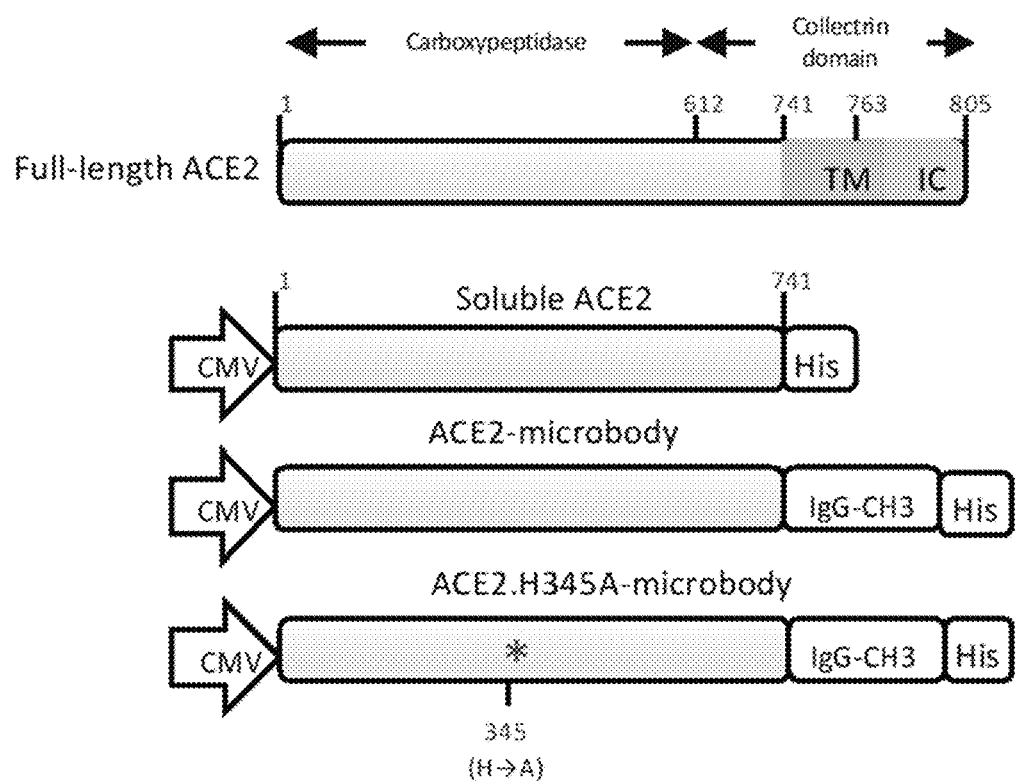

FIG. 17. Schematics showing embodiments of fusion proteins and pertinent sequences.

BRIEF SUMMARY

Soluble viral receptors, initially described for HIV-1, are potent inhibitors of virus replication that act by competitively binding to their respective viral envelope glycoproteins. Soluble forms of ACE2, the receptor for SARS-CoV-2 have recently been shown to be potent inhibitors of virus entry. The present disclosure provides an improved form of soluble ACE2, termed ACE2 "microbody" in which the ACE2 ectodomain is fused to domain 3 of immunoglobulin G Fc. Fusion to the single Fc domain renders the protein smaller that the previously described ACE2 Ig Fc fusion proteins. In addition, the ACE2 microbody was modified by a H345A mutation in the catalytic active site that kills enzymatic activity without reducing of the affinity of the receptor for the SARS-CoV-2 spike. The ACE2 microbody protein potently inhibited entry of SARS-CoV-2 spike pseudotyped virus and live SARS-CoV-2 and maintained its antiviral activity even after initial binding of the virus to the cell. The protein is a disulfide bonded dimer that is 10-fold more active than dimerized soluble ACE2 lacking the Fc domain. The ACE2 microbody inhibited entry of a panel of ACE2-specific β coronaviruses and maintained full activity against the D614G variant spike protein that is associated with increased stability and infectivity. The ACE2 microbody is therefore expected to be a valuable therapeutic for COVID-19 that is broadly active against SARS-CoV-2 spike protein variants that may arise or against ACE2-specific coronaviruses that may enter the human population and non-human animal population in the future.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Any database entry reference, such as reference to a sequence database, incorporated herein the sequence associated with the database entry as it exists on the effective filing date of this application or patent.

The disclosure includes all polynucleotide and amino acid sequences described herein expressly and by reference, and every polynucleotide sequence referred to herein includes its complementary sequence, and its reverse complement. All segments of polynucleotides from 10 nucleotides to the entire length of the polynucleotides, inclusive, and including numbers and ranges of numbers there between are included. DNA sequences includes the RNA equivalents thereof to the extent an RNA sequence is not given. Every DNA and RNA sequence encoding polypeptides disclosed herein is encompassed by this disclosure, including but not limited to sequences encoding all recombinant proteins that comprise any complete protein or segment thereof, as described further below. All of the amino acid sequences and nucleotide sequences associated with any accession numbers are incorporated herein by reference as they exist in the database as of the date of the filing of this application or patent. The disclosure includes all polynucleotide and protein sequences described herein expressly or by reference that are between 80.0% and 99.9% identical to the described sequences. The proteins may comprise one or more than one amino acid changes, in addition to the amino acid change described herein which inhibits the enzymatic function of the ACE2 protein. Such changes can comprise conservative or non-conservative amino acid substitutions, insertions, and deletions, polymorphisms, and the like. Any one or combination of components can be omitted from the claims, including any polynucleotide sequence, any amino acid sequence, and any one or combination of steps.

In view of the foregoing, it will be recognized that the present disclosure provides improved compositions and methods for combatting COVID-19, and other Coronaviruses that express an S protein that binds to ACE2, such as β-Coronoviruses. As noted above, the compositions comprise in certain embodiments an ACE2-"microbody" in which the ACE2 ectodomain is fused to a single IgG CH3 domain of an IgG Fc region. Representative schematics of full length ACE2, soluble ACE2, and an ACE2-microbody fusion protein without a mutation in the ACE2 amino acid sequence, and with a mutation, are depicted in FIG. 17, top panel. Thus, in embodiments, the ACE2 ectodomain comprises a mutation that reduces or eliminates its protease activity. Accordingly, in embodiments, the mutation is in the enzymatically active domain of the ACE2. In embodiments, the ACE2 protease activity is abrogated, such that no detectable cleavage of angiotensin occurs. In embodiments, the amino acid at position 345 in the ACE2 protein is altered relative to a wild type, enzymatically active protein. In embodiments, the amino acid at position 345 in the ACE2 protein is an amino acid other than a Histidine. In embodiments, the amino acid at position 345 is an Alanine. The disclosure includes recombinantly engineered modifications to the fusion protein, such as by including a purification tag, non-limiting examples of which include any sequence that facilitates protein purification, such as a HIS or a FLAG tag. In an embodiment, the purification tag comprises a poly-Histidine tag. In an embodiment, an 8×His tag is used. In embodiments, the His tag is present at the C-terminus of the protein, such as at the C-terminus of the microbody segment. A representative example of a His tag is shown in FIG. 17, (SEQ ID NO:4).

In embodiments, a fusion protein of the disclosure comprises an approximately or precisely 740 amino acid sequence segment of the ACE2 protein, as outlined in FIG. 17 (SEQ ID NO:2), with the exception that position 345 is not a His, and is substituted with, for example, an Ala, or other suitable amino acid such that the protease activity of the protein is reduced or eliminated. An example of this Ala substitution in shown in FIG. 17 (SEQ ID NO:5) in the context of the intact fusion protein, which also demonstrates deletion of the transmembrane domain and the cytoplasmic tail. In particular, for the ACE2 human protein, the extracellular domain is amino acids 1-740, the ransmembrane (TM) domain (is amino acids 741-763, and the cytoplasmic tail is amino acids 764-805. The full-length human ACE2 protein is:

```
                                              (SEQ ID NO: 6)
MSSSSWLLLSLVAVTAAQSTIEEQAKTFLDKFNHEAEDLFYQSSLASWN

YNTNITEENVQNMNNAGDKWSAFLKEQSTLAQMYPLQEIQNLTVKLQLQ

ALQQNGSSVLSEDKSKRLNTILNTMSTIYSTGKVCNPDNPQECLLLEPG

LNEIMANSLDYNERLWAWESWRSEVGKQLRPLYEEYVVLKNEMARANHY

EDYGDYWRGDYEVNGVDGYDYSRGQLIEDVEHTFEEIKPLYEHLHAYVR

AKLMNAYPSYISPIGCLPAHLLGDMWGRFWTNLYSLTVPFGQKPNIDVT

DAMVDQAWDAQRIFKEAEKFFVSVGLPNMTQGFWENSMLTDPGNVQKAV

CHPTAWDLGKGDFRILMCTKVTMDDFLTAHHEMGHIQYDMAYAAQPFLL

RNGANEGFHEAVGEIMSLSAATPKHLKSIGLLSPDFQEDNETEINFLLK
```

```
QALTIVGTLPFTYMLEKWRWMVFKGEIPKDQWMKKWWEMKREIVGVVEP

VPHDETYCDPASLFHVSNDYSFIRYYTRTLYQFQFQEALCQAAKHEGPL

HKCDISNSTEAGQKLFNMLRLGKSEPWTLALENVVGAKNMNVRPLLNYF

EPLFTWLKDQNKNSFVGWSTDWSPYADQSIKVRISLKSALGDRAYEWND

NEMYLFRSSVAYAMRQYFLKVKNQMILFGEEDVRVANLKPRISFNFFVT

APKNVSDIIPRTEVEKAIRMSRSRINDAFRLNDNSLEFLGIQPTLGPPN

QPPVSIWLIVFGVVMGVIVVGIVILIFTGIRDRKKKNKARSGENPYASI

DISKGENNPGFQNTDDVQTSF
```

In embodiments, the microbody segment of the fusion protein is approximately or precisely 131 amino acids, as shown in FIG. 17 (SEQ ID NO:3). It is considered the microbody facilitates dimerization of fusion proteins, and provides additional advantages for therapeutic approaches, such as an improved half-life, and inhibits or prevents binding of the fusion protein to Fc receptors.

In embodiments, a fusion protein of the disclosure comprises approximately or precisely 879 amino acids, which comprises or consists of the described ACE2 protein segment, the microbody segment, the mutation at position 345, and a His tag, as shown in FIG. 17 (SEQ ID NO:5). In embodiments, the fusion protein is a contiguous polypeptide that does not include a linker sequence between the soluble, mutated ACE2 and microbody segments, but a linker may be used if desired. In embodiments, a fusion protein of this disclosure comprises amino acids 1-871 of SEQ ID N0:5, which may optionally include a purification tag having an amino acid sequence beginning at amino acid 872 of SEQ ID NO:5, which is illustrated in FIG. 17 as a Histidine tag.

In embodiments, a composition of the disclosure is administered to an individual who is infected with SARS-CoV-2, or is suspected of having a SARS-CoV-2 infection, or another Coronavirus that causes a deleterious infection.

In embodiments, the composition is administered to an individual who is at risk for contracting a Coronavirus infection, including but not necessarily limited to a SARS-CoV-2 infection. In embodiments, the individual is a human and is of an age wherein such risk is heightened, such as any individual over the age of 50 years. In embodiments, the individual has an underlying condition wherein the risk of developing severe symptoms of a Coronavirus infection, such as COVID-19, is increased, including but not necessarily limited to any respiratory condition. In embodiments, the disclosure includes veterinary approaches, such as for administration to domesticated felines who have or are at risk of developing Feline infectious peritonitis (FIP).

In embodiments, the individual has been diagnosed with or is at risk of contracting a SARS-CoV-2 variant infection. Such variants include but are not necessarily limited to variants currently referred to as variants of interest, variants of concern, and variants of high consequence. In embodiments, the described polypeptides can be administered to an individual who has been diagnosed with or is at risk for contracting a SARS-CoV-2 infection wherein the virus comprises any of D614G, L452R or E484K spike protein amino acid substitutions. In embodiments, the disclosure pertains to prophylaxis or treatment for any SARS-CoV-2 variants currently referred to as Alpha (B.1.1.7), Beta (B.1.351), Gamma (P.1), P.2., B.1.427, B.1.429, or B.1.526.1, Delta (B.1.617.1, B.1.617.2, or B.1.617.2) and lambda (C.37) which is currently termed a Variant of Interest.

In embodiments, an effective amount of a composition is administered to an individual. An effective amount means an amount of the fusion protein that will elicit the biological or medical response by a subject that is being sought by a medical doctor or other clinician. In embodiments, an effective amount means an amount sufficient to prevent, or reduce by at least about 30 percent, or by at least 50 percent, or by at least 90 percent, any sign or symptom of viral infection, e.g., any sign or symptom of COVID-19. In embodiments, fever is prevented or is less severe than if the presently described vaccine had not been administered. In embodiments, viral pneumonia is inhibited or prevented. In embodiments, binding of a Coronavirus to an ACE2 receptor, e.g., binding of a Coronavirus spike protein to an ACE2 receptor, is inhibited or prevented. Thus, in embodiments, viral entry into cells that express the ACE2 inhibitor, including but not necessarily limited to respiratory epithelial cells, can be inhibited or prevented. In embodiments, use of the described polypeptides reduce SARS-CoV-2 viral genome copy number, and/or reduce SARS-CoV-2 virus entry into human cells, and/or inhibit cell death caused by SARS-CoV-2 infection.

In embodiments, the described polypeptides provided in the form of fusion proteins can be provided as pharmaceutical formulations. A pharmaceutical formulation can be prepared by mixing the polypeptides with any suitable pharmaceutical additive, buffer, and the like. Examples of pharmaceutically acceptable carriers, excipients and stabilizers can be found, for example, in Remington: The Science and Practice of Pharmacy (2005) 21st Edition, Philadelphia, PA. Lippincott Williams & Wilkins, the disclosure of which is incorporated herein by reference.

In embodiments, a described polypeptide may be administered with another agent, including but not necessarily limited to anti-viral and anti-inflammatory agents. The polypeptide and additional agent(s) may be administered concurrently or consecutively. The described polypeptide may potentiate the effect of another anti-viral agent. In embodiments, a combination of the described polypeptide and one or more additional agents may exhibit a synergistic anti-viral effect. In embodiments, a described polypeptide may be administered to an individual with one more iminosugars, and/or with one or more antiviral compounds, non-limiting example of which includes nucleoside analogs such as Remdesivir and Galidesivir. In embodiments, a combination of a described polypeptide and an anti-viral antibody is administered. In a non-limiting approach, the polypeptide and one or more anti-SARS-CoV-2 antibodies are administered to an individual in need thereof. In an embodiment, at least one of the anti-SARS-CoV-2 antibodies bind with specificity to an epitope on the viral spike protein. In embodiments, the antibodies are one or both of antibodies known in the art as. In REGN10933 and REGN10987 or other current or future therapeutic anti-spike protein monoclonal antibodies. In embodiments, a combination of the described polypeptide and one or more anti-SARS-CoV-2 antibodies produce synergistic viral neutralization. In embodiments, a combination of agents described herein maintains its ability to inhibit current spike protein variants and is predicted to inhibit future variants that may emerge, so long as they maintain use of ACE-2 as receptor.

Methods of making the described fusion proteins are also included, such as by expressing the fusion protein in a plurality of cells, and separated the express fusion protein from the cells. In embodiments, at least 10 mg/0.5 L are produced.

Administration of formulations comprising the fusion proteins of this disclosure can be performed using any suitable route of administration, including but not limited to parenteral, intraperitoneal, and oral administration. Parenteral infusions include intramuscular, intravenous, intraarterial, intraperitoneal, and subcutaneous administration. The compositions can be administered to humans, and are also suitable for use in a veterinary context and accordingly can be given to non-human animals, including non-human mammals. In embodiments, a single administration is administered and is sufficient for a therapeutic response. In embodiments, more than one administration is provided. In embodiments, non-covalent associations of fusion proteins described herein are formed between the SARS-CoV-2 S protein. Such complexes can be formed anywhere the soluble fusion protein of this disclosure and the SARS-CoV-2 particles can be found in the individual. The disclosure further comprises using the described fusion proteins in diagnostic assays, and thus the fusion proteins may be used, for example, in any type of immunoassay, including but not limited to ELISA assays as, for example, a SARS-CoV-2 or other Coronavirus capture agent or detection agent. Thus, in embodiments, the fusion agents may be detectably labeled. Additionally, the disclosure includes testing test agents (e.g., small molecules) that may interfere with SARS-CoV-2 binding to the ACE2 receptor by, for example, using the fusion protein and the test agents in, for example, competition assays for ACE2 binding. In embodiments, the disclosure provides a fusion protein of this disclosure that is reversibly or irreversibly attached to a substrate. In embodiments, the fusion protein is attached to the substrate via the microbody segment, such as via the His tag. In embodiments, this configuration can be used, for instance, in a screen in which a labeled spike protein is added to a reaction following the addition of one or more test compounds to determine whether or not the test compound(s) compete with the spike protein for binding to the ACE2. This could be performed, for example, in a high throughput screening assay.

The following Examples are intended to illustrate various embodiments of the disclosure, but are not intended to be limiting.

Example 1

SARS-CoV-2 M9 S Protein was Incorporated in Pseudotyped Virion and had Higher Infectivity.

Figure 1:
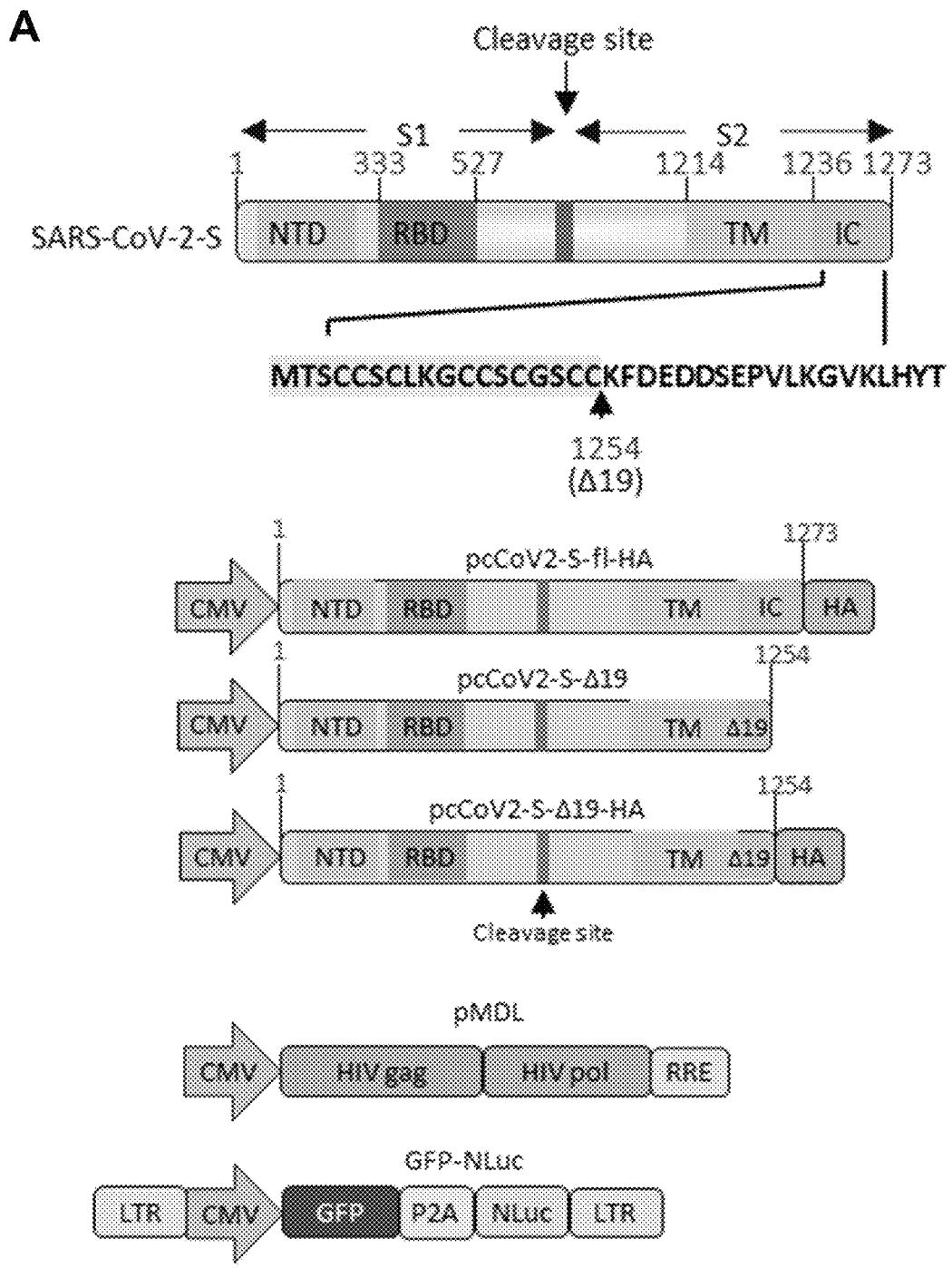
FIG. 1. Δ19 SARS-CoV-2 pseudotyped lentiviral virion infection of ACE2.293T cells and ACE2 expressing cell-lines (A) The domain structure of the SARS-CoV-2 S protein is diagrammed. Yellow shading indicates the amino acids of the cytoplasmic domain retained following truncation of the 19 carboxy-terminal amino acids (Δ19). Vectors encoding full-length (fl) codon-optimized SARS-CoV-2 S protein or truncated Δ19 S protein, with or without a carboxy-terminal HA-tag and the dual nanoluciferase/GFP lentiviral vector pLenti.NLuc.GFP used to generate pseudotyped lentiviral particles are diagrammed. NTD: N-Terminal domain, RBD: Receptor-binding domain, TM: Transmembrane domain IC: intracellular domain, RRE: Rev response element, LTR: Long terminal repeat. (B) SARS-CoV-2 S proteins on pseudotyped lentiviral virions were analyzed. Transfected producer cell lysates (left) and supernatant virions (right) were analyzed on an immunoblot probed with anti-HA antibody. Cell lysate blots were probed with anti-GAPDH to normalize protein loading and virion blots were probed for HIV-1 p24 to normalize for virions. (C) 293T cells transfected with SARS-CoV-2 S protein expression vectors were analyzed by flow cytometry to detect the protein at the plasma membrane. (D) HA-tagged ACE2 expressed in control transfected 293T and clonal ACE2.293T cells were analyzed on an immunoblot probed with anti-HA antibody. (E) ACE2.293T cells were infected with virus pseudotyped by full-length or SARS-CoV-2 Δ19 S proteins. Two days post-infection, infectivity was measured by luciferase assay. The reverse transcriptase inhibitor nevirapine was added to one sample to control for free luciferase enzyme contamination of the virus stock. (F) A panel of cell-lines were infected with VSV-G, SARS-CoV-2 Δ19 S protein or no envelope (no Env) pseudotyped lentivirus. Luciferase activity was measured two days post-infection. The data are represented as the mean of triplicates±the standard deviation. Statistical significance was calculated with the student-t test.
Figure 1:
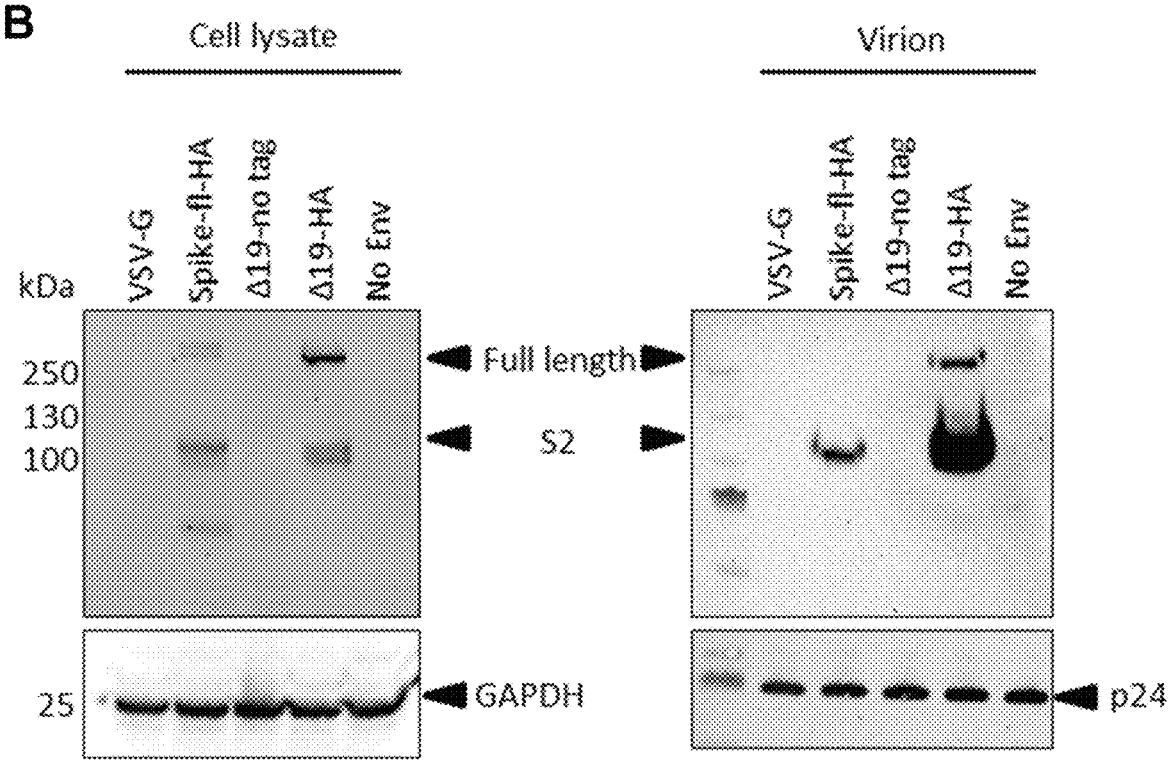
Figure 1:
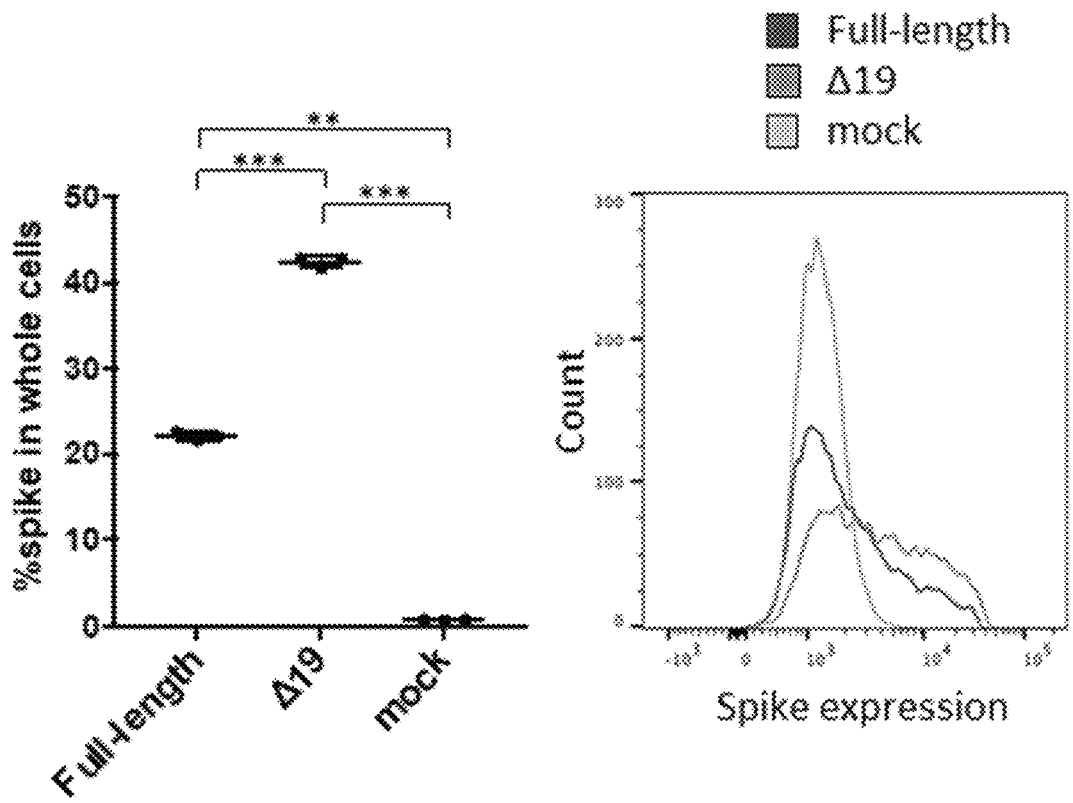
Figure 1:
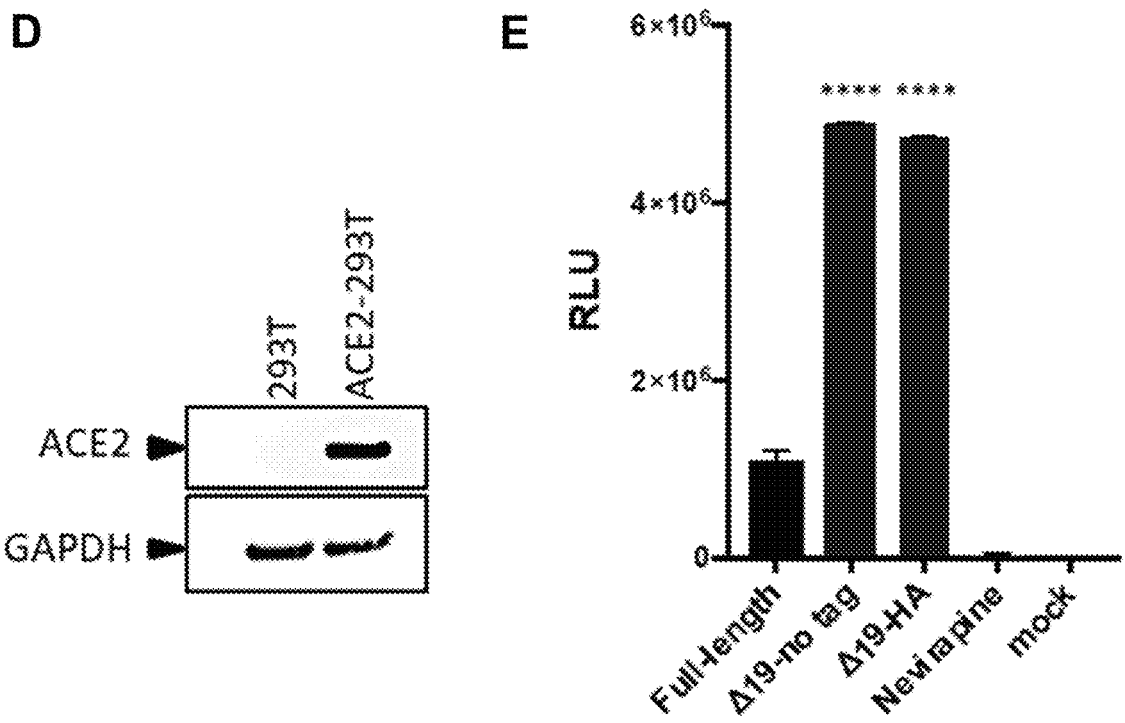
Figure 1:
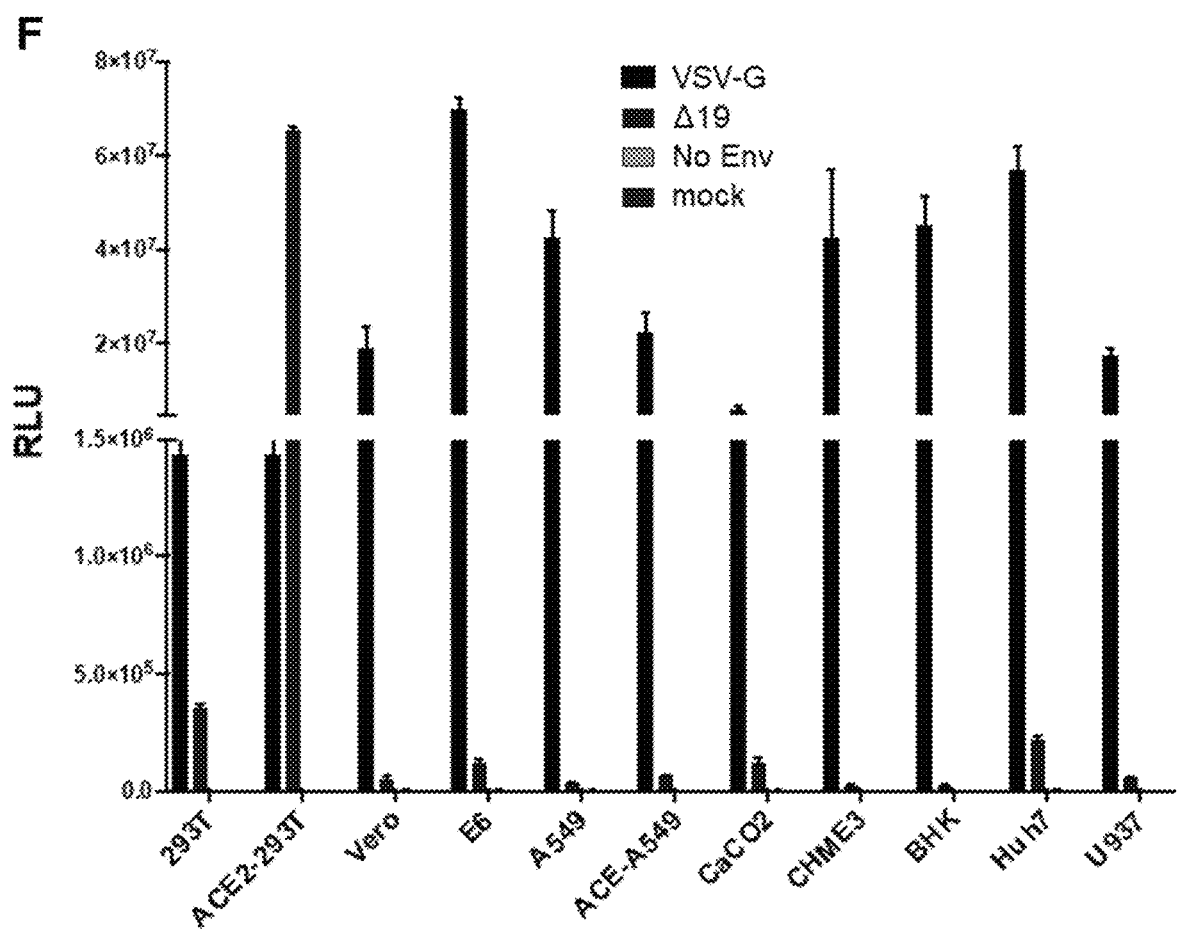

To study SARS-CoV-2 entry and evaluate entry inhibitors, we developed an entry assay based on SARS-CoV-2 spike (S) pseudotyped lentiviral reporter viruses. The viruses package a lentiviral vector genome that encodes nanoluciferase and GFP separated by a P2A self-processing peptide, providing a convenient means to titer the virus and the ability to use two different assays to measure infection. To pseudotype the virions, we constructed expression vectors for the full-length SARS-CoV-2 S or a Δ19 variant deleted for the carboxy-terminal 19 amino acids that removes a reported endoplasmic reticulum retention sequence that blocks transit of the S protein to the cell surface (Giroglou, Cinatl et al. 2004) (FIG. 1A), with or without epitope tags a carboxy-terminal hemagglutinin epitope tag. Virions were produced in 293T cells cotransfected with the dual nanoluciferase/GFP reporter lentiviral vector pLenti.GFP.NLuc, Gag/Pol expression vector pMDL and full-length S protein, the Δ19 S protein, vesicular stomatitis G protein (VSV-G) expression vector or without an envelope glycoprotein expression vector. Immunoblot analysis showed that full-length and Δ19 S proteins were expressed and processed into the cleaved S2 protein (S1 is not visible as it lacks an epitope tag). Analysis of the virions showed that the Δ19 S protein was packaged into virions at >20-fold higher levels than the full-length protein (FIG. 1B). This difference was not the result of differences in virion production as similar amounts of virion p24 were present in the cell supernatant. Analysis of the transfected 293T cells by flow cytometry showed a minor increase in the amount of cell surface Δ19 S protein as compared to full-length (FIG. 1C) suggesting that deletion of the endoplasmic reticulum retention signal was not the primary cause of the increased virion packaging of the Δ19 S protein. As a suitable target cell-line, we established a clonal, stably transfected 293T cell-line that expressed high levels of ACE2 (FIGS. 1D and 12). A comparison of the infectivity of the viruses on ACE2.293T cells showed that the Δ19 S protein pseudotyped virus was about 2.5-fold more infectious (FIG. 1E). The HA-tag had no effect on infectivity and the nevirapine control demonstrated that the luciferase activity was the result of bona fide infection and not carried-over luciferase in the virus-containing supernatant.

To determine the cell-type tropism of the pseudotyped virus, we tested several standard laboratory cell-lines for susceptibility to infection to the Δ19 S protein pseudotyped virus. The VSV-G pseudotype, which has very high infectivity on most cell-types was tested for comparison and virus lacking a glycoprotein was included to control for potential receptor-independent virus uptake. The results showed high infectivity on ACE2.293T cells, intermediate infectivity on 293, Vero, Vero E6, A549, A549.ACE2, CaCO2 and Huh7 and low infectivity on A549, CHME3, BHK and U937 (FIG. 1F). Analysis by flow cytometry of cell surface ACE2 levels showed high level expression on ACE2.293T, intermediate levels expression on ACE2.A549 and low to undetectable levels on A549, CaCO2 and Huh7 (FIG. 12).

Example 2

An ACE2 Microbody Potently Inhibits SARS-CoV-2 S-Mediated Virus Entry.

Figure 2:
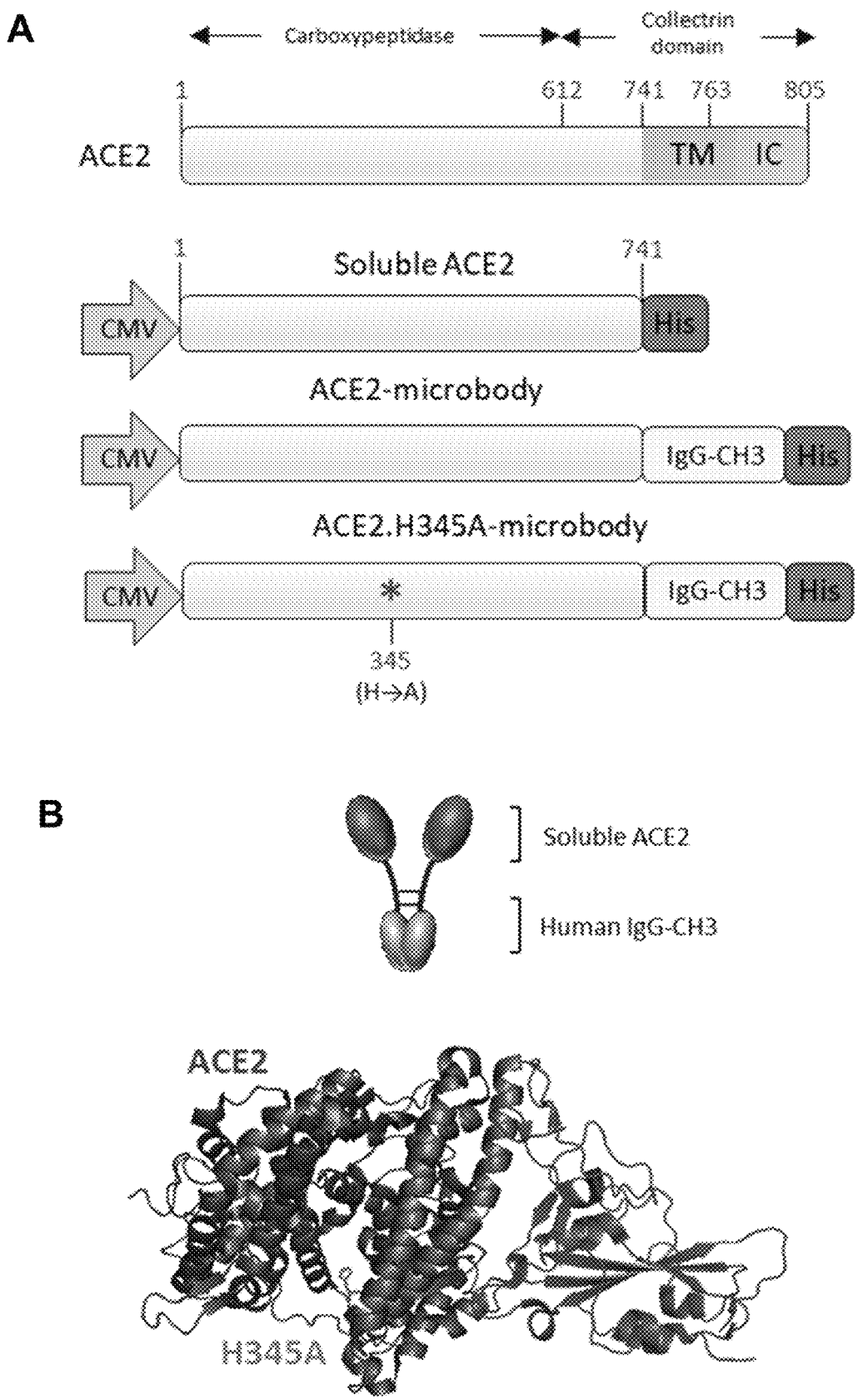
FIG. 2. Wild-type and H345A ACE2 microbody proteins are disulfide bonded dimers. (A) The domains of ACE2 are shown with the structures of the soluble ACE2 (sACE2), ACE2 microbody and H345A ACE2 microbody proteins. The soluble ACE2 proteins are deleted for the transmembrane (TM) and cytoplasmic domains. The ACE2 microbody proteins are fused to the human IgG CH3 domain each with a carboxy-terminal 8×His-tag. IC: intracellular domain. (B) The diagram shows the predicted dimeric structure of the ACE2 microbody protein. The 3D structure of the ACE2: spike complex indicates the position of the conserved active site H345 in the ACE2 carboxypeptidase domain lying underneath the ACE2 interaction site. (C) 293T cells were transfected with sACE2, ACE2 microbody and ACE2.H345A microbody expression vectors. The proteins were pulled-down on NTA agarose beads and analyzed under reducing and nonreducing conditions on an immunoblot probed with anti-His-tag antibody. (D) The soluble ACE2 proteins were purified by metal chelate chromatography and size exclusion chromatography (SEC). The oligomerization state was determined by SEC multi-angle light scattering. The calculated molecular mass is of each is shown.
Figure 2:
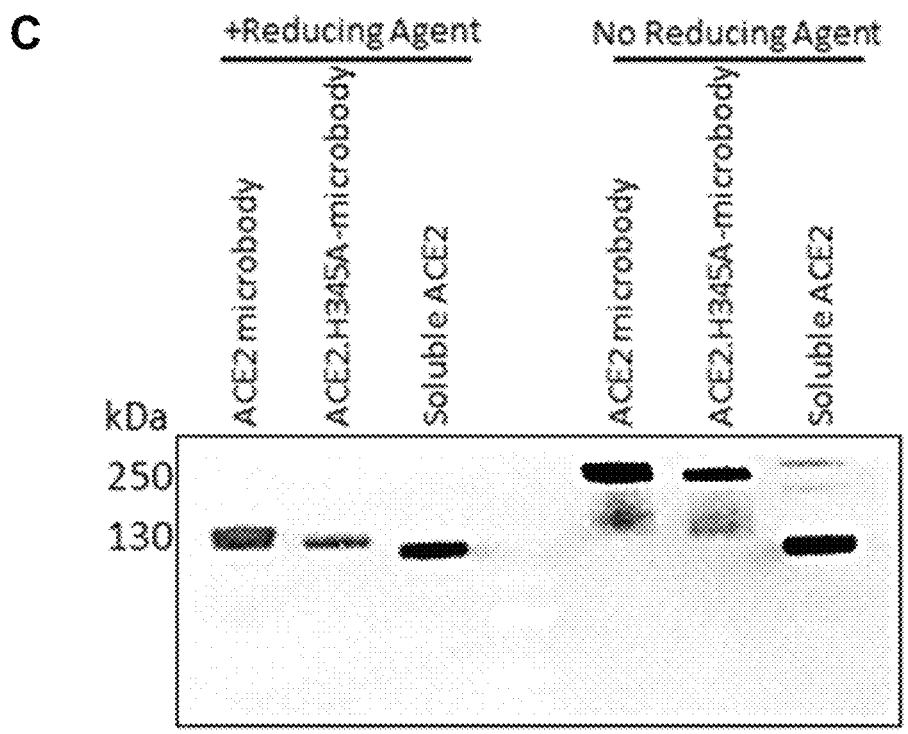
Figure 2:
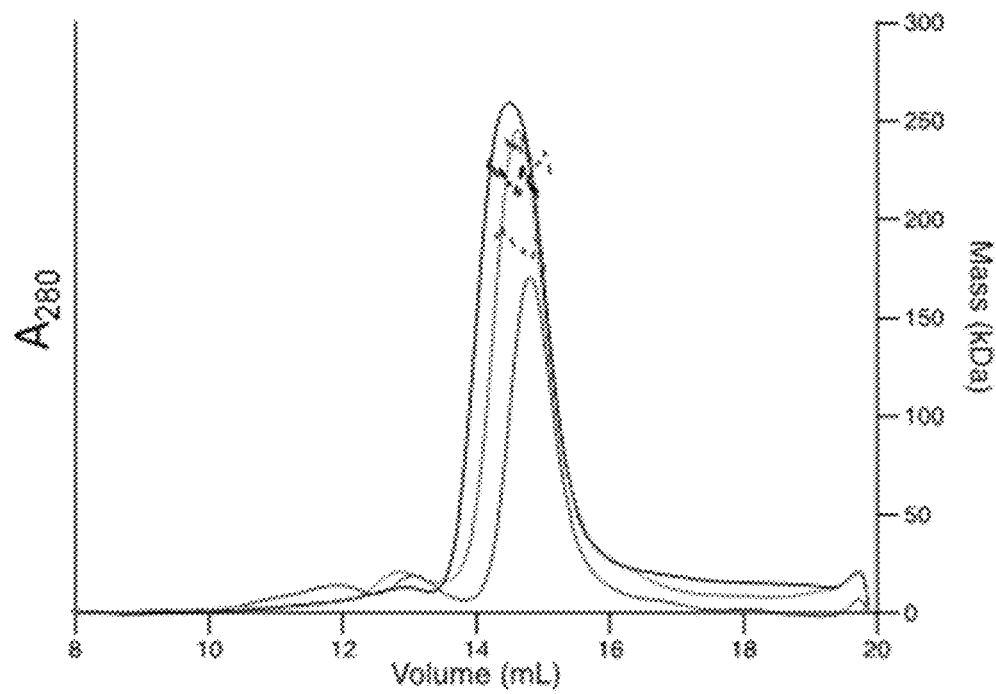

Soluble ACE2 and ACE2-Fc fusions have been shown to inhibit SARS-CoV-2 infection. To increase the effectiveness of soluble ACE2 and improve therapeutic potential, we generated an ACE2-"microbody" in which the ACE2 ectodomain was fused to a single IgG CH3 domain of the IgG Fc region (FIG. 2A). This domain contains the disulfide bonding cysteine residues of the IgG Fc that are required to dimerize the protein, which would serve to increase the ACE2 microbody avidity for ACE2. To prevent potential unwanted effects of the protein on blood pressure due to the catalytic activity of ACE2, we mutated H345, one of the key active site histidines residues of ACE2, to alanine, a mutation that has been shown to block catalytic activity (Guy, Jackson et al. 2005). H345 lies underneath the S protein interaction site so was not predicted to interfere with S protein binding (FIG. 2B). For comparison, we constructed vector encoding soluble ACE2 without the IgG CH3. The proteins were purified from transfected 293 cells and purified to homogeneity by Ni-NTA agarose affinity chromatography followed by size exclusion chromatography (FIG. 13). The oligomerization state of the proteins was analyzed by SDS-PAGE under nonreducing and reducing conditions. Under reducing conditions, the ACE2 and H345A.ACE2 microbody proteins and soluble ACE2 ran at the 130 kDa and 120 kDa, consistent with their calculated molecular mass (FIGS. 2C and 13). Under nonreducing conditions, the soluble ACE2 and ACE2.H345A microbody proteins ran at 250 kDa, consistent with dimers while the soluble ACE2 ran as a monomer (FIG. 2C). Analysis of the proteins by size-exclusion chromatography coupled with multi-angle light scattering (SEC-MALS) under nondenaturing conditions showed all three proteins to have a molecular mass consistent with dimers (FIG. 2D). The mass of the ACE2 and ACE2.H345A microbody proteins was 218 kDa and 230 kDa, respectively, while soluble ACE2 was 180 kDa. Taken together, the results suggest that the ACE2 microbody proteins are disulfide-bonded dimers while soluble ACE2 is a nondisulfide-bonded dimer.

Example 3

ACE2 Microbody Binds to SARS-CoV-2 Pseudotyped Virus.

Figure 3:
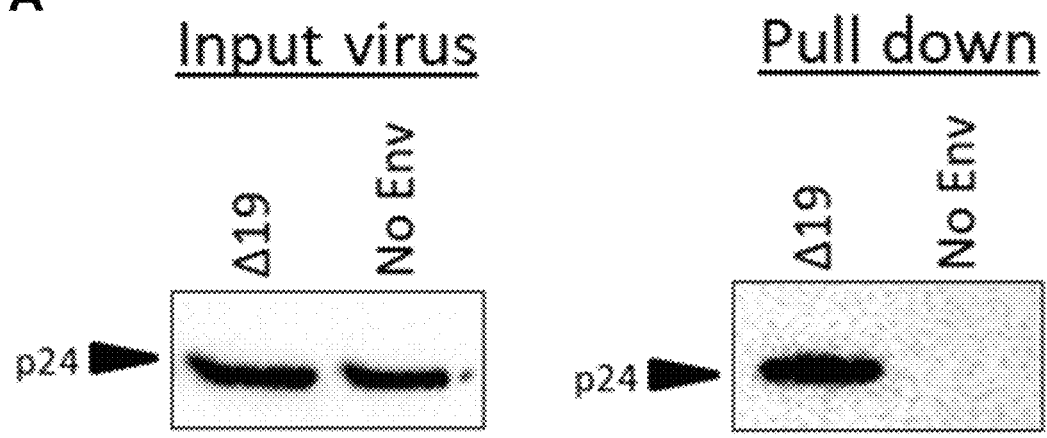
FIG. 3. ACE2 microbody proteins bind with high affinity to SARS-CoV-2 S pseudotyped virions. Nickel agarose beads were coated for 1 hour with 10 of soluble ACE2 proteins. Unbound protein was removed and SARS-CoV-2 Δ19 S pseudotyped virions or virions lacking S protein were incubated with the beads. After 1 hour, unbound virions were removed and the bound virions were analyzed on an immunoblot probed with antibody p24 antibody. (A) Input virions and bead-bound virions were analyzed on an immunoblot probed with anti-p24 antibody. (B) Soluble ACE2 proteins bound to the nickel agarose beads were analyzed on an immunoblot probed with anti-His-tag antibody. (C) Soluble ACE2, wild-type ACE2 microbody, and ACE2.H345A microbody proteins were serially diluted and bound to nickel agarose beads. The amount of bound virions was determined by immunoblot analysis with anti-p24 antibody. Quantification of the band intensities from the immunoblot is graphed for soluble ACE2 (sACE2), wild-type ACE2 microbody (ACE2-mb) and ACE2.H345A microbody (H345A-mb).
Figure 3:
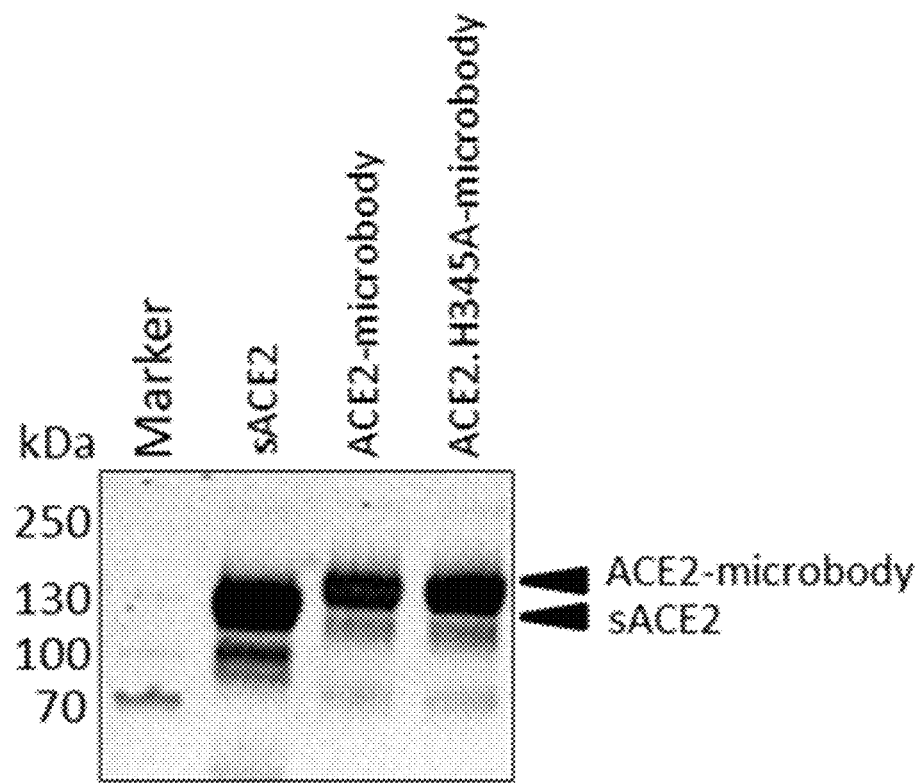
Figure 3:
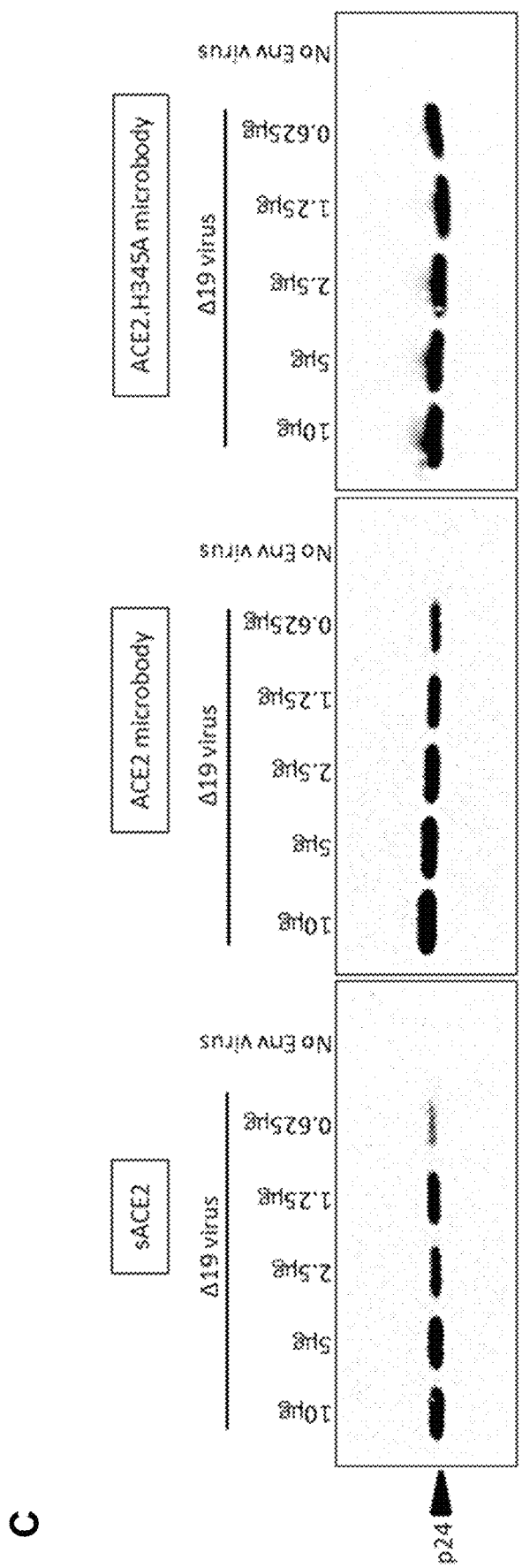
Figure 3:
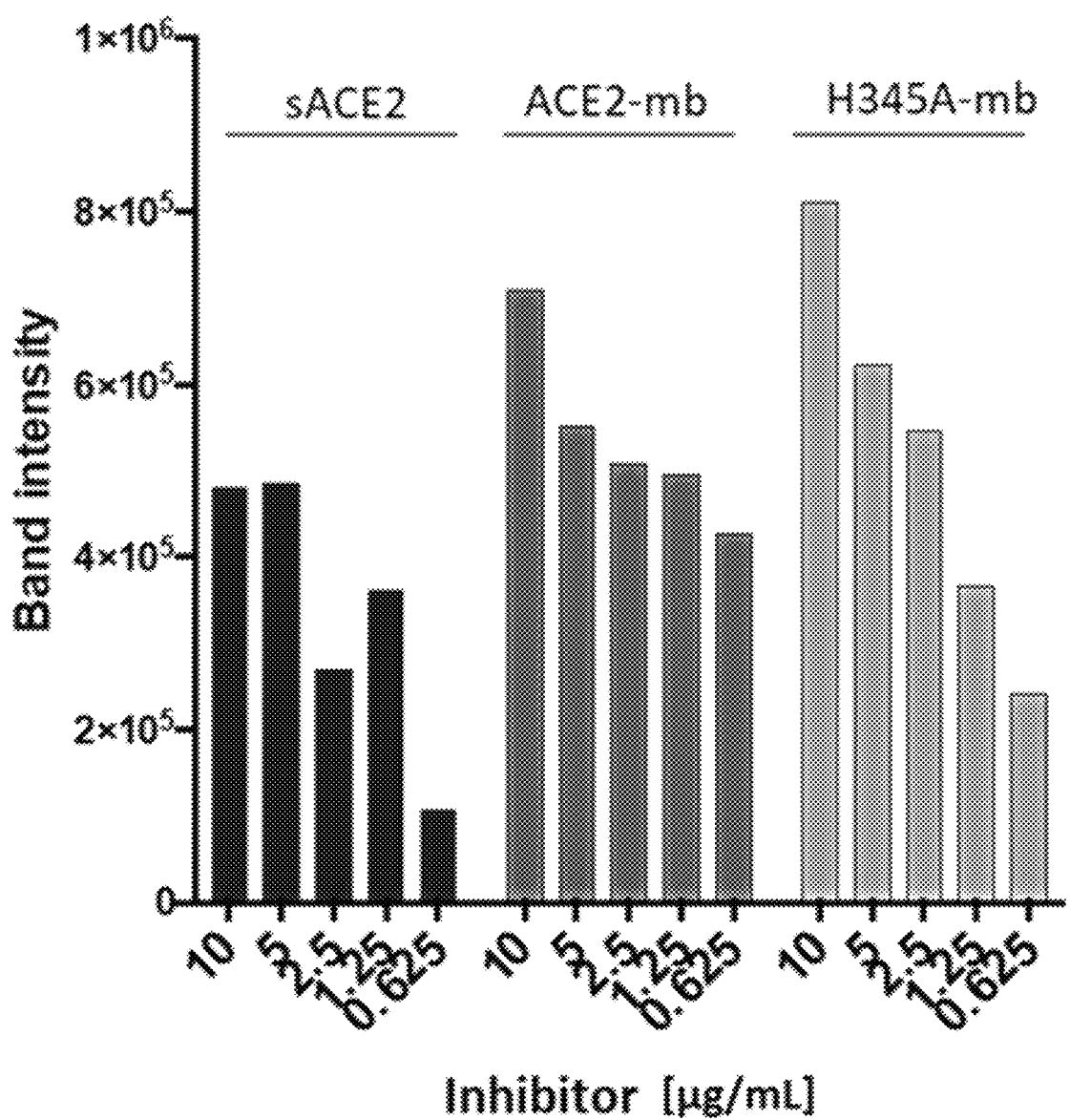

To compare the relative ability of the soluble ACE2 proteins to virions that display the S protein, we established a virion pull-down assay. Ni-NTA beads were incubated with a serial dilution of the carboxy-terminal His-tagged soluble ACE2 proteins. Free spike protein was removed and the beads were then incubated with a fixed amount of lentiviral pseudotyped virions for an hour. Free virions were removed and the amount of virions bound was detected by immunoblot analysis for virion p24 capsid protein. To confirm that virus binding to the beads was specific for the bead-bound ACE2, control virions lacking the spike were tested in the binding assay. The results showed that S protein pseudotyped virions bound to the beads while virions that lacked the S protein failed to bind, confirming that the binding was specific (FIG. 3A). In addition, a high titer human serum from a recovered individual blocked binding of the virions to the bead-bound ACE2 microbody (FIG. 16). Analysis of the soluble ACE2 protein bound to the beads showed that similar amounts of the soluble ACE2 proteins had bound (FIG. 3B). Analysis of virion binding to the soluble ACE2 proteins showed that the wild-type and H345A microbody proteins both bound to virions more efficiently than soluble ACE2 (FIG. 3C). The H345A.ACE2 microbody bound more virions than the wild-type microbody protein which was unexpected as H345 does not lie in the interaction surface with the S protein.

Example 4

ACE2 Microbody Blocks SARS-CoV-2 Pseudotyped Virus Infection.

Figure 4:
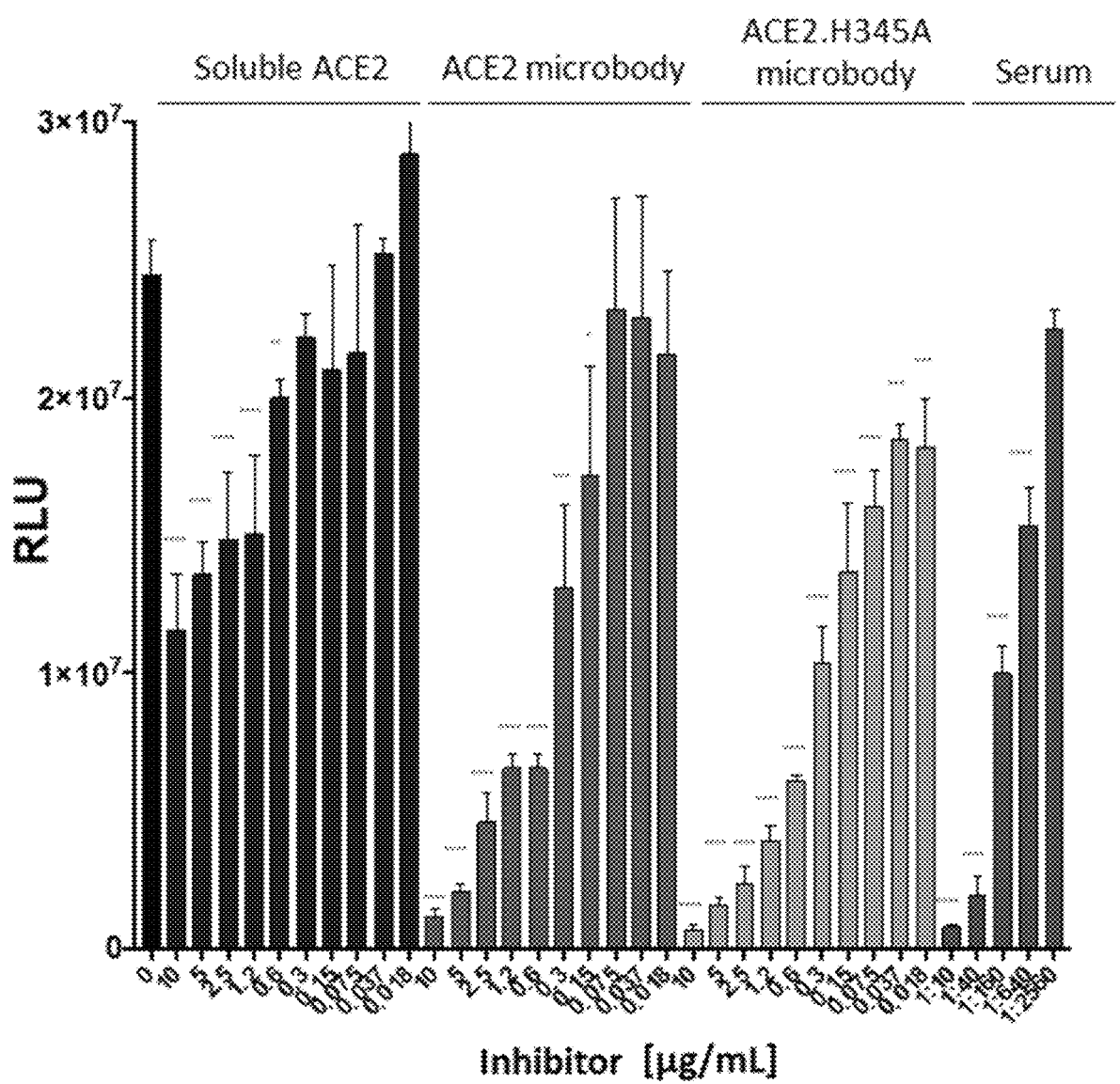
FIG. 4. ACE2 and ACE2.H345A microbodies potently block virus entry and are active on different cell-lines. (A) Serially diluted soluble ACE2, ACE2, and ACE2.H345A microbody proteins were incubated for 30 min with SARS-CoV-2 Δ19.S-pseudotyped virus and then added to ACE2.293T cells. Luciferase activity was measured 2 days post-infection. For comparison, serially diluted convalescent COVID-19 patient serum was similarly analyzed. (B) The number of cells infected was determined by flow cytometry to quantify the GFP+ cells. The data are displayed as the percent GFP+ cells. Representative fluorescence microscopy images of the infected cells are shown below. Scale bar=50 μm. (C) VSV-G pseudotyped lentiviral virions were incubated for 30 min with 10 μg/ml of soluble ACE2 proteins and then added to ACE2.293T cells. Luciferase activity was measured 2 days post-infection. (D) Δ19 S protein pseudotyped virus was incubated with serially diluted soluble ACE2 proteins for 30 min and then added 293T cells. (E) Serially diluted soluble ACE2 proteins were incubated with mNeonGreen SARS-CoV-2 for 30 min. and then added to ACE2.293T cells. After 24 hours, the GFP+ cells were counted. Fluorescent microscopy images of representative fields from wells treated with 1 μg soluble ACE2 and ACE2 microbody proteins are shown. Scale bar=2.1 mm. The data are displayed as the mean±SD and significance is determined by student-t tests.
Figure 4:
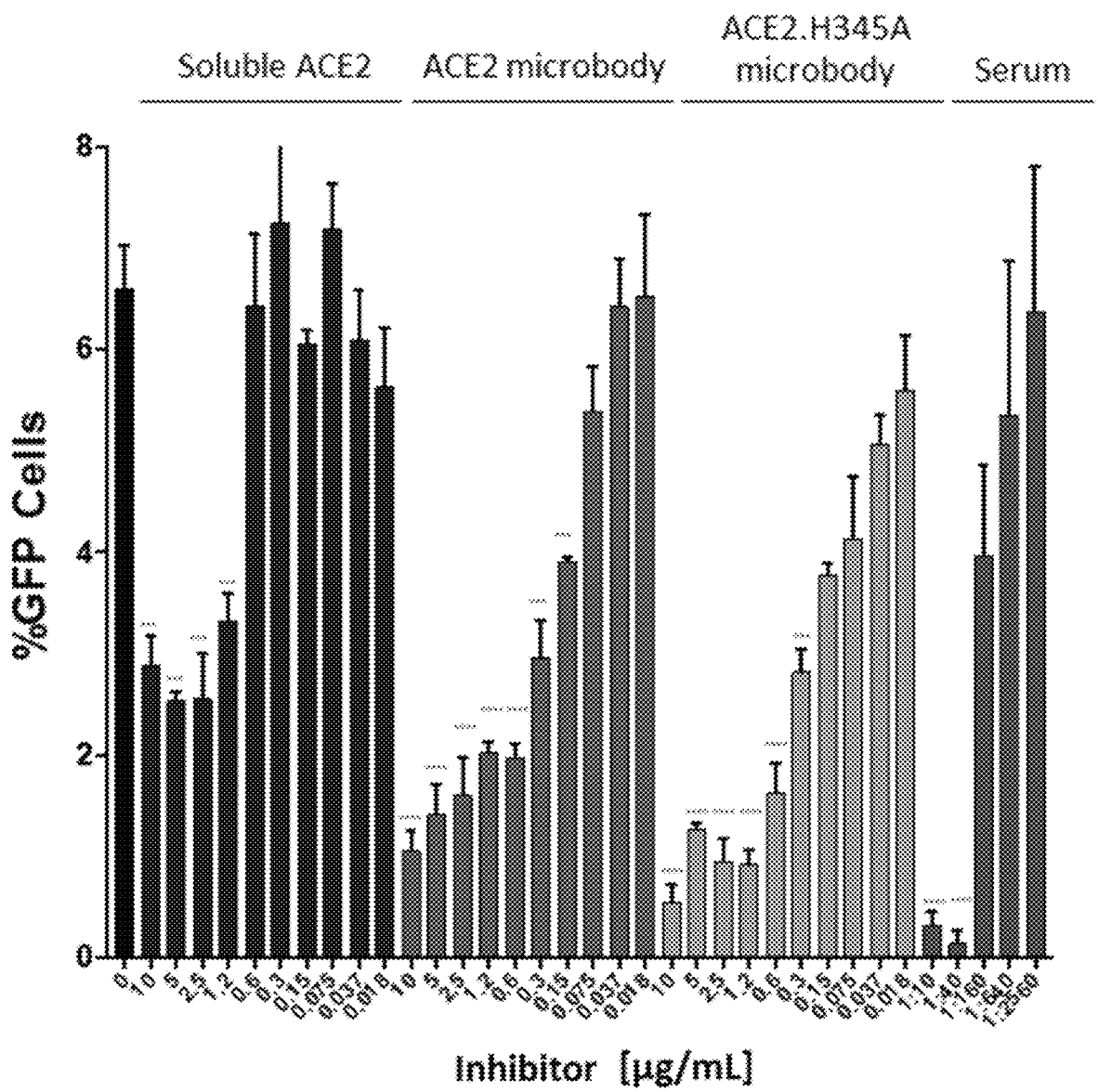
Figure 4:
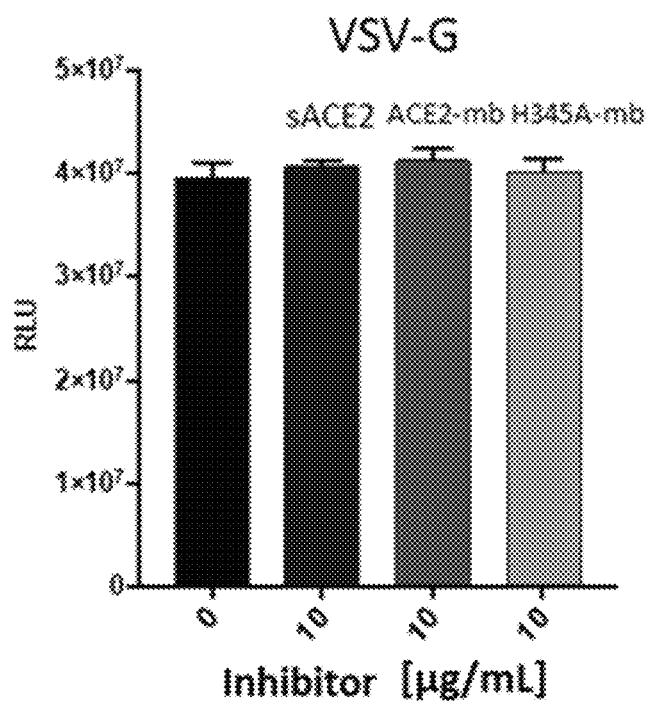
Figure 4:
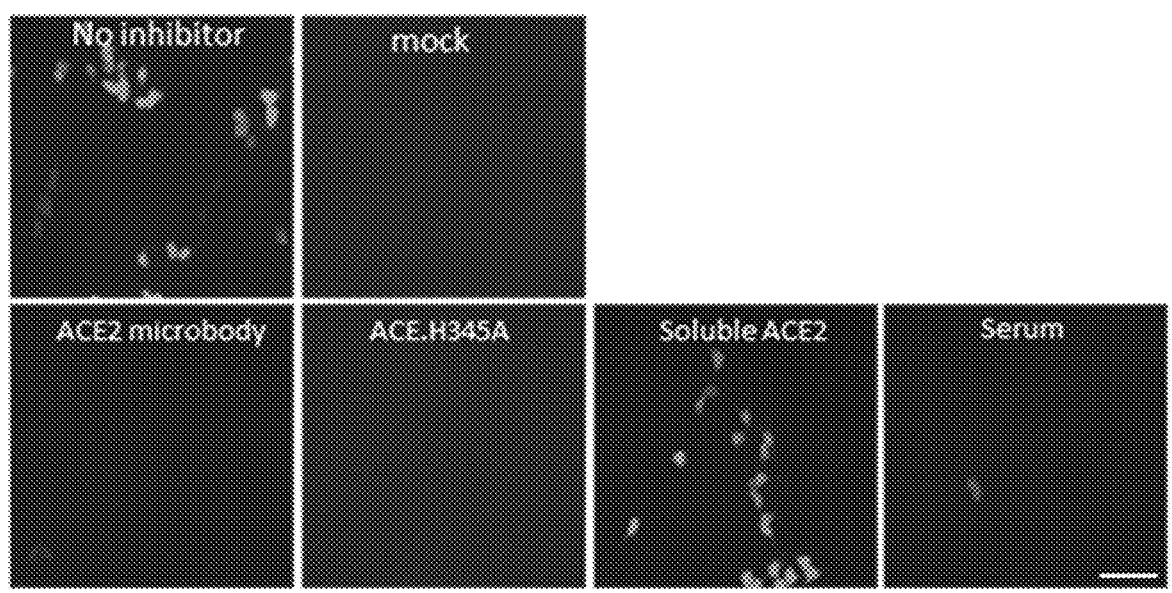
Figure 4:
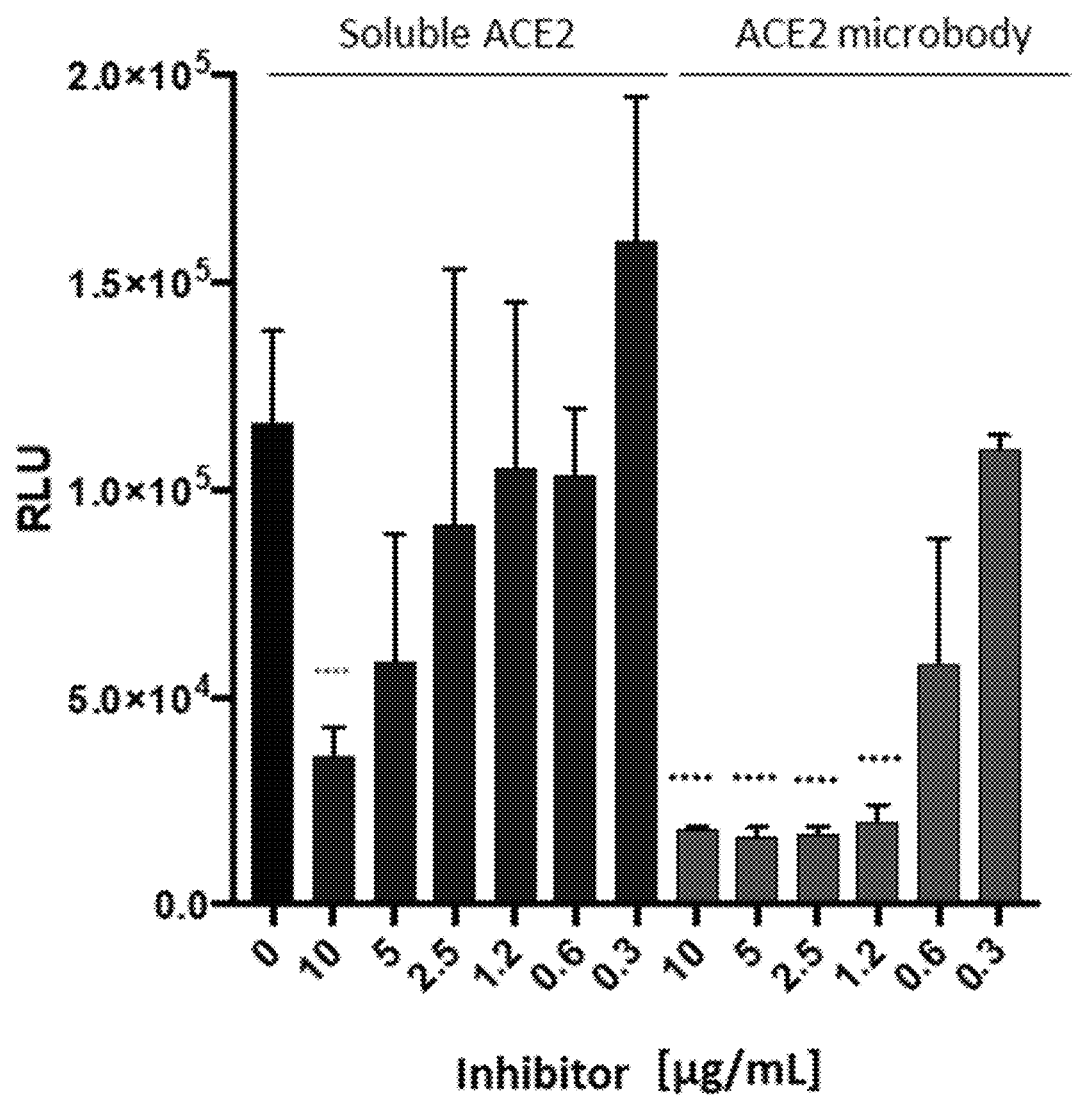
Figure 4:
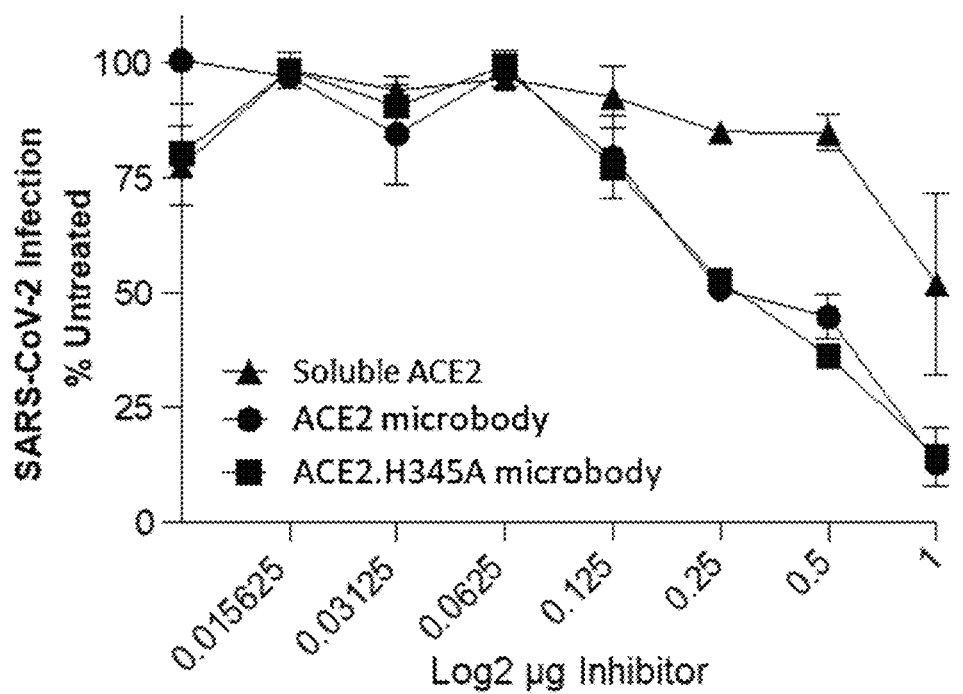
Figure 4:
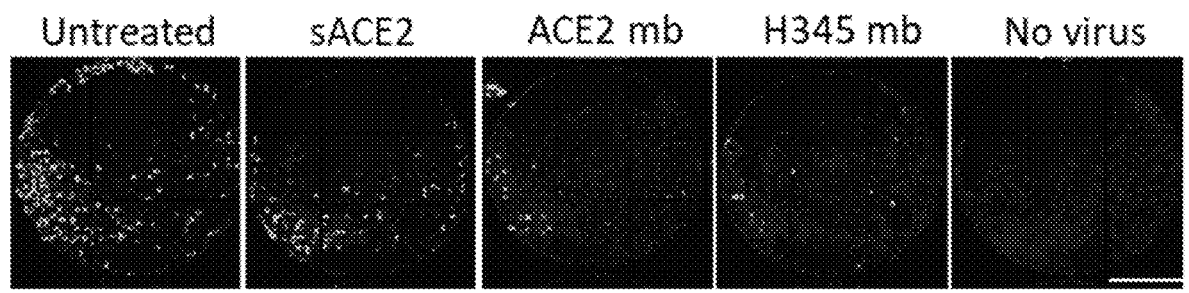

To determine the relative antiviral activity of soluble ACE2 and the ACE2 microbody proteins, we tested their ability to block the infection SARS-CoV-2 Δ19 S protein pseudotyped GFP/luciferase reporter virus. A fixed amount of pseudotyped reporter virus was incubated with the ACE2 proteins and then used to infect ACE2.293T cells. Luciferase activity and GFP in the infected cultures were analyzed after two days. High titered recovered patient serum with a neutralizing titer of 1:330 (FIG. 16) was tested for comparison. The results showed that soluble ACE2 had moderate inhibitory activity with an $EC_{50}$ of 1.24 µg/ml. The ACE2 microbody was significantly more potent, with an $EC_{50}$ of 0.36 µg/ml and the H345A.ACE2 microbody protein was somewhat more potent than the wild-type ACE2 microbody with an $EC_{50}$ of 0.15 µg/ml (FIG. 4A). Inhibition of infection by the soluble ACE2 proteins was comparable to recovered patient serum although it is not possible to directly compare the two inhibitors as the mass amount of anti-S protein antibody in the serum is not known. To confirm the results, we analyzed the infected cells by flow cytometry to determine the number of GFP+ cells. The inhibition curves were similar to the luciferase curves, confirming that the ACE2 proteins had decreased the number of cells infected and did not simply reduce expression of the reporter protein (FIG. 4B). Representative images of the GFP+ cells provide visual confirmation of the results (FIG. 4B). The inhibitory activity of the soluble ACE2 proteins was specific for the SARS-CoV-2 S protein as they did not inhibit VSV-G pseudotyped virus (FIG. 4C). In addition, the ACE2 microbody blocked the infection of 293T (FIGS. 4D and 4E).

To determine the ability of the ACE2 microbody proteins to block the replication of live SARS-CoV-2, we used the replication-competent SARS-CoV-2, icSARS-CoV-2mNG that encodes an mNeonGreen reporter gene in ORF7 (Xie, Muruato et al. 2020). Serially diluted ACE2 microbody proteins were incubated with the virus and the mixture was then used to infect ACE2.293T cells. The results showed that 1-0.125 µg of ACE2 microbody protein blocked live virus replication (Figure. 4E). Soluble ACE2 was less active. 1 µg of the protein had a 50% antiviral effect and the activity was lost with 0.5 µg. The antiviral activity of ACE2 proteins against live virus was similar to pseudotyped virus.

In the experiments described above, the ACE2 microbody proteins were incubated with virus prior to infection. To determine when the soluble ACE2 protein needs to be present to block virus entry, the inhibitors were tested in an "escape from inhibition" assay in which the ACE2 microbody was added to cells at the same time as virus or up to 6 hours post-infection. The results showed that addition of the microbody together with the virus (to) blocked the infection by 80%. Addition of the microbody 30 minutes post-infection maintained most of the antiviral effect, and even 2 hours post-infection the inhibitor maintained most of its blocking activity, blocking 55% of the infection. At 4 hours post-infection, the ACE2 microbody retained its blocking activity at 10 µg/ml but was less active with decreasing amounts of inhibitor (FIG. 5A). These results suggest that the ACE2 microbody is highly efficient at neutralizing the virus when present before the virus has had a chance to bind to the cell. The ACE2 microbody maintains its ability to block infection when added together will the cells and even 2 hours after the virus has been exposed to cells, a time which free virus has not yet bound to the cell and is available to be neutralized.

To determine whether the ACE microbody could prevent virus entry once the virus had bound to the cell, we prebound the virus by incubating it at 22° C. with cells for 1 hour, removed the unbound virus and then added the ACE2 microbody at increasing time points. The results showed that removal of the unbound virus after 1 hour incubation resulted in less infection as compared to when the virus was incubated with the cells for 4 hours at room temperature, indicating that only a fraction of the virus had bound to cells. However, virus that was bound could be blocked by the ACE2 microbody for another 30 minutes post-binding (FIG. 5B). The ability to block entry of the cell-bound virus suggests that virus binding results from a small number of spike molecules binding to ACE2 and that over the next 30-60 minutes, additional spike:ACE2 interactions form. The results demonstrate that the ACE2 microbody is a highly potent inhibitor of free virus and maintains its antiviral activity against virus newly-bound to the cell.

Example 5

ACE2 Microbody Blocks Entry of Virus with D614G Mutant Spike.

A variant SARS-CoV-2 containing a D614G point mutation in the S protein has been found to be circulating in the human population with increasing prevalence (Daniloski, Guo et al. 2020, Eaaswarkhanth, Al Madhoun et al. 2020, Korber, Fischer et al. 2020, Zhang, Jackson et al. 2020). The D614G mutation was found to increase the stability of the spike protein on the virus, resulting in increased infectivity. To determine the ability of the soluble ACE2 proteins to block entry of virus with the D614G S protein, we introduced the mutation into the Δ19 S protein expression vector and generated pseudotyped reporter viruses (FIG. 6A). Analysis of the infectivity of the D614G and wild-type pseudotyped viruses on the panel of cell-lines showed that the mutation increased the infectivity of virus 2-4 fold on 293T, ACE2.293T, Vero and VeroE6 cells, consistent with previous reports. Infectivity of the mutated virus was also increased in A549, ACE2.549 CaCO2 although the overall infectibility of these cells was low (Figure. 6B). To determine the ability of the soluble ACE2 proteins to neutralize the variant virus, serial dilutions of the soluble ACE2 proteins were tested for their ability to block wild-type and D614G S pseudotyped virus. The results showed that sACE2 had moderate antiviral activity against wild-type virus, while the wild-type and H345A microbody proteins were more potent (FIG. 6C). The H345A microbody was somewhat more active at low concentrations than the wild-type protein. To test the relative binding affinity of the soluble ACE2 proteins for wild-type and D614G mutated spike, we tested the pseudotyped virions in the ACE2 virus binding assay (FIG. 6D). The results showed that virus with the D614G S bound efficiently to soluble ACE2.

Example 6

ACE2 Microbody is Effective Against Other β Coronavirus S Proteins.

To determine how well the ACE2 microbody would block the entry of other β coronaviruses, lentiviral virions pseudotyped by S proteins from a panel of different lineage 2 β coronaviruses that use ACE2 for entry (Letko and Munster 2020) (pcSARS-CoV, pcSARS-CoV2, pcWIV1, pcLYRa11, pcRs4231, pcRs4084 and pcSHC014) were generated. The pseudotypes were incubated with soluble ACE2 and the ACE2 microbody proteins and their infectivity was then measured on ACE2.293T cells. The analysis showed that the ACE2 and H345A microbody proteins blocked the all of the β coronavirus pseudotypes while the antiviral activity of soluble ACE2 was significantly diminished in comparison (FIG. 7). The results indicate broad activity of the ACE2 microbody.

Example 7

The ACE-2 Microbody is Able to Protect from Infection with Live SARS-CoV-2 in an Animal Model.

The protein was produced as a recombinant protein in CHO cells and purified by chromatography. Mice transgenic for human ACE-2 were then treated intranasally with live virus and the recombinant protein. While control mice became infected, lost weight and died several days later, the ACE-2 microbody-treated mice were protected (FIG. 8). The finding suggests that the microbody protein is able in vivo to protect against infection and suggest that the protein could help to reduce SARS-CoV-2 replication in infected humans.

Example 8

The ACE-2 Microbody has an Extended Half-Life In Vivo.

The microbody protein was produced as a fusion to nanoluciferase at its carboxyterminal. The protein was injected into mice and monitored both in the live mice and in the organs of the mouse. The results showed that the microbody protein had a much longer half-life than soluble ACE-2 that lacked the truncated Fc domain (FIG. 9). The results suggest that the protein will be much more effective when used to treat COVID-19 than soluble ACE-2 lacking the truncated Fc domain.

Example 9

A New and Improved Version of the Microbody Protein was Produced and Shown to have Increased Antiviral Activity Against the SARS-CoV-2 Variants of Concern (VOC).

The new protein contains three mutations that were reported by Proko et al. to increase ACE-2 affinity for the virus spike protein. Testing of the protein termed ACE-2.ver2.4 showed that it has >10-fold more antiviral activity and that it blocks all of the known VOCs (FIG. 10).

Example 10

The ACE-2 Microbody Synergized with the Regeneron Monoclonal Anti-Spike Protein Monoclonal Antibodies to Increase their Antiviral Potency.

The Regeneron antibodies are potent when used as a two-antibody cocktail. Addition of the ACE-2 microbody to the cocktail further enhanced the antiviral activity of the cocktail, resulting in an ultra-potent inhibitor (FIG. 11). The three-component mixture could serve as a powerful inhibitor of SARS-CoV-2 replication in COVID-19 patients that would alleviate disease severity.

Example 11

Methods

Plasmids.

The dual GFP/nanoluciferase lentiviral vector pLenti.GFP.NLuc was generated by overlap extension PCR. A DNA fragment encoding GFP was amplified with a forward primer containing a BamH-I site and a reverse primer encoding the P2A sequence. The nanoluciferase gene (NLuc) was amplified with a forward primer encoding the P2A motif and a reverse primer containing a 3'-Sal-I site. The amplicons were mixed and amplified with the external primers. The fused amplicon was cleaved with BamH-I and Sal-I and cloned into pLenti.CMV.GFP.puro (Addgene plasmid #17448, provided by Eric Campeau and Paul Kaufman) (Campeau, Ruhl et al. 2009).

The SARS-CoV-2 S expression vector pcCOV2.S was chemically synthesized as DNA fragments A and B encoding codon-optimized 5' and 3' halves, respectively, of the S gene of Wuhan-Hu-1/2019 SARS-CoV-2 isolate (Table 2 and 3). Fragment A was amplified with a forward primer containing a Kpn-I site and reverse primer containing an EcoR-I site. The amplicon was cleaved with Kpn-I and EcoR-I and cloned into pcDNA6 (Invitrogen). Fragment B was amplified with a forward primer containing an EcoR-I site and reverse primer containing Mlu-I and Xho-I sites. The amplicon was cleaved with EcoR-I and Xho-I and cloned into pcDNA6. The cloned fragment A was then cleaved with Mlu-I and Xho-I and cloned into the Mlu-I and Xho-I sites in the fragment B-containing plasmid. To generate the SARS-CoV-2 S 419 expression vector pcCoV2.S.419, the codon-optimized S gene was amplified with a forward primer containing a Kpn-I site and reverse primer that deleted the 19 carboxy-terminal amino acids and contained an Xho-I site. The amplicon was cloned into the Kpn-I and Xho-I of pcDNA6. The D614G mutation in S was generated by overlap extension PCR of the Δ19 S gene using internal primers overlapping the sequence encoding D614G and cloned into pcDNA6. Beta coronavirus spike expression vectors (Letko and Munster 2020) (pcSARS-CoV, pcSARS-CoV2, pcWIV1, pcLYRa11, pcRs4231, pcRs4084 and pcSHC014) were kindly provided by Michael Letko and Vincent Munster (NIH). E484K, B.1.1.7, B.1.351, B.1.1.248, NY1 (E484K), NY2 (S477N), B.1.617.1, B.1.617.2 spike mutations were introduced into pcCOV2.Δ19.D614GS by overlap extension PCR and confirmed by DNA nucleotide sequencing.

ACE2 expressing lentiviral vector pLenti.ACE2 was generated by amplifying an ACE2 cDNA (Origene) with a forward primer containing an Xba-I site and reverse primer containing a Sal-I site. The amplicon was cleaved with Xba-I and Sal-I and cloned into pLenti.CMV.GFP.puro in place of GFP. The soluble ACE2 expression vector pcsACE2 was generated by amplifying the extracellular domain of ACE2 with a forward primer containing a Kpn-I site and reverse primer encoding an in-frame 8×His-tag and Xho-I site. The amplicon was then cloned into the Kpn-I and Xho-I sites of pcDNA6. The ACE2 microbody expression vector pcACE2-microbody was generated by overlap extension PCR that fused the extracellular domain of ACE2 with human immunoglobulin G heavy chain Fc domain 3 using a forward primer containing a Kpn-I site and reverse primer containing an 8(His)-tag and Xho-1 site. The amplicon was cloned into the Kpn-I and Xho-I sites of pcDNA6. Expression vector pcACE2.H345A-microbody that expressed the H345AACE2 microbody was generated by overlap extension PCR using primers that overlapped the mutation. Full-length cDNA sequence, primer sequences and amino acid sequences are shown in Tables 1-3.

Mouse Care and In Vivo SARS-CoV-2 Neutralization.

K18-hACE2 mice [B6.Cg-Tg(K18-ACE2)2Prlmn/J (Mc-Cray et al., 2007)] were purchased from The Jackson Laboratory and bred in-house. SARS-CoV-2 P1 stock was generated by inoculating Vero E6 cells with SARS-CoV-2 isolate USA-WA1/2020 (BEI Resources, NR-52281). The P1 stock was then used to inoculate Vero E6 cells at a MOI 0.01. After three days, the supernatant was harvested, clarified by centrifugation at 450×g for 5 minutes, filtered through a 0.45-micron filter and stored in aliquots at −80° C. Virus titer was determined by plaque assay on Vero.E6 cells (Wei et al., 2020). SARS-CoV-2 (2.0×104 PFU/ml) was mixed with ACE2 microbody (150 μg/ml) or buffer control and incubated for 30 minutes at room temperature. K18-hACE2 mice were anesthetized with 30% vol/vol isoflurane diluted in propylene glycol and administered 50 μl of the mixture (1×103 PFU SARS-CoV-2+7.5 μg ACE2 microbody or volume-matched buffer control) intranasally. The mice were weighed and monitored daily for survival. Animal use and care was approved in agreement with the Yale Animal Resource Center and Institutional Animal Care and Use Committee (#2018-20198) according to the standards set by the Animal Welfare Act.

Cells.

Vero E6, CaCO2, A549, ACE2 A549, BHK, Huh7 293T, Vero and CHME3 cells were cultured in Dulbecco's modified Eagle medium (DMEM) supplemented with 10% fetal bovine serum (FBS) and penicillin/streptomycin (P/S) at 37° C. in 5% $CO_2$. CaCO2 cells were cultured in DMEM/10% FBS/1% nonessential amino acids. U937 cells were cultured in RPMI/10% FBS/ with P/S. ExpiCHO-S (Thermo Fisher Scientific) were cultured in ExpiCHO expression medium at 37° C. in 8% $CO_2$. Cell-line ACE2 expression levels were quantified by staining with anti-ACE2 antibody (NOVUS) and Alexa-fluor 594-conjugated goat anti-mouse IgG (Biolegend) and pacific blue viability dye. Data were analyzed by flow cytometry with Flowjo software. ACE2.293T cells were established by lipofection of 293T cells with pLenti.ACE2-HA using lipofectamine 2000 (Invitrogen). After 2 days, the cells were selected in 1 μg/ml puromycin and cloned at limiting dilution. Single cell clones were expanded and analyzed by flow cytometry and a single clone was chosen.

Monoclonal Antibodies.

cDNAs encoding REGN10933 and REGN10987 were synthesized using published sequences and fused to IgG1 heavy chain and lambda light chains, respectively and cloned into pcDNA3.1 (Invitrogen). The proteins were produced in transfected 293F cells and collected from the cell supernatant after four days. The antibodies were purified on an AKTA prime FPLC with HiTrap Pro A 5 cc column.

SARS-CoV-2 Pseudotype Reporter Virus Assay.

SARS-CoV-2 S protein pseudotyped lentiviral stocks were produced by cotransfecting 293T cells ($4\times10^6$) with pMDL, pLenti.GFP-NLuc, S protein expression vector and pRSV.Rev at a mass ratio of 4:3:4:1 by calcium phosphate coprecipitation. S protein expression vectors used were pcCoV2.S, pcCoV2.S-419 or the β coronavirus RBD expression vectors. Control viruses were produced substituting the S protein vector for pcVSV or with pcDNA6 to produce virus lacking S protein. Virus-containing supernatant was harvested 2 days post-transfection, passed through a 0.45 μm filter and concentrated by ultracentrifugation over a 20% sucrose cushion at 30,000 RPM for 90 min in an SW40.1 rotor in a Beckman Optima L-100K ultracentrifuge (Brea, CA). The pellet was resuspended to 1/10 the initial volume in DMEM/10% FBS and frozen in aliquots at −80° C. Virus stocks were titered on 293T by flow cytometry and for luciferase activity. The p24 concentration was measured and the virus was used at a concentration of 1.0 μg/ml. To test the inhibitory activity of soluble receptors and convalescent sera, 50 μl serially diluted inhibitor or convalescent patient serum was incubated for 30 min. at room temperature with 5 μl pseudotyped reporter virus (approximately $5\times10^6$ cps luciferase activity/μl) at a MOI of 0.1 in a volume of 100 μl. The mixture was added to ACE2.293T cells in a 96 well tissue culture dish containing $1\times10^4$ cells/well. After 2 days, the culture medium was removed and 50 μls Nano-Glo luciferase substrate (Promega) and 50 μls medium was added to each well. The supernatant (70 μls) was transferred to a microtiter plate and the luminescence was read in an Envision 2103 microplate luminometer (PerkinElmer). Alternatively, the GFP+ cells were quantified by flow cytometry with pacific blue viability dye to exclude dead cells (Biolegend).

Protein Purification.

293F cells (Thermo Fisher) at a density of $2.5\times10^6$ cells/ml were transfected with microbody expression vector plasmid DNA using polyethyleneimine (Polysciences, Inc) at a 1:3 plasm id:PEI ratio. The cells were then cultured at 30° C. and at 12 hours post-transfection 10 mM sodium butyrate was added. After 4 days, the supernatant culture medium was collected, filtered and adjusted pH to 8.0. The medium was passed over a 5 ml HiTrap Chelating column charged with cobalt (GE healthcare), washed with 30 ml of buffer containing 20 mM Tris pH 8, 150 mM NaCl, 10 mM imidazole and the bound protein was eluted in buffer containing 250 mM imidazole. The eluate was concentrated to 1.0 ml and loaded onto a Superdex 200 size-exclusion column (GE healthcare) in running buffer containing 10 mM Tris pH 7.4, 150 mM NaCl. Protein containing fractions were pooled and concentrated. The purified proteins were analyzed on a 4-12% Bis-Tris SDS-PAGE stained with Coomassie blue.

Virion Pull-Down Assay.

293T cells were transfected by lipofection with 4 µg pcACE2-microbody. At 72 hours post-transduction, 0.5 ml of culture supernatant was incubated with nickel-nitrilotri-acetic acid-agarose beads (QIAGEN). The beads were washed, and bound protein was eluted with Laemmle loading buffer. The proteins were analyzed on an immunoblot probed with mouse anti-6×His antibody (Invitrogen) and horseradish peroxidase (HRP)-conjugated goat anti-mouse IgG secondary antibody (Sigma-Aldrich). The proteins were visualized using luminescent substrate and scanned on a LI-COR Biosciences FC Imaging System (LI-COR Biotechnology). Ratios were calculated as the His (spike) signal intensity divided by the p24 signal intensity for an identical exposure of the blot.

Immunoblot Analysis.

Transfected cells were lysed in buffer containing 50 mM HEPES, 150 mM KCl, 2 mM EDTA, 0.5% NP-40, and protease inhibitor cocktail. Protein concentration in the lysates was measured by bicinchoninic protein assay and the lysates (40 µg) were separated by SDS-PAGE. The proteins were transferred to polyvinylidene difluoride membranes and probed with anti-HA mAb (Covance), mouse anti-His mAb (Invitrogen) and anti-GAPDH mAb (Life Technologies) followed by goat anti-mouse HRP-conjugated second antibody (Sigma). The blots were visualized using luminescent substrate (Millipore) on a LI-COR Bio-sciences FC Imaging System.

Binding Assay.

Soluble ACE2 proteins (10 µg) were mixed with 20 µl nickel beads for 1 hour at 4° C. Unbound protein was removed by washing the beads with PBS. The beads were resuspended in PBS and mixed with 40 µl pseudotyped lentiviral virions After 1 h incubation at 4° C., the beads were washed with PBS and resuspended in reducing Laemmli loading buffer and heated to 90° C. The eluted proteins were separated by SDS-PAGE and analyzed on an immunoblot probed with anti-p24 antibody (AG3.0) followed by goat anti-mouse HRP-conjugated second antibody.

Live SARS-CoV-2 Neutralization Assay.

mNeonGreen SARS-CoV-2 (Xie et al., Cell Host and Microbe 2020) was obtained from the World Reference Center for Emerging Viruses and Arboviruses at the University of Texas Medical Branch. The virus was passaged once on Vero E6 cells (ATCC CRL-1586), clarified by low-speed centrifugation, aliquoted, and stored at −80° C. The infectious virus titer was determined by plaque assay on Vero E6 cells after staining with crystal violet. Virus neutralization was determined as previously described (Xie et al, bioRxiv 2020). ACE2.293T cells were seeded in a 96-well plate ($1 \times 10^4$/well). The next day, mNeonGreen SARS-CoV-2 (MOI=0.5) was mixed 1:1 with serially 2-fold diluted soluble ACE2 protein in DMEM/2% FBS and incubated for 1 hour at 37° C. The virus:protein mixture was then added to the ACE2 cells and incubated for 24 hours. at 37° C. in 5% $CO_2$. The cells were fixed with 4% paraformaldehyde, stained with DAPI and the mNeonGreen+ cells were counted on a Celllnsight CX5 Platform high content microscope (Thermo Fisher).

Luciferase Activity Quantification.

To quantify luciferase activity in vivo, mice were injected with 5 µg/g of ACE2 microbody or sACE2-NLuc proteins via intraperitoneal (IP). After 6, 12 hours, 1, 2, 3 days post injection, mice were injected with 100 µL of Nano-Glo substrate (1:40 dilution) via IP injection. After 3 min, mice were imaged by IVIS Lumina III XR (PerkinElmer). Organs were homogenized with a FastPrep-24 5G homogenizer (mpbio) in cold PBS at 10% weight/volume in lysing matrix D tubes (MP Biomedicals). Homogenized tissue supernatant was mixed with the same amount of Nano-Glo Luciferase Assay Reagent (Promega). Then luminescence was quantified on the Envision 2103 Multi-label plate reader (PerkinElmer).

Data Analysis and Statistics.

All experiments were performed in technical duplicates or triplicates and data were analyzed using GraphPad Prism (Version 7 7.0e). Statistical significance was determined by the two-tailed, unpaired t test. Significance was based on two-sided testing and attributed to $p < 0.05$. Confidence intervals are shown as the mean±SD or SEM. (*$P \leq 0.05$, $P \leq 0.01$, *$P \leq 0.001$, ****$P \leq 0.0001$).

Discussion of Examples

It will be recognized from the foregoing description, examples, and figures, the present disclosure provides an improved soluble form of ACE2 that potently blocks SARS-CoV-2 entry. The protein contains of the ectodomain of ACE2 fused to a single domain of the IgG heavy chain Fc, rendering it smaller than those fused to the full-length Fc domain and potentially providing an increased half-life in vivo (Maute, Gordon et al. 2015). The microbody protein is a disulfide-bonded dimer in contrast to soluble ACE2 lacking the Fc domain which was dimeric but not nondisulfide-bonded. While both proteins are dimeric, the ACE2 microbody had about 10-fold more antiviral activity than soluble ACE2 and bound to virions with a >4-fold increased affinity. While high affinity anti-spike protein monoclonal antibodies that potently inhibit SARS-CoV-2 infection will be of great value in the treatment of COVID-19, the soluble receptor proteins have advantageous features. The ACE2 microbody is of fully human origin so should be relatively non-immunogenic. In addition, it is expected to be broadly active against mutated variant spike proteins that may arise in the human and non-human animal populations. The microbody was fully active against virus with the D614G variant S protein which has been shown to increase SARS-CoV-2 infectivity (FIG. 6) and was active against ACE2-specific S proteins from other β coronaviruses. The H345A mutation of one of the histidines that is essential for ACE2 catalytic activity did not impair S protein binding. In several analyses, the H345A.ACE2 microbody appeared more active than the wild-type protein, although it was uncertain whether this difference was significant as the two proteins had similar activity in some experiments, including in the live virus replication assay. Because of the role of ACE2 in blood pressure regulation, the mutation serves to decrease biohazard associated with its use therapeutically.

Escape from inhibition studies provided insight into the kinetics of virus infection and into the mechanism of inhibition by the soluble receptors. Pretreatment of virus with the ACE2 microbody potently neutralized the virus as did simultaneous treatment addition of virus and microbody to cells. Furthermore, the protein retained its ability to prevent infection even when added to the culture at times after addition of virus, blocking infection by about 50% when added 1 hour after virus addition. The ACE2 microbody was partially active even on virus that had already attached to the cell. When virus was pre-bound for 2 hours, a time at which about 10% of the infectious virus had bound the cell, the ACE2 microbody retained the ability to prevent infection of about 50% of the bound virus (FIG. 5A). Taken together, the experiments suggest a series of events in which the virus binds to cells over a period of about 4 hours. During this time, the ACE2 microbody is highly efficient, neutralizing nearly all of the free virus. Once the virus binds to the cell, the ACE2 microbody retains its ability to block infection for about 30 min, suggesting that binding is initially through a small number of S proteins and that over 2 hours. Additional S proteins are recruited to interact with target cells ACE2, a period in which the ACE2 microbody is remains able to block the fusion reaction. Once a sufficient number of S protein:ACE2 interactions form, the virus escapes neutralization.

It was surprising that the ACE2 microbody had more antiviral activity than soluble ACE2 as both proteins are dimeric. The ACE2 microbody protein also showed somewhat better binding to virions than soluble ACE2. The reasons for these differences are not clear. It is possible that the disulfide bonds of the ACE2 microbody stabilize the dimer or that they position the individual monomers in a more favorable conformation to bind to the individual subunits of the S protein trimer. In most of the experiments of this disclosure we used ACE2.293 cells that overexpress ACE2 compared to all of the other cell-lines tested. On untransfected 293 cells that express barely detectable levels of ACE2, the antiviral activity of the microbody protein was increased, suggesting that the antiviral activity of the ACE2 microbody may be under-estimated by the use of ACE2 over-expressing cells.

Recent reports have described similar soluble ACE2 proteins. Recently soluble ACE2-related inhibitor including rhACE2 was shown to partially block the infection (Case, Rothlauf et al. 2020, Lei, Qian et al. 2020, Monteil, Kwon et al. 2020), they proteins had limited clinical use due to their short half-life (Wysocki, Ye et al. 2010) (<2 hours in mouse). The dimeric rACE2-Fc had a half-life in mice plasma that was over 1 week (Liu, Wysocki et al. 2018). Measurement of the half-life of the ACE2 microbody showed that the protein retained antiviral activity over several days, significantly longer than soluble ACE2 (FIG. 14).

The phenomenon of antibody-dependent enhancement is caused by the interaction of the Fc domain of non-neutralizing antibody with the Fc receptor on cells which then serves to promote rather than inhibit virus neutralization. A similar phenomenon is possible with receptor-Fc fusion proteins by interaction with Fc receptor on cells. Because the ACE2 microbody contained only a single Fc domain, it was not expected to interact with Fc receptor. To test whether this was the case, we tested the ACE2 microbody in an enhancement assay using U937 cells which express Fc receptors. The ACE2 microbody protein did not detectably bind to cells that express the Fc γ receptor and the cells did not become infected, suggesting that this mechanism is not likely to play a role in vivo (FIG. 15 and not shown).

Pseudotyped viruses have been extremely useful for studies of SARS-CoV-2 entry. Vectors for producing SARS-CoV-2 lentiviral pseudotypes have been developed by several laboratories. The vectors described herein produce pseudotyped lentiviral viruses with very high infectivity. The high infectivity of the pseudotypes produced is due in part to efficient expression of a codon-optimized Δ19 S protein and the efficient virion incorporation that results from the cytoplasmic tail truncation. The Δ19 S protein was present at only slightly higher levels on the cell surface than the full-length protein, suggesting that this small increase does not fully account for the large increase in virion incorporation. A possible explanation is that the full-length cytoplasmic tail sterically hinders virion incorporation by conflicting with the underlying viral matrix protein and that the deletion removes the conflict. Also, contributing to high viral titers, is the use of separate Gag/Pol packaging vector and lentiviral transfer vector as opposed to a lentiviral proviral DNA encoding Gag/Pol and the reporter gene, a strategy that resulted in higher reporter gene expression as shown in a direct comparison (not shown). Moreover, the dual luciferase/GFP reporter allows for measurement of infectious virus titer by flow cytometry and the high sensitivity of nanoluciferase read-out.

A feature of soluble receptors is that because the virus spike protein needs to conserve receptor binding affinity to maintain transmissibility, they should maintain their ability to neutralize S protein variants. SARS-CoV-2 S variants have been found to be circulating in the human population and it is likely that others are yet to emerge, some of which may be less sensitive to neutralization by the therapeutic monoclonal antibodies currently under development. The recently identified virus variant encoding a D614G S protein has been found to be spreading with increased frequency in the human population (Daniloski, Guo et al. 2020, Eaaswarkhanth, Al Madhoun et al. 2020, Korber, Fischer et al. 2020, Zhang, Jackson et al. 2020). The D614G S protein was shown to be more stable and to increase virion infectivity. Data in this disclosure confirms the increased infectivity of virions and that the D614G S protein has a higher affinity for ACE2 as measured in a virion binding assay. Nevertheless, the ACE2 microbody maintained its ability to neutralize D614G S pseudotyped virus. The ability of the ACE2 microbody to neutralize a panel of β coronaviruses suggest that it may also be able to neutralize novel ACE2 using coronaviruses that may be transferred to the human population in the future (FIG. 8). Thus, the microbody protein could serve as an off-the-shelf reagent that could be rapidly deployed.

TABLE 1

| Constructs | primer sequence (5'-3') | Reverse primer sequence (5'-3') |
|---|---|---|
| S fragment A | CGGTATGGTACCCCACCATG TTCGTGTTTCTGGTGCTGCTG (SEQ ID NO: 7) | CGTCGACGATGAATTCGACA GCCG (SEQ ID NO: 8) |
| S fragment B | GGCAGCAATGGAATTCTGTTT CAG (SEQ ID NO: 9) | TACGCTGACGCTCGAGTTAG GCGTAG (SEQ ID NO: 10) |
| pvCoV2-S Δ19-no tag | CGGTATGGTACCCCACCATG TTCGTGTTTCTGGTGCTGCT (SEQ ID NO: 11) | GGCTATCTCGAGTTAGCAGCA GGAGCCACAGCTACAGCAGC (SEQ ID NO: 12) |

TABLE 1-continued

| Constructs | primer sequence (5'-3') | Reverse primer sequence (5'-3') |
|---|---|---|
| pcCoV2-S Δ19-HA | CGGTATGGTACCCCACCATG TTCGTGTTTCTGGTGCTGCT (SEQ ID NO: 13) | GGCTATCTCGAGTTAAGCGTA GTCTGGGACGTCGTATGGGT AGCAGCAGGAGCCACAGCTA CAGCAGC (SEQ ID NO: 14) |
| pcCoV2-S D614G Δ19-no tag | CGGTATGGTACCCCACCATG TTCGTGTTTCTGGTGCTGCT (SEQ ID NO: 15) | GGCTATCTCGAGTTATGTGTA ATGTAATTTGACTCCTTTG (SEQ ID NO: 16) |
| pcCoV2-S D614G Δ19-no tag inner | CAGGTGGCAGTGCTGTACCA GGGTGTGAACTGTACCGAAG TGCCCG (SEQ ID NO: 17) | CGGGCACTTCGGTACAGTTC ACACCCTGGTACAGCACTGC CACCTG (SEQ ID NO: 18) |
| pcCoV2-S D614G Δ19-HA tag | CGGTATGGTACCCCACCATG TTCGTGTTTCTGGTGCTGCT (SEQ ID NO: 19) | GGCTATCTCGAGTTAAGCGTA GTCTGGGACGTCGTATGGGT AGCAGCAGGAGCCACAGCTA CAGCAGC (SEQ ID NO: 20) |
| pcCoV2-S D614G Δ19-HA tag inner | CAGGTGGCAGTGCTGTACCA GGGTGTGAACTGTACCGAAG TGCCCG (SEQ ID NO: 21) | CGGGCACTTCGGTACAGTTC ACACCCTGGTACAGCACTGC CACCTG (SEQ ID NO: 22) |
| plenti.ACE2-HA | CGGTATTCTAGACCACCATGT CAAGCTCTTCCTGGCTCCTTC (SEQ ID NO: 23) | GGCTATGTCGACCTAAGCGTA GTCTGGGACGTCGTATGGGT AAAAGGAGGTCTGAACATCAT CAGTG (SEQ ID NO: 24) |
| ACE2 microbody | CGGTATGGTACCCCACCATG TCAAGCTCTTCCTGGCTCCTT C (SEQ ID NO: 25) | GGCTATCTCGAGTCAGTGATG GTGGTGATGGTGATGATGGG AAACAGGGGGCTGGTTAGGA GGTCC (SEQ ID NO: 26) |
| ACE2 microbody inner | AGTTTTGTCACAAGATTTGGG CTCGGAAACAGGGGGCTGGT TAGGAGGTC (SEQ ID NO: 27) | GACCTCCTAACCAGCCCCCT GTTTCCGAGCCCAAATCTTGT GACAAAACT (SEQ ID NO: 28) |
| ACE2.H345A microbody | CGGTATGGTACCCCACCATG TCAAGCTCTTCCTGGCTCCTT C (SEQ ID NO: 29) | GGCTATCTCGAGTCAGTGATG GTGGTGATGGTGATGATGGG AAACAGGGGGCTGGTTAGGA GGTCC (SEQ ID NO: 30) |
| ACE2.H345A microbody inner | GGAAATGTTCAGAAAGCAGT CTGCGCTCCCACAGCTTGGG (SEQ ID NO: 31) | CCCAAGCTGTGGGAGCGCAG ACTGCTTTCTGAACATTTCC (SEQ ID NO: 32) |
| Soluble ACE2 | CGGTATGGTACCCCACCATG TCAAGCTCTTCCTGGCTCCTT C (SEQ ID NO: 33) | GGCTATCTCGAGTCAGTGATG GTGGTGATGGTGATG (SEQ ID NO: 34) |
| GFP-nLuc | CGGTATGGATCCCCACCATG GTGAGCAAGG (SEQ ID NO: 35) | GGCTATGTCGACTTACGCCA GAATGCG (SEQ ID NO: 36) |
| GFP-nLuc inner | GCCTGCTGAAGCAGGCTGGA GACGTGGAGGAGAACCCTGG ACCTGTCTTCACACTCGAAG (SEQ ID NO: 37) | CAGCCTGCTTCAGCAGGCTG AAGTTAGTAGCTCCGCTTCCC TTGTACAGCTCGTCCATGC (SEQ ID NO: 38) |

TABLE 2

| | |
|---|---|
| S fragment A (cDNA) | CGATGCTCACGGATCCGCCACCATGTTCGTGTTTCTGGTGCTGCTGCCTCTG GTGTCCAGCCAGTGTGTGAACCTGACCACCAGAACACAGCTGCCTCCAGCCT ACACCAACAGCTTTACCAGAGGCGTGTACTACCCCGACAAGGTGTTCAGATC CAGCGTGCTGCACTCTACCCAGGACCTGTTCCTGCCTTTCTTCAGCAACGTG ACCTGGTTCCACGCCATCCACGTGTCCGGCACCAATGGCACCAAGAGATTCG ACAACCCCGTGCTGCCCTTCAACGACGGGGTGTACTTTGCCAGCACCGAGAA GTCCAACATCATCAGAGGCTGGATCTTCGGCACCACACTGGACAGCAAGACC CAGAGCCTGCTGATCGTGAACAACGCCACCAACGTGGTCATCAAAGTGTGCG AGTTCCAGTTCTGCAACGACCCCTTCCTGGGCGTCTACTACCACAAGAACAA CAAGAGCTGGATGGAAAGCGAGTTCCGGGTGTACAGCAGCGCCAACAACTG CACCTTCGAGTACGTGTCCCAGCCTTTCCTGATGGACCTGGAAGGCAAGCAG GGCAACTTCAAGAACCTGCGCGAGTTCGTGTTCAAGAACATCGACGGCTACT TCAAGATCTACAGCAAGCACACCCCTATCAACCTCGTGCGGGATCTGCCTCA GGGCTTCTCTGCTCTGGAACCCCTGGTGGATCTGCCCATCGGCATCAACATC ACCCGGTTTCAGACACTGCTGGCCCTGCACAGAAGCTACCTGACACCTGGCG |

TABLE 2-continued

| | |
|---|---|
| | ATAGCAGCAGCGGATGGACAGCTGGTGCCGCCGCTTACTATGTGGGCTACC<br>TGCAGCCTAGAACCTTCCTGCTGAAGTACAACGAGAACGGCACCATCACCGA<br>CGCCGTGGATTGTGCTCTGGATCCTCTGAGCGAGACAAAGTGCACCCTGAAG<br>TCCTTCACCGTGGAAAAGGGCATCTACCAGACCAGCAACTTCCGGGTGCAGC<br>CCACCGAATCCATCGTGCGGTTCCCCAATATCACCAATCTGTGCCCCTTCGG<br>CGAGGTGTTCAATGCCACCAGATTCGCCTCTGTGTACGCCTGGAACCGGAAG<br>CGGATCAGCAATTGCGTGGCCGACTACTCCGTGCTGTACAACTCCGCCAGCT<br>TCAGCACCTTCAAGTGCTACGGCGTGTCCCCTACCAAGCTGAACGACCTGTG<br>CTTCACAAACGTGTACGCCGACAGCTTCGTGATCCGGGGAGATGAAGTGCG<br>GCAGATTGCCCCTGGACAGACAGGCAAGATCGCCGACTACAACTACAAGCTG<br>CCCGACGACTTCACCGGCTGTGTGATTGCCTGGAACAGCAACAACCTGGACT<br>CCAAAGTCGGCGGCAACTACAATTACCTGTACCGGCTGTTCCGGAAGTCCAA<br>TCTGAAGCCCTTCGAGCGGGACATCTCCACCGAGATCTATCAGGCCGGCAG<br>CACCCCTTGTAACGGCGTGGAAGGCTTCAACTGCTACTTCCCACTGCAGTCC<br>TACGGCTTTCAGCCCACAAATGGCGTGGGCTATCAGCCCTACAGAGTGGTGG<br>TGCTGAGCTTCGAACTGCTGCATGCCCCTGCCACAGTGTGCGGCCCTAAGAA<br>AAGCACCAATCTCGTGAAGAACAAATGCGTGAACTTCAACTTCAACGGCCTGA<br>CCGGCACCGGCGTGCTGACAGAGAGCAACAAGAAGTTCCTGCCATTCCAGC<br>AGTTTGGCCGGGATATCGCCGATACCACAGACGCCGTTAGAGATCCCCAGAC<br>ACTGGAAATCCTGGACATCACCCCTTGCAGCTTCGGCGGAGTGTCTGTGATC<br>ACCCCTGGCACCAACACCAGCAATCAGGTGGCAGTGCTGTACCAGGACGTG<br>AACTGTACCGAAGTGCCCGTGGCCATTCACGCCGATCAGCTGACACCTACAT<br>GGCGGGTGTACTCCACCGGCTCCAATGTGTTTCAAACGCGTGCCGGCTGTC<br>GAATTCATCGTCGACG<br>(SEQ ID NO: 39) |
| S fragment B<br>(cDNA) | GGCAGCAATGGAATTCTGTTTCAGACGCGTGCCGGCTGCCTGATTGGAGCC<br>GAACACGTGAACAACAGCTACGAGTGCGACATCCCTATCGGAGCCGGCATCT<br>GTGCCAGCTACCAGACACAGACAAACAGCCCCAGACGGGCCAGATCTGTGG<br>CCAGCCAGAGCATCATTGCCTACACCATGTCTCTGGGCGCCGAGAACAGCGT<br>GGCCTACAGCAACAACTCTATCGCTATCCCCACCAACTTCACCATCAGCGTG<br>ACCACCGAGATCCTGCCTGTGTCCATGACCAAGACCAGCGTGGACTGCACCA<br>TGTACATCTGCGGCGATAGCACCGAGTGCAGCAACCTGCTGCTGCAGTACG<br>GCAGCTTCTGCACCCAGCTGAATAGAGCCCTGACCGGAATCGCCGTGGAAC<br>AGGACAAGAACACCCAAGAGGTGTTCGCCCAAGTGAAGCAGATCTACAAGAC<br>CCCTCCTATCAAGGACTTCGGCGGCTTCAACTTCAGCCAGATTCTGCCCGAT<br>CCTAGCAAGCCCAGCAAGCGGAGCTTCATCGAGGACCTGCTGTTCAACAAAG<br>TGACCCTGGCCGACGCCGGCTTCATCAAGCAGTATGGCGATTGCCTGGGCG<br>ACATTGCCGCCAGGGATCTGATTTGCGCCCAGAAGTTTAACGGCCTGACCGT<br>GCTGCCTCCTCTGCTGACCGATGAGATGATCGCCCAGTACACATCTGCCCTG<br>CTGGCCGGCACAATCACAAGCGGCTGGACATTTGGAGCTGGCGCCGCTCTG<br>CAGATCCCCTTTGCTATGCAGATGGCCTACCGGTTCAACGGCATCGGCGTGA<br>CCCAGAACGTGCTGTACGAGAACCAGAAGCTGATCGCCAACCAGTTCAACAG<br>CGCCATCGGCAAGATCCAGGACAGCCTGAGCAGTACAGCCAGCGCTCTGGG<br>AAAGCTGCAGGACGTGGTCAACCAGAATGCCCAGGCTCTGAACACCCTGGTC<br>AAGCAGCTGAGCAGCAACTTCGGCGCCATCAGCAGCGTGCTGAACGACATC<br>CTGAGCCGCCTGGATAAGGTGGAAGCCGAGGTGCAGATCGACCGGCTGATT<br>ACAGGCAGACTGCAGAGCCTGCAGACCTACGTGACACAGCAGCTGATCAGA<br>GCCGCCGAGATTAGAGCCTCTGCCAATCTGGCCGCCACCAAGATGTCTGAGT<br>GTGTGCTGGGCCAGAGCAAGAGAGTGGACTTTTGCGGCAAGGGCTACCACC<br>TGATGAGCTTCCCTCAGTCTGCTCCTCACGGCGTGGTGTTTCTGCACGTGAC<br>ATACGTGCCCGCTCAAGAGAAGAATTTCACCACCGCTCCAGCCATCTGCCAC<br>GACGGCAAAGCCCACTTTCCTAGAGAAGGCGTGTTCGTGTCCAACGGCACCC<br>ATTGGTTCGTGACTCAGCGGAACTTCTACGAGCCCCAGATCATCACCACCGA<br>CAACACCTTCGTGTCCGGCAACTGCGACGTCGTGATCGGCATCGTGAACAAT<br>ACCGTGTACGACCCTCTGCAGCCCGAGCTGGACAGCTTCAAAGAGGAACTG<br>GACAAGTACTTCAAGAACCACACAAGCCCCGACGTGGACCTGGGCGATATCA<br>GCGGAATCAATGCCAGCGTCGTGAACATCCAGAAAGAGATCGACAGACTGAA<br>CGAGGTGGCCAAGAACCTGAACGAGAGCCTGATCGACCTGCAAGAGCTGGG<br>GAAGTACGAGCAGTATATCAAGTGGCCCTGGTACATCTGGCTGGGCTTTATC<br>GCCGGCCTGATTGCCATCGTGATGGTCACAATCATGCTGTGCTGCATGACCA<br>GCTGTTGCAGCTGCCTGAAGGGCTGCTGTAGCTGTGGCTCCTGCTGCAAGTT<br>CGACGAGGACGATTCTGAGCCCGTGCTGAAGGGCGTGAAGCTGCACTACAC<br>ATACCCCTACGACGTGCCCGACTACGCCTAACTCGAGCGTCAGCGTA (SEQ ID NO: 40) |
| ACE2<br>(cDNA) | ATGTCAAGCTCTTCCTGGCTCCTTCTCAGCCTTGTTGCTGTAACTGCTGCTCA<br>GTCCACCATTGAGGAACAGGCCAAGACATTTTTGGACAAGTTTAACCACGAA<br>GCCGAAGACCTGTTCTATCAAAGTTCACTTGCTTCTTGGAATTATAACACCAAT<br>ATTACTGAAGAGAATGTCCAAAACATGAATAATGCTGGGGACAAATGGTCTGC<br>CTTTTTAAAGGAACAGTCCACACTTGCCCAAATGTATCCACTACAAGAAATTCA<br>GAATCTCACAGTCAAGCTTCAGCTGCAGGCTCTTCAGCAAAATGGGTCTTCA<br>GTGCTCTCAGAAGACAAGAGCAAACGGTTGAACACAATTCTAAATACAATGAG<br>CACCATCTACAGTACTGGAAAAGTTTGTAACCCAGATAATCCACAAGAATGCT<br>TATTACTTGAACCAGGTTTGAATGAAATAATGGCAAACAGTTTAGACTACAATG<br>AGAGGCTCTGGGCTTGGGAAAGCTGGAGATCTGAGGTCGGCAAGCAGCTGA<br>GGCCATTATATGAAGAGTATGTGGTCTTGAAAAATGAGATGGCAAGAGCAAAT<br>CATTATGAGGACTATGGGGATTATTGGAGAGGAGACTATGAAGTAAATGGGG<br>TAGATGGCTATGACTACAGCCGCGGCCAGTTGATTGAAGATGTGGAACATAC<br>CTTTGAAGAGATTAAACCATTATATGAACATCTTCATGCCTATGTGAGGGCAA |

TABLE 2-continued

```
AGTTGATGAATGCCTATCCTTCCTATATCAGTCCAATTGGATGCCTCCCTGCT
CATTTGCTTGGTGATATGTGGGGTAGATTTTGGACAAATCTGTACTCTTTGAC
AGTTCCCTTTGGACAGAAACCAAACATAGATGTTACTGATGCAATGGTGGACC
AGGCCTGGGATGCACAGAGAATATTCAAGGAGGCCGAGAAGTTCTTTGTATC
TGTTGGTCTTCCTAATATGACTCAAGGATTCTGGGAAAATTCCATGCTAACGG
ACCCAGGAAATGTTCAGAAAGCAGTCTGCCATCCCACAGCTTGGGACCTGGG
GAAGGGCGACTTCAGGATCCTTATGTGCACAAAGGTGACAATGGACGACTTC
CTGACAGCTCATCATGAGATGGGGCATATCCAGTATGATATGGCATATGCTG
CACAACCTTTTCTGCTAAGAAATGGAGCTAATGAAGGATTCCATGAAGCTGTT
GGGGAAATCATGTCACTTTCTGCAGCCACACCTAAGCATTTAAAATCCATTGG
TCTTCTGTCACCCGATTTTCAAGAAGACAATGAAACAGAAATAAACTTCCTGCT
CAAACAAGCACTCACGATTGTTGGGACTCTGCCATTTACTTACATGTTAGAGA
AGTGGAGGTGGATGGTCTTTAAAGGGGAAATTCCCAAAGACCAGTGGATGAA
AAAGTGGTGGGAGATGAAGCGAGAGATAGTTGGGGTGGTGGAACCTGTGCC
CCATGATGAAACATACTGTGACCCCGCATCTCTGTTCCATGTTTCTAATGATTA
CTCATTCATTCGATATTACACAAGGACCCTTTACCAATTCCAGTTTCAAGAAGC
ACTTTGTCAAGCAGCTAAACATGAAGGCCCTCTGCACAAATGTGACATCTCAA
ACTCTACAGAAGCTGGACAGAAACTGTTCAATATGCTGAGGCTTGGAAAATCA
GAACCCTGGACCCTAGCATTGGAAAATGTTGTAGGAGCAAAGAACATGAATG
TAAGGCCACTGCTCAACTACTTTGAGCCCTTATTTACCTGGCTGAAAGACCAG
AACAAGAATTCTTTTGTGGGATGGAGTACCGACTGGAGTCCATATGACGACC
AAAGCATCAAAGTGAGGATAAGCCTAAAATCAGCTCTTGGAGATAAAGCATAT
GAATGGAACGACAATGAAATGTACCTGTTCCGATCATCTGTTGCATATGCTAT
GAGGCAGTACTTTTTAAAAGTAAAAAATCAGATGATTCTTTTTGGGGAGGAGG
ATGTGCGAGTGGCTAATTTGAAACCAAGAATCTCCTTTAATTTCTTTGTCACTG
CACCTAAAAATGTGTCTGATATCATTCCTAGAACTGAAGTTGAAAAGGCCATC
AGGATGTCCCGGAGCCGTATCAATGATGCTTTCCGTCTGAATGACAACAGCC
TAGAGTTTCTGGGGATACAGCCAACACTTGGACCTCCTAACCAGCCCCCTGT
TTCCATATGGCTGATTGTTTTGGAGTTGTGATGGGAGTGATAGTGGTTGGCA
TTGTCATCCTGATCTTCACTGGGATCAGAGATCGGAAGAAGAAAATAAAGCA
AGAAGTGGAGAAAATCCTTATGCCTCCATCGATATTAGCAAAGGAGAAAATAA
TCCAGGATTCCAAAACACTGATGATGTTCAGACCTCCTTTTAG (SEQ ID NO: 41)
```

TABLE 3

| | |
|---|---|
| SARS-COV-2 S-HA (amino acid) | MFVFLVLLPLVSSQCVNLTTRTQLPPAYTNSFTRGVYYPDKVFRSSVLHST QDLFLPFFSNVTWFHAIHVSGTNGTKRFDNPVLPFNDGVYFASTEKSNIIRG WIFGTTLDSKTQSLLIVNNATNVVIKVCEFQFCNDPFLGVYYHKNNKSWME SEFRVYSSANNCTFEYVSQPFLMDLEGKQGNFKNLREFVFKNIDGYFKIYS KHTPINLVRDLPQGFSALEPLVDLPIGINITRFQTLLALHRSYLTPGDSSSGW TAGAAAYYVGYLQPRTFLLKYNENGTITDAVDCALDPLSETKCTLKSFTVEK GIYQTSNFRVQPTESIVRFPNITNLCPFGEVFNATRFASVYAWNRKRISNCV ADYSVLYNSASFSTFKCYGVSPTKLNDLCFTNVYADSFVIRGDEVRQIAPG QTGKIADYNYKLPDDFTGCVIAWNSNNLDSKVGGNYNYLYRLFRKSNLKPF ERDISTEIYQAGSTPCNGVEGFNCYFPLQSYGFQPTNGVGYQPYRVVVLS FELLHAPATVCGPKKSTNLVKNKCVNFNFNGLTGTGVLTESNKKFLPFQQF GRDIADTTDAVRDPQTLEILDITPCSFGGVSVITPGTNTSNQVAVLYQDVNC TEVPVAIHADQLTPTWRVYSTGSNVFQTRAGCLIGAEHVNNSYECDIPIGA GICASYQTQTNSPRRARSVASQSIIAYTMSLGAENSVAYSNNSIAIPTNFTIS VTTEILPVSMTKTSVDCTMYICGDSTECSNLLLQYGSFCTQLNRALTGIAVE QDKNTQEVFAQVKQIYKTPPIKDFGGFNFSQILPDPSKPSKRSFIEDLLFNK VTLADAGFIKQYGDCLGDIAARDLICAQKFNGLTVLPPLLTDEMIAQYTSALL AGTITSGWTFGAGAALQIPFAMQMAYRFNGIGVTQNVLYENQKLIANQFNS AIGKIQDSLSSTASALGKLQDVVNQNAQALNTLVKQLSSNFGAISSVLNDILS RLDKVEAEVQIDRLITGRLQSLQTYVTQQLIRAAEIRASANLAATKMSECVL GQSKRVDFCGKGYHLMSFPQSAPHGVVFLHVTYVPAQEKNFTTAPAICHD GKAHFPREGVFVSNGTHWFVTQRNFYEPQIITTDNTFVSGNCDVVIGIVNN TVYDPLQPELDSFKEELDKYFKNHTSPDVDLGDISGINASVVNIQKEIDRLN EVAKNLNESLIDLQELGKYEQYIKWPWYIWLGFIAGLIAIVMVTIMLCCMTSC CSCLKGCCSCGSCCKFDEDDSEPVLKGVKLHYTPYDVPDYA (SEQ ID NO: 42) |
| SARS-COV-2 Δ19 S (amino acid) | MFVFLVLLPLVSSQCVNLTTRTQLPPAYTNSFTRGVYYPDKVFRSSVLHST QDLFLPFFSNVTWFHAIHVSGTNGTKRFDNPVLPFNDGVYFASTEKSNIIRG WIFGTTLDSKTQSLLIVNNATNVVIKVCEFQFCNDPFLGVYYHKNNKSWME SEFRVYSSANNCTFEYVSQPFLMDLEGKQGNFKNLREFVFKNIDGYFKIYS KHTPINLVRDLPQGFSALEPLVDLPIGINITRFQTLLALHRSYLTPGDSSSGW TAGAAAYYVGYLQPRTFLLKYNENGTITDAVDCALDPLSETKCTLKSFTVEK GIYQTSNFRVQPTESIVRFPNITNLCPFGEVFNATRFASVYAWNRKRISNCV ADYSVLYNSASFSTFKCYGVSPTKLNDLCFTNVYADSFVIRGDEVRQIAPG QTGKIADYNYKLPDDFTGCVIAWNSNNLDSKVGGNYNYLYRLFRKSNLKPF ERDISTEIYQAGSTPCNGVEGFNCYFPLQSYGFQPTNGVGYQPYRVVVLS FELLHAPATVCGPKKSTNLVKNKCVNFNFNGLTGTGVLTESNKKFLPFQQF GRDIADTTDAVRDPQTLEILDITPCSFGGVSVITPGTNTSNQVAVLYQDVNC TEVPVAIHADQLTPTWRVYSTGSNVFQTRAGCLIGAEHVNNSYECDIPIGA GICASYQTQTNSPRRARSVASQSIIAYTMSLGAENSVAYSNNSIAIPTNFTIS VTTEILPVSMTKTSVDCTMYICGDSTECSNLLLQYGSFCTQLNRALTGIAVE |

TABLE 3-continued

|  |  |
|---|---|
|  | QDKNTQEVFAQVKQIYKTPPIKDFGGFNFSQILPDPSKPSKRSFIEDLLFNK<br>VTLADAGFIKQYGDCLGDIAARDLICAQKFNGLTVLPPLLTDEMIAQYTSALL<br>AGTITSGWTFGAGAALQIPFAMQMAYRFNGIGVTQNVLYENQKLIANQFNS<br>AIGKIQDSLSSTASALGKLQDVVNQNAQALNTLVKQLSSNFGAISSVLNDILS<br>RLDKVEAEVQIDRLITGRLQSLQTYVTQQLIRAAEIRASANLAATKMSECVL<br>GQSKRVDFCGKGYHLMSFPQSAPHGVVFLHVTYVPAQEKNFTTAPAICHD<br>GKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLN<br>EVAKNLNESLIDLQELGKYEQYIKWPWYIWLGFIAGLIAIVMVTIMLCCMTSC<br>CSCLKGCCSCGSCC (SEQ ID NO: 43) |
| SARS-COV-2 Δ19 S-<br>HA<br>(amino acid) | MFVFLVLLPLVSSQCVNLTTRTQLPPAYTNSFTRGVYYPDKVFRSSVLHST<br>QDLFLPFFSNVTWFHAIHVSGTNGTKRFDNPVLPFNDGVYFASTEKSNIIRG<br>WIFGTTLDSKTQSLLIVNNATNVVIKVCEFQFCNDPFLGVYYHKNNKSWME<br>SEFRVYSSANNCTFEYVSQPFLMDLEGKQGNFKNLREFVFKNIDGYFKIYS<br>KHTPINLVRDLPQGFSALEPLVDLPIGINITRFQTLLALHRSYLTPGDSSSGW<br>TAGAAAYYVGYLQPRTFLLKYNENGTITDAVDCALDPLSETKCTLKSFTVEK<br>GIYQTSNFRVQPTESIVRFPNITNLCPFGEVFNATRFASVYAWNRKRISNCV<br>ADYSVLYNSASFSTFKCYGVSPTKLNDLCFTNVYADSFVIRGDEVRQIAPG<br>QTGKIADYNYKLPDDFTGCVIAWNSNNLDSKVGGNYNYLYRLFRKSNLKPF<br>ERDISTEIYQAGSTPCNGVEGFNCYFPLQSYGFQPTNGVGYQPYRVVVLS<br>FELLHAPATVCGPKKSTNLVKNKCVNFNFNGLTGTGVLTESNKKFLPFQQF<br>GRDIADTTDAVRDPQTLEILDITPCSFGGVSVITPGTNTSNQVAVLYQDVNC<br>TEVPVAIHADQLTPTWRVYSTGSNVFQTRAGCLIGAEHVNNSYECDIPIGA<br>GICASYQTQTNSPRRARSVASQSIIAYTMSLGAENSVAYSNNSIAIPTNFTIS<br>VTTEILPVSMTKTSVDCTMYICGDSTECSNLLLQYGSFCTQLNRALTGIAVE<br>QDKNTQEVFAQVKQIYKTPPIKDFGGFNFSQILPDPSKPSKRSFIEDLLFNK<br>VTLADAGFIKQYGDCLGDIAARDLICAQKFNGLTVLPPLLTDEMIAQYTSALL<br>AGTITSGWTFGAGAALQIPFAMQMAYRFNGIGVTQNVLYENQKLIANQFNS<br>AIGKIQDSLSSTASALGKLQDVVNQNAQALNTLVKQLSSNFGAISSVLNDILS<br>RLDKVEAEVQIDRLITGRLQSLQTYVTQQLIRAAEIRASANLAATKMSECVL<br>GQSKRVDFCGKGYHLMSFPQSAPHGVVFLHVTYVPAQEKNFTTAPAICHD<br>GKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLN<br>EVAKNLNESLIDLQELGKYEQYIKWPWYIWLGFIAGLIAIVMVTIMLCCMTSC<br>CSCLKGCCSCGSCCYPYDVPDYA (SEQ ID NO: 44) |
| SARS- COV-2 D614G<br>Δ19 S<br>(amino acid) | MFVFLVLLPLVSSQCVNLTTRTQLPPAYTNSFTRGVYYPDKVFRSSVLHST<br>QDLFLPFFSNVTWFHAIHVSGTNGTKRFDNPVLPFNDGVYFASTEKSNIIRG<br>WIFGTTLDSKTQSLLIVNNATNVVIKVCEFQFCNDPFLGVYYHKNNKSWME<br>SEFRVYSSANNCTFEYVSQPFLMDLEGKQGNFKNLREFVFKNIDGYFKIYS<br>KHTPINLVRDLPQGFSALEPLVDLPIGINITRFQTLLALHRSYLTPGDSSSGW<br>TAGAAAYYVGYLQPRTFLLKYNENGTITDAVDCALDPLSETKCTLKSFTVEK<br>GIYQTSNFRVQPTESIVRFPNITNLCPFGEVFNATRFASVYAWNRKRISNCV<br>ADYSVLYNSASFSTFKCYGVSPTKLNDLCFTNVYADSFVIRGDEVRQIAPG<br>QTGKIADYNYKLPDDFTGCVIAWNSNNLDSKVGGNYNYLYRLFRKSNLKPF<br>ERDISTEIYQAGSTPCNGVEGFNCYFPLQSYGFQPTNGVGYQPYRVVVLS<br>FELLHAPATVCGPKKSTNLVKNKCVNFNFNGLTGTGVLTESNKKFLPFQQF<br>GRDIADTTDAVRDPQTLEILDITPCSFGGVSVITPGTNTSNQVAVLYQGVNC<br>TEVPVAIHADQLTPTWRVYSTGSNVFQTRAGCLIGAEHVNNSYECDIPIGA<br>GICASYQTQTNSPRRARSVASQSIIAYTMSLGAENSVAYSNNSIAIPTNFTIS<br>VTTEILPVSMTKTSVDCTMYICGDSTECSNLLLQYGSFCTQLNRALTGIAVE<br>QDKNTQEVFAQVKQIYKTPPIKDFGGFNFSQILPDPSKPSKRSFIEDLLFNK<br>VTLADAGFIKQYGDCLGDIAARDLICAQKFNGLTVLPPLLTDEMIAQYTSALL<br>AGTITSGWTFGAGAALQIPFAMQMAYRFNGIGVTQNVLYENQKLIANQFNS<br>AIGKIQDSLSSTASALGKLQDVVNQNAQALNTLVKQLSSNFGAISSVLNDILS<br>RLDKVEAEVQIDRLITGRLQSLQTYVTQQLIRAAEIRASANLAATKMSECVL<br>GQSKRVDFCGKGYHLMSFPQSAPHGVVFLHVTYVPAQEKNFTTAPAICHD<br>GKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLN<br>EVAKNLNESLIDLQELGKYEQYIKWPWYIWLGFIAGLIAIVMVTIMLCCMTSC<br>CSCLKGCCSCGSCC (SEQ ID NO: 45) |
| Soluble ACE2<br>(amino acid) | MSSSSWLLLSLVAVTAAQSTIEEQAKTFLDKFNHEAEDLFYQSSLASWNYN<br>TNITEENVQNMNNAGDKWSAFLKEQSTLAQMYPLQEIQNLTVKLQLQALQ<br>QNGSSVLSEDKSKRLNTILNTMSTIYSTGKVCNPDNPQECLLLEPGLNEIMA<br>NSLDYNERLWAWESWRSEVGKQLRPLYEEYVVLKNEMARANHYEDYGD<br>YWRGDYEVNGVDGYDYSRGQLIEDVEHTFEEIKPLYEHLHAYVRAKLMNA<br>YPSYISPIGCLPAHLLGDMWGRFWTNLYSLTVPFGQKPNIDVTDAMVDQA<br>WDAQRIFKEAEKFFVSVGLPNMTQGFWENSMLTDPGNVQKAVCHPTAWD<br>LGKGDFRILMCTKVTMDDFLTAHHEMGHIQYDMAYAAQPFLLRNGANEGF<br>HEAVGEIMSLSAATPKHLKSIGLLSPDFQEDNETEINFLLKQALTIVGTLPFT<br>YMLEKWRWMVFKGEIPKDQWMKKWWEMKREIVGVVEPVPHDETYCDPA<br>SLFHVSNDYSFIRYYTRTLYQFQFQEALCQAAKHEGPLHKCDISNSTEAGQ<br>KLFNMLRLGKSEPWTLALENVVGAKNMNVRPLLNYFEPLFTWLKDQNKNS<br>FVGWSTDWSPYADQSIKVRISLKSALGDRAYEWNDNEMYLFRSSVAYAM<br>RQYFLKVKNQMILFGEEDVRVANLKPRISFNFFVTAPKNVSDIIPRTEVEKAI<br>RMSRSRINDAFRLNDNSLEFLGIQPTLGPPNQPPVSHHHHHHHH (SEQ ID<br>NO: 46) |

TABLE 3-continued

| | |
|---|---|
| ACE2-microbody (amino acid) | MSSSSWLLLSLVAVTAAQSTIEEQAKTFLDKFNHEAEDLFYQSSLASWNYN<br>TNITEENVQNMNNAGDKWSAFLKEQSTLAQMYPLQEIQNLTVKLQLQALQ<br>QNGSSVLSEDKSKRLNTILNTMSTIYSTGKVCNPDNPQECLLLEPGLNEIMA<br>NSLDYNERLWAWESWRSEVGKQLRPLYEEYVVLKNEMARANHYEDYGD<br>YWRGDYEVNGVDGYDYSRGQLIEDVEHTFEEIKPLYEHLHAYVRAKLMNA<br>YPSYISPIGCLPAHLLGDMWGRFWTNLYSLTVPFGQKPNIDVTDAMVDQA<br>WDAQRIFKEAEKFFVSVGLPNMTQGFWENSMLTDPGNVQKAVCHPTAWD<br>LGKGDFRILMCTKVTMDDFLTAHHEMGHIQYDMAYAAQPFLLRNGANEGF<br>HEAVGEIMSLSAATPKHLKSIGLLSPDFQEDNETEINFLLKQALTIVGTLPFT<br>YMLEKWRWMVFKGEIPKDQWMKKWWEMKREIVGVVEPVPHDETYCDPA<br>SLFHVSNDYSFIRYYTRTLYQFQFQEALCQAAKHEGPLHKCDISNSTEAGQ<br>KLFNMLRLGKSEPWTLALENVVGAKNMNVRPLLNYFEPLFTWLKDQNKNS<br>FVGWSTDWSPYADQSIKVRISLKSALGDRAYEWNDNEMYLFRSSVAYAM<br>RQYFLKVKNQMILFGEEDVRVANLKPRISFNFFVTAPKNVSDIIPRTEVEKAI<br>RMSRSRINDAFRLNDNSLEFLGIQPTLGPPNQPPVSEPKSCDKTHTCPPCG<br>GGSSGGGSGGQPREPQVYTLPPSREEMTKNQVSLTCLVKGFYPSDIAVE<br>WESNGQPENNYKTTPPVLDSDGSFFLYSKLTVDKSRWQQGNVFSCSVMH<br>EALHNHYTQKSLSLSPGKHHHHHHHH<br>(SEQ ID NO: 47) |
| ACE2.H345A-microbody (amino acid) | MSSSSWLLLSLVAVTAAQSTIEEQAKTFLDKFNHEAEDLFYQSSLASWNYN<br>TNITEENVQNMNNAGDKWSAFLKEQSTLAQMYPLQEIQNLTVKLQLQALQ<br>QNGSSVLSEDKSKRLNTILNTMSTIYSTGKVCNPDNPQECLLLEPGLNEIMA<br>NSLDYNERLWAWESWRSEVGKQLRPLYEEYVVLKNEMARANHYEDYGD<br>YWRGDYEVNGVDGYDYSRGQLIEDVEHTFEEIKPLYEHLHAYVRAKLMNA<br>YPSYISPIGCLPAHLLGDMWGRFWTNLYSLTVPFGQKPNIDVTDAMVDQA<br>WDAQRIFKEAEKFFVSVGLPNMTQGFWENSMLTDPGNVQKAVCAPTAWD<br>LGKGDFRILMCTKVTMDDFLTAHHEMGHIQYDMAYAAQPFLLRNGANEGF<br>HEAVGEIMSLSAATPKHLKSIGLLSPDFQEDNETEINFLLKQALTIVGTLPFT<br>YMLEKWRWMVFKGEIPKDQWMKKWWEMKREIVGVVEPVPHDETYCDPA<br>SLFHVSNDYSFIRYYTRTLYQFQFQEALCQAAKHEGPLHKCDISNSTEAGQ<br>KLFNMLRLGKSEPWTLALENVVGAKNMNVRPLLNYFEPLFTWLKDQNKNS<br>FVGWSTDWSPYADQSIKVRISLKSALGDRAYEWNDNEMYLFRSSVAYAM<br>RQYFLKVKNQMILFGEEDVRVANLKPRISFNFFVTAPKNVSDIIPRTEVEKAI<br>RMSRSRINDAFRLNDNSLEFLGIQPTLGPPNQPPVSEPKSCDKTHTCPPCG<br>GGSSGGGSGGQPREPQVYTLPPSREEMTKNQVSLTCLVKGFYPSDIAVE<br>WESNGQPENNYKTTPPVLDSDGSFFLYSKLTVDKSRWQQGNVFSCSVMH<br>EALHNHYTQKSLSLSPGKHHHHHHHH (SEQ ID NO: 48) |

The following reference listing is not an indication that any particular reference is material to patentability.

Belouzard, S., J. K. Millet, B. N. Licitra and G. R. Whittaker (2012). "Mechanisms of coronavirus cell entry mediated by the viral spike protein." Viruses 4(6): 1011-1033.

Campeau, E., V. E. Ruhl, F. Rodier, C. L. Smith, B. L. Rahmberg, J. O. Fuss, J. Campisi, P. Yaswen, P. K. Cooper and P. D. Kaufman (2009). "A versatile viral system for expression and depletion of proteins in mammalian cells." PLoS One 4(8): e6529.

Case, J. B., P. W. Rothlauf, R. E. Chen, Z. Liu, H. Zhao, A. S. Kim, L. M. Bloyet, Q. Zeng, S. Tahan, L. Droit, M. X. G. Ilagan, M. A. Tartell, G. Amarasinghe, J. P. Henderson, S. Miersch, M. Ustav, S. Sidhu, H. W. Virgin, D. Wang, S. Ding, D. Corti, E. S. Theel, D. H. Fremont, M. S. Diamond and S. P. J. Whelan (2020). "Neutralizing antibody and soluble ACE2 inhibition of a replication-competent VSV-SARS-CoV-2 and a clinical isolate of SARS-CoV-2." bioRxiv.

Chiang, J. J., M. R. Gardner, B. D. Quinlan, T. Dorfman, H. Choe and M. Farzan (2012). "Enhanced recognition and neutralization of HIV-1 by antibody-derived CCR5-mimetic peptide variants." J Virol 86(22): 12417-12421.

Daar, E. S., X. L. Li, T. Moudgil and D. D. Ho (1990). "High concentrations of recombinant soluble CD4 are required to neutralize primary human immunodeficiency virus type 1 isolates." Proc Natl Acad Sci USA 87(17): 6574-6578.

Daniloski, Z., X. Guo and N. E. Sanjana (2020). "The D614G mutation in SARS-CoV-2 Spike increases transduction of multiple human cell types." bioRxiv.

Eaaswarkhanth, M., A. Al Madhoun and F. Al-Mulla (2020). "Could the D614G substitution in the SARS-CoV-2 spike (S) protein be associated with higher COVID-19 mortality?" Int J Infect Dis 96: 459-460.

Eroshenko, N., T. Gill, M. K. Keaveney, G. M. Church, J. M. Trevejo and H. Rajaniemi (2020). "Implications of antibody-dependent enhancement of infection for SARS-CoV-2 countermeasures." Nat Biotechnol 38(7): 789-791.

Fehr, A. R. and S. Perlman (2015). "Coronaviruses: an overview of their replication and pathogenesis." Methods Mol Biol 1282: 1-23.

Giroglou, T., J. Cinatl, Jr., H. Rabenau, C. Drosten, H. Schwalbe, H. W. Doerr and D. von Laer (2004). "Retroviral vectors pseudotyped with severe acute respiratory syndrome coronavirus S protein." J Virol 78(17): 9007-9015.

Guy, J. L., R. M. Jackson, H. A. Jensen, N. M. Hooper and A. J. Turner (2005). "Identification of critical active-site residues in angiotensin-converting enzyme-2 (ACE2) by site-directed mutagenesis." FEBS J 272(14): 3512-3520.

Haim, H., Z. Si, N. Madani, L. Wang, J. R. Courter, A. Princiotto, A. Kassa, M. DeGrace, K. McGee-Estrada, M. Mefford, D. Gabuzda, A. B. Smith, 3rd and J. Sodroski (2009). "Soluble CD4 and CD4-mimetic compounds inhibit HIV-1 infection by induction of a short-lived activated state." PLoS Pathog 5(4): e1000360.

Harmer, D., M. Gilbert, R. Borman and K. L. Clark (2002). "Quantitative mRNA expression profiling of ACE 2, a novel homologue of angiotensin converting enzyme." FEBS Lett 532(1-2): 107-110.

Haschke, M., M. Schuster, M. Poglitsch, H. Loibner, M. Salzberg, M. Bruggisser, J. Penninger and S. Krahenbuhl (2013). "Pharmacokinetics and pharmacodynamics of recombinant human angiotensin-converting enzyme 2 in healthy human subjects." *Clin Pharmacokinet* 52(9): 783-792.

Heald-Sargent, T. and T. Gallagher (2012). "Ready, set, fuse! The coronavirus spike protein and acquisition of fusion competence." *Viruses* 4(4): 557-580.

Khan, A., C. Benthin, B. Zeno, T. E. Albertson, J. Boyd, J. D. Christie, R. Hall, G. Poirier, J. J. Ronco, M. Tidswell, K. Hardes, W. M. Powley, T. J. Wright, S. K. Siederer, D. A. Fairman, D. A. Lipson, A. I. Bayliffe and A. L. Lazaar (2017). "A pilot clinical trial of recombinant human angiotensin-converting enzyme 2 in acute respiratory distress syndrome." *Crit Care* 21(1): 234.

Korber, B., W. M. Fischer, S. Gnanakaran, H. Yoon, J. Theiler, W. Abfalterer, N. Hengartner, E. E. Giorgi, T. Bhattacharya, B. Foley, K. M. Hastie, M. D. Parker, D. G. Partridge, C. M. Evans, T. M. Freeman, T. I. de Silva, C.-G. G. Sheffield, C. McDanal, L. G. Perez, H. Tang, A. Moon-Walker, S. P. Whelan, C. C. LaBranche, E. O. Saphire and D. C. Montefiori (2020). "Tracking Changes in SARS-CoV-2 Spike: Evidence that D614G Increases Infectivity of the COVID-19 Virus." *Cell*.

Ksiazek, T. G., D. Erdman, C. S. Goldsmith, S. R. Zaki, T. Peret, S. Emery, S. Tong, C. Urbani, J. A. Comer, W. Lim, P. E. Rollin, S. F. Dowell, A. E. Ling, C. D. Humphrey, W. J. Shieh, J. Guarner, C. D. Paddock, P. Rota, B. Fields, J. DeRisi, J. Y. Yang, N. Cox, J. M. Hughes, J. W. LeDuc, W. J. Bellini, L. J. Anderson and S. W. Group (2003). "A novel coronavirus associated with severe acute respiratory syndrome." *N Engl J Med* 348(20): 1953-1966.

Kuba, K., Y. Imai, T. Ohto-Nakanishi and J. M. Penninger (2010). "Trilogy of ACE2: a peptidase in the renin-angiotensin system, a SARS receptor, and a partner for amino acid transporters." *Pharmacol Ther* 128(1): 119-128.

Kuba, K., Y. Imai, S. Rao, H. Gao, F. Guo, B. Guan, Y. Huan, P. Yang, Y. Zhang, W. Deng, L. Bao, B. Zhang, G. Liu, Z. Wang, M. Chappell, Y. Liu, D. Zheng, A. Leibbrandt, T. Wada, A. S. Slutsky, D. Liu, C. Qin, C. Jiang and J. M. Penninger (2005). "A crucial role of angiotensin converting enzyme 2 (ACE2) in SARS coronavirus-induced lung injury." *Nat Med* 11(8): 875-879.

Lei, C., K. Qian, T. Li, S. Zhang, W. Fu, M. Ding and S. Hu (2020). "Neutralization of SARS-CoV-2 spike pseudotyped virus by recombinant ACE2-Ig." *Nat Commun* 11(1): 2070.

Letko, M. and V. Munster (2020). "Functional assessment of cell entry and receptor usage for lineage B beta-coronaviruses, including 2019-nCoV." *bioRxiv*.

Leung, W. K., K. F. To, P. K. Chan, H. L. Chan, A. K. Wu, N. Lee, K. Y. Yuen and J. J. Sung (2003). "Enteric involvement of severe acute respiratory syndrome-associated coronavirus infection." *Gastroenterology* 125(4): 1011-1017.

Li, F. (2015). "Receptor recognition mechanisms of coronaviruses: a decade of structural studies." *J Virol* 89(4): 1954-1964.

Li, F., W. Li, M. Farzan and S. C. Harrison (2005). "Structure of SARS coronavirus spike receptor-binding domain complexed with receptor." *Science* 309(5742): 1864-1868.

Li, W., H. Choe and M. Farzan (2006). "Insights from the association of SARS-CoV S-protein with its receptor, ACE2." *Adv Exp Med Biol* 581: 209-218.

Li, W., M. J. Moore, N. Vasilieva, J. Sui, S. K. Wong, M. A. Berne, M. Somasundaran, J. L. Sullivan, R. Luzuriaga, T. C. Greenough, H. Choe and M. Farzan (2003). "Angiotensin-converting enzyme 2 is a functional receptor for the SARS coronavirus." *Nature* 426(6965): 450-454.

Liu, P., J. Wysocki, T. Souma, M. Ye, V. Ramirez, B. Zhou, L. D. Wilsbacher, S. E. Quaggin, D. Bathe and J. Jin (2018). "Novel ACE2-Fc chimeric fusion provides long-lasting hypertension control and organ protection in mouse models of systemic renin angiotensin system activation." *Kidney Int* 94(1): 114-125.

Maute, R. L., S. R. Gordon, A. T. Mayer, M. N. McCracken, A. Natarajan, N. G. Ring, R. Kimura, J. M. Tsai, A. Manglik, A. C. Kruse, S. S. Gambhir, I. L. Weissman and A. M. Ring (2015). "Engineering high-affinity PD-1 variants for optimized immunotherapy and immuno-PET imaging." *Proc Natl Acad Sci USA* 112(47): E6506-6514.

Monteil, V., H. Kwon, P. Prado, A. Hagelkruys, R. A. Wimmer, M. Stahl, A. Leopoldi, E. Garreta, C. Hurtado Del Pozo, F. Prosper, J. P. Romero, G. Wirnsberger, H. Zhang, A. S. Slutsky, R. Conder, N. Montserrat, A. Mirazimi and J. M. Penninger (2020). "Inhibition of SARS-CoV-2 Infections in Engineered Human Tissues Using Clinical-Grade Soluble Human ACE2." *Cell* 181 (4): 905-913 e907.

Orloff, S. L., M. S. Kennedy, A. A. Belperron, P. J. Maddon and J. S. McDougal (1993). "Two mechanisms of soluble CD4 (sCD4)-mediated inhibition of human immunodeficiency virus type 1 (HIV-1) infectivity and their relation to primary HIV-1 isolates with reduced sensitivity to sCD4." *J Virol* 67(3): 1461-1471.

Riordan, J. F. (2003). "Angiotensin-I-converting enzyme and its relatives." *Genome Biol* 4(8): 225.

Schenten, D., L. Marcon, G. B. Karlsson, C. Parolin, T. Kodama, N. Gerard and J. Sodroski (1999). "Effects of soluble CD4 on simian immunodeficiency virus infection of CD4-positive and CD4-negative cells." *J Virol* 73(7): 5373-5380.

Shang, J., Y. Wan, C. Luo, G. Ye, Q. Geng, A. Auerbach and F. Li (2020). "Cell entry mechanisms of SARS-CoV-2." *Proc Natl Acad Sci USA* 117(21): 11727-11734.

Sullivan, N., Y. Sun, J. Binley, J. Lee, C. F. Barbas, 3rd, P. W. Parren, D. R. Burton and J. Sodroski (1998). "Determinants of human immunodeficiency virus type 1 envelope glycoprotein activation by soluble CD4 and monoclonal antibodies." *J Virol* 72(8): 6332-6338.

Tikellis, C. and M. C. Thomas (2012). "Angiotensin-Converting Enzyme 2 (ACE2) Is a Key Modulator of the Renin Angiotensin System in Health and Disease." *Int J Pept* 2012: 256294.

Wysocki, J., M. Ye, E. Rodriguez, F. R. Gonzalez-Pacheco, C. Barrios, K. Evora, M. Schuster, H. Loibner, K. B. Brosnihan, C. M. Ferrario, J. M. Penninger and D. Bathe (2010). "Targeting the degradation of angiotensin II with recombinant angiotensin-converting enzyme 2: prevention of angiotensin II-dependent hypertension." *Hypertension* 55(1): 90-98.

Xie, X., A. Muruato, K. G. Lokugamage, K. Narayanan, X. Zhang, J. Zou, J. Liu, C. Schindewolf, N. E. Bopp, P. V. Aguilar, K. S. Plante, S. C. Weaver, S. Makino, J. W. LeDuc, V. D. Menachery and P. Y. Shi (2020). "An Infectious cDNA Clone of SARS-CoV-2." *Cell Host Microbe* 27(5): 841-848 e843.

Zhang, L., C. B. Jackson, H. Mou, A. Ojha, E. S. Rangarajan, T. Izard, M. Farzan and H. Choe (2020). "The D614G mutation in the SARS-CoV-2 spike protein reduces S1 shedding and increases infectivity." *bioRxiv*.

What is claimed is:

1. A polypeptide comprising an enzymatically inactive angiotensin-converting enzyme 2 (ACE2) ectodomain that does not comprise an intact ACE2 transmembrane domain or an intact cytoplasmic tail, the polypeptide further comprising a segment of an immunoglobulin Fc that is not an intact Fc region, wherein the polypeptide comprises the sequence of amino acids 1-871 of SEQ ID NO:5.

2. The polypeptide of claim 1, wherein the polypeptide further comprises a purification tag.

3. The polypeptide of claim 2, wherein the purification tag is at the C-terminus of the polypeptide.

4. The polypeptide of claim 3, wherein the purification tag comprises a poly-Histidine tag.

5. A pharmaceutical formulation comprising the polypeptide of claim 1.

* * * * *

UNITED STATES PATENT AND TRADEMARK OFFICE
CERTIFICATE OF CORRECTION

| | | |
|---|---|---|
| PATENT NO. | : 12,037,619 B2 | Page 1 of 1 |
| APPLICATION NO. | : 17/405104 | |
| DATED | : July 16, 2024 | |
| INVENTOR(S) | : Landau et al. | |

It is certified that error appears in the above-identified patent and that said Letters Patent is hereby corrected as shown below:

In the Specification

Column 1, Line 9 should read:
--This invention was made with government support under DA046100 awarded by the National Institutes of Health. The government has certain rights in the invention.--

Signed and Sealed this
Fifteenth Day of April, 2025

Coke Morgan Stewart
*Acting Director of the United States Patent and Trademark Office*

SEQUENCE LISTING

<160> NUMBER OF SEQ ID NOS: 48

<210> SEQ ID NO 1
<211> LENGTH: 879
<212> TYPE: PRT
<213> ORGANISM: Artificial Sequence
<220> FEATURE:
<223> OTHER INFORMATION: ACE-2 Microbody

<400> SEQUENCE: 1

```
Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
```

-continued

```
               355                 360                 365
Phe Leu Thr Ala His His Glu Met Gly His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Phe Gln Phe Gln Glu Ala
        515                 520                 525
Leu Cys Gln Ala Ala Lys His Glu Gly Pro Leu His Lys Cys Asp Ile
    530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Gln Ser Ile Lys Val Arg Ile Ser Leu
    610                 615                 620
Lys Ser Ala Leu Gly Asp Arg Ala Tyr Glu Trp Asn Asp Asn Glu Met
625                 630                 635                 640
Tyr Leu Phe Arg Ser Ser Val Ala Tyr Ala Met Arg Gln Tyr Phe Leu
                645                 650                 655
Lys Val Lys Asn Gln Met Ile Leu Phe Gly Glu Glu Asp Val Arg Val
            660                 665                 670
Ala Asn Leu Lys Pro Arg Ile Ser Phe Asn Phe Phe Val Thr Ala Pro
        675                 680                 685
Lys Asn Val Ser Asp Ile Ile Pro Arg Thr Glu Val Glu Lys Ala Ile
    690                 695                 700
Arg Met Ser Arg Ser Arg Ile Asn Asp Ala Phe Arg Leu Asn Asp Asn
705                 710                 715                 720
Ser Leu Glu Phe Leu Gly Ile Gln Pro Thr Leu Gly Pro Pro Asn Gln
                725                 730                 735
Pro Pro Val Ser Glu Pro Lys Ser Cys Asp Lys Thr His Thr Cys Pro
            740                 745                 750
Pro Cys Gly Gly Gly Ser Ser Gly Gly Ser Gly Gly Gln Pro Arg
        755                 760                 765
Glu Pro Gln Val Tyr Thr Leu Pro Pro Ser Arg Glu Glu Met Thr Lys
    770                 775                 780
```

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
            805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
            835                 840                 845

Cys Ser Val Met His Glu Ala Leu His Asn His Tyr Thr Gln Lys Ser
            850                 855                 860

Leu Ser Leu Ser Pro Gly Lys His His His His His His His
865                 870                 875

<210> SEQ ID NO 2
<211> LENGTH: 740
<212> TYPE: PRT
<213> ORGANISM: Homo sapiens

<400> SEQUENCE: 2

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys

```
              275                 280                 285
Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
                435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Gln Ser Ile Lys Val Arg Ile Ser Leu
                610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700
```

```
Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Ser
        740

<210> SEQ ID NO 3
<211> LENGTH: 131
<212> TYPE: PRT
<213> ORGANISM: Artificial Sequence
<220> FEATURE:
<223> OTHER INFORMATION: Fc IgG-CH3

<400> SEQUENCE: 3

Glu Pro Lys Ser Cys Asp Lys Thr His Thr Cys Pro Pro Cys Gly Gly
1               5                   10                  15

Gly Ser Ser Gly Gly Gly Ser Gly Gly Gln Pro Arg Glu Pro Gln Val
            20                  25                  30

Tyr Thr Leu Pro Pro Ser Arg Glu Glu Met Thr Lys Asn Gln Val Ser
        35                  40                  45

Leu Thr Cys Leu Val Lys Gly Phe Tyr Pro Ser Asp Ile Ala Val Glu
    50                  55                  60

Trp Glu Ser Asn Gly Gln Pro Glu Asn Asn Tyr Lys Thr Thr Pro Pro
65                  70                  75                  80

Val Leu Asp Ser Asp Gly Ser Phe Phe Leu Tyr Ser Lys Leu Thr Val
                85                  90                  95

Asp Lys Ser Arg Trp Gln Gln Gly Asn Val Phe Ser Cys Ser Val Met
            100                 105                 110

His Glu Ala Leu His Asn His Tyr Thr Gln Lys Ser Leu Ser Leu Ser
        115                 120                 125

Pro Gly Lys
    130

<210> SEQ ID NO 4
<211> LENGTH: 8
<212> TYPE: PRT
<213> ORGANISM: Artificial Sequence
<220> FEATURE:
<223> OTHER INFORMATION: His tag

<400> SEQUENCE: 4

His His His His His His His His
1               5

<210> SEQ ID NO 5
<211> LENGTH: 879
<212> TYPE: PRT
<213> ORGANISM: Artificial Sequence
<220> FEATURE:
<223> OTHER INFORMATION: ACE2.H345A Microbody

<400> SEQUENCE: 5

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45
```

```
Asn Tyr Asn Thr Asn Ile Thr Glu Glu Asn Val Gln Asn Met Asn Asn
     50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys Ala Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
```

```
            465                 470                 475                 480
        Lys Arg Glu Ile Val Gly Val Glu Pro Val Pro His Asp Glu Thr
                        485                 490                 495

Tyr Cys Asp Pro Ala Ser Leu Phe His Val Ser Asn Asp Tyr Ser Phe
                    500                 505                 510

Ile Arg Tyr Tyr Thr Arg Thr Leu Tyr Gln Phe Gln Phe Gln Glu Ala
                    515                 520                 525

Leu Cys Gln Ala Ala Lys His Glu Gly Pro Leu His Lys Cys Asp Ile
                530                 535                 540

Ser Asn Ser Thr Glu Ala Gly Gln Lys Leu Phe Asn Met Leu Arg Leu
        545                 550                 555                 560

Gly Lys Ser Glu Pro Trp Thr Leu Ala Leu Glu Asn Val Val Gly Ala
                            565                 570                 575

Lys Asn Met Asn Val Arg Pro Leu Leu Asn Tyr Phe Glu Pro Leu Phe
                        580                 585                 590

Thr Trp Leu Lys Asp Gln Asn Lys Asn Ser Phe Val Gly Trp Ser Thr
                    595                 600                 605

Asp Trp Ser Pro Tyr Ala Asp Gln Ser Ile Lys Val Arg Ile Ser Leu
                610                 615                 620

Lys Ser Ala Leu Gly Asp Arg Ala Tyr Glu Trp Asn Asp Asn Glu Met
        625                 630                 635                 640

Tyr Leu Phe Arg Ser Ser Val Ala Tyr Ala Met Arg Gln Tyr Phe Leu
                            645                 650                 655

Lys Val Lys Asn Gln Met Ile Leu Phe Gly Glu Glu Asp Val Arg Val
                        660                 665                 670

Ala Asn Leu Lys Pro Arg Ile Ser Phe Asn Phe Phe Val Thr Ala Pro
                    675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
        705                 710                 715                 720

Ser Leu Glu Phe Leu Gly Ile Gln Pro Thr Leu Gly Pro Pro Asn Gln
                            725                 730                 735

Pro Pro Val Ser Glu Pro Lys Ser Cys Asp Lys Thr His Thr Cys Pro
                        740                 745                 750

Pro Cys Gly Gly Gly Ser Ser Gly Gly Gly Ser Gly Gly Gln Pro Arg
                    755                 760                 765

Glu Pro Gln Val Tyr Thr Leu Pro Pro Ser Arg Glu Glu Met Thr Lys
                770                 775                 780

Asn Gln Val Ser Leu Thr Cys Leu Val Lys Gly Phe Tyr Pro Ser Asp
        785                 790                 795                 800

Ile Ala Val Glu Trp Glu Ser Asn Gly Gln Pro Glu Asn Asn Tyr Lys
                            805                 810                 815

Thr Thr Pro Pro Val Leu Asp Ser Asp Gly Ser Phe Phe Leu Tyr Ser
                        820                 825                 830

Lys Leu Thr Val Asp Lys Ser Arg Trp Gln Gln Gly Asn Val Phe Ser
                    835                 840                 845

Cys Ser Val Met His Glu Ala Leu His Asn His Tyr Thr Gln Lys Ser
                850                 855                 860

Leu Ser Leu Ser Pro Gly Lys His His His His His His
        865                 870                 875

<210> SEQ ID NO 6
```

-continued

```
<211> LENGTH: 805
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Met | Ser | Ser | Ser | Trp | Leu | Leu | Leu | Ser | Leu | Val | Ala | Val | Thr | Ala |
| 1 | | | | 5 | | | | | 10 | | | | | 15 |
| Ala | Gln | Ser | Thr | Ile | Glu | Glu | Gln | Ala | Lys | Thr | Phe | Leu | Asp | Lys | Phe |
| | | | 20 | | | | | 25 | | | | | 30 | | |
| Asn | His | Glu | Ala | Glu | Asp | Leu | Phe | Tyr | Gln | Ser | Ser | Leu | Ala | Ser | Trp |
| | | 35 | | | | | 40 | | | | | 45 | | | |
| Asn | Tyr | Asn | Thr | Asn | Ile | Thr | Glu | Glu | Asn | Val | Gln | Asn | Met | Asn | Asn |
| 50 | | | | | 55 | | | | | 60 | | | | | |
| Ala | Gly | Asp | Lys | Trp | Ser | Ala | Phe | Leu | Lys | Glu | Gln | Ser | Thr | Leu | Ala |
| 65 | | | | | 70 | | | | | 75 | | | | | 80 |
| Gln | Met | Tyr | Pro | Leu | Gln | Glu | Ile | Gln | Asn | Leu | Thr | Val | Lys | Leu | Gln |
| | | | | 85 | | | | | 90 | | | | | 95 | |
| Leu | Gln | Ala | Leu | Gln | Gln | Asn | Gly | Ser | Ser | Val | Leu | Ser | Glu | Asp | Lys |
| | | | 100 | | | | | 105 | | | | | 110 | | |
| Ser | Lys | Arg | Leu | Asn | Thr | Ile | Leu | Asn | Thr | Met | Ser | Thr | Ile | Tyr | Ser |
| | | 115 | | | | | 120 | | | | | 125 | | | |
| Thr | Gly | Lys | Val | Cys | Asn | Pro | Asp | Asn | Pro | Gln | Glu | Cys | Leu | Leu | Leu |
| 130 | | | | | 135 | | | | | 140 | | | | | |
| Glu | Pro | Gly | Leu | Asn | Glu | Ile | Met | Ala | Asn | Ser | Leu | Asp | Tyr | Asn | Glu |
| 145 | | | | | 150 | | | | | 155 | | | | | 160 |
| Arg | Leu | Trp | Ala | Trp | Glu | Ser | Trp | Arg | Ser | Glu | Val | Gly | Lys | Gln | Leu |
| | | | | 165 | | | | | 170 | | | | | 175 | |
| Arg | Pro | Leu | Tyr | Glu | Glu | Tyr | Val | Val | Leu | Lys | Asn | Glu | Met | Ala | Arg |
| | | | 180 | | | | | 185 | | | | | 190 | | |
| Ala | Asn | His | Tyr | Glu | Asp | Tyr | Gly | Asp | Tyr | Trp | Arg | Gly | Asp | Tyr | Glu |
| | | 195 | | | | | 200 | | | | | 205 | | | |
| Val | Asn | Gly | Val | Asp | Gly | Tyr | Asp | Tyr | Ser | Arg | Gly | Gln | Leu | Ile | Glu |
| | 210 | | | | | 215 | | | | | 220 | | | | |
| Asp | Val | Glu | His | Thr | Phe | Glu | Glu | Ile | Lys | Pro | Leu | Tyr | Glu | His | Leu |
| 225 | | | | | 230 | | | | | 235 | | | | | 240 |
| His | Ala | Tyr | Val | Arg | Ala | Lys | Leu | Met | Asn | Ala | Tyr | Pro | Ser | Tyr | Ile |
| | | | | 245 | | | | | 250 | | | | | 255 | |
| Ser | Pro | Ile | Gly | Cys | Leu | Pro | Ala | His | Leu | Leu | Gly | Asp | Met | Trp | Gly |
| | | | 260 | | | | | 265 | | | | | 270 | | |
| Arg | Phe | Trp | Thr | Asn | Leu | Tyr | Ser | Leu | Thr | Val | Pro | Phe | Gly | Gln | Lys |
| | | 275 | | | | | 280 | | | | | 285 | | | |
| Pro | Asn | Ile | Asp | Val | Thr | Asp | Ala | Met | Val | Asp | Gln | Ala | Trp | Asp | Ala |
| | 290 | | | | | 295 | | | | | 300 | | | | |
| Gln | Arg | Ile | Phe | Lys | Glu | Ala | Glu | Lys | Phe | Phe | Val | Ser | Val | Gly | Leu |
| 305 | | | | | 310 | | | | | 315 | | | | | 320 |
| Pro | Asn | Met | Thr | Gln | Gly | Phe | Trp | Glu | Asn | Ser | Met | Leu | Thr | Asp | Pro |
| | | | | 325 | | | | | 330 | | | | | 335 | |
| Gly | Asn | Val | Gln | Lys | Ala | Val | Cys | His | Pro | Thr | Ala | Trp | Asp | Leu | Gly |
| | | | 340 | | | | | 345 | | | | | 350 | | |
| Lys | Gly | Asp | Phe | Arg | Ile | Leu | Met | Cys | Thr | Lys | Val | Thr | Met | Asp | Asp |
| | | 355 | | | | | 360 | | | | | 365 | | | |
| Phe | Leu | Thr | Ala | His | His | Glu | Met | Gly | His | Ile | Gln | Tyr | Asp | Met | Ala |
| 370 | | | | | 375 | | | | | 380 | | | | | |
| Tyr | Ala | Ala | Gln | Pro | Phe | Leu | Leu | Arg | Asn | Gly | Ala | Asn | Glu | Gly | Phe |

-continued

```
            385                 390                 395                 400
His Glu Ala Val Gly Glu Ile Met Ser Leu Ser Ala Ala Thr Pro Lys
                    405                 410                 415

His Leu Lys Ser Ile Gly Leu Leu Ser Pro Asp Phe Gln Glu Asp Asn
                    420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
        610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
            805
```

<210> SEQ ID NO 7
<211> LENGTH: 41
<212> TYPE: DNA
<213> ORGANISM: Artificial Sequence
<220> FEATURE:
<223> OTHER INFORMATION: primer

<400> SEQUENCE: 7
cggtatggta ccccaccatg ttcgtgtttc tggtgctgct g         41

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
cgtcgacgat gaattcgaca gccg         24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
ggcagcaatg gaattctgtt tcag         24

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
tacgctgacg ctcgagttag gcgtag         26

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11
cggtatggta ccccaccatg ttcgtgtttc tggtgctgct         40

<210> SEQ ID NO 12
<211> LENGTH: 41
<212> TYPE: DNA
<213> ORGANISM: Artificial Sequence
<220> FEATURE:
<223> OTHER INFORMATION: primer

<400> SEQUENCE: 12
ggctatctcg agttagcagc aggagccaca gctacagcag c         41

<210> SEQ ID NO 13
<211> LENGTH: 40
<212> TYPE: DNA
<213> ORGANISM: Artificial Sequence
<220> FEATURE:

<223> OTHER INFORMATION: primer

<400> SEQUENCE: 13
cggtatggta ccccaccatg ttcgtgtttc tggtgctgct                          40

<210> SEQ ID NO 14
<211> LENGTH: 68
<212> TYPE: DNA
<213> ORGANISM: Artificial Sequence
<220> FEATURE:
<223> OTHER INFORMATION: primer

<400> SEQUENCE: 14
ggctatctcg agttaagcgt agtctgggac gtcgtatggg tagcagcagg agccacagct    60
acagcagc                                                            68

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
cggtatggta ccccaccatg ttcgtgtttc tggtgctgct                          40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
ggctatctcg agttatgtgt aatgtaattt gactcctttg                          40

<210> SEQ ID NO 17
<211> LENGTH: 46
<212> TYPE: DNA
<213> ORGANISM: Artificial Sequence
<220> FEATURE:
<223> OTHER INFORMATION: primer

<400> SEQUENCE: 17
caggtggcag tgctgtacca gggtgtgaac tgtaccgaag tgcccg                   46

<210> SEQ ID NO 18
<211> LENGTH: 46
<212> TYPE: DNA
<213> ORGANISM: Artificial Sequence
<220> FEATURE:
<223> OTHER INFORMATION: primer

<400> SEQUENCE: 18
cgggcacttc ggtacagttc acaccctggt acagcactgc cacctg                   46

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
cggtatggta ccccaccatg ttcgtgtttc tggtgctgct                          40

<210> SEQ ID NO 20
<211> LENGTH: 68
<212> TYPE: DNA
<213> ORGANISM: Artificial Sequence
<220> FEATURE:
<223> OTHER INFORMATION: primer

<400> SEQUENCE: 20
ggctatctcg agttaagcgt agtctgggac gtcgtatggg tagcagcagg agccacagct    60
acagcagc                                                            68

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21
caggtggcag tgctgtacca gggtgtgaac tgtaccgaag tgcccg                  46

<210> SEQ ID NO 22
<211> LENGTH: 46
<212> TYPE: DNA
<213> ORGANISM: Artificial Sequence
<220> FEATURE:
<223> OTHER INFORMATION: primer

<400> SEQUENCE: 22
cgggcacttc ggtacagttc acaccctggt acagcactgc cacctg                  46

<210> SEQ ID NO 23
<211> LENGTH: 42
<212> TYPE: DNA
<213> ORGANISM: Artificial Sequence
<220> FEATURE:
<223> OTHER INFORMATION: primer

<400> SEQUENCE: 23
cggtattcta gaccaccatg tcaagctctt cctggctcct tc                      42

<210> SEQ ID NO 24
<211> LENGTH: 67
<212> TYPE: DNA
<213> ORGANISM: Artificial Sequence
<220> FEATURE:
<223> OTHER INFORMATION: primer

<400> SEQUENCE: 24
ggctatgtcg acctaagcgt agtctgggac gtcgtatggg taaaaggagg tctgaacatc    60
atcagtg                                                             67

<210> SEQ ID NO 25
<211> LENGTH: 42
<212> TYPE: DNA
<213> ORGANISM: Artificial Sequence
<220> FEATURE:
<223> OTHER INFORMATION: primer

<400> SEQUENCE: 25
cggtatggta ccccaccatg tcaagctctt cctggctcct tc                      42

<210> SEQ ID NO 26

```
<211> LENGTH: 66
<212> TYPE: DNA
<213> ORGANISM: Artificial Sequence
<220> FEATURE:
<223> OTHER INFORMATION: primer

<400> SEQUENCE: 26
ggctatctcg agtcagtgat ggtggtgatg gtgatgatgg gaaacagggg gctggttagg      60
aggtcc                                                                66

<210> SEQ ID NO 27
<211> LENGTH: 50
<212> TYPE: DNA
<213> ORGANISM: Artificial Sequence
<220> FEATURE:
<223> OTHER INFORMATION: primer

<400> SEQUENCE: 27
agttttgtca caagatttgg gctcggaaac aggggctgg ttaggaggtc                  50

<210> SEQ ID NO 28
<211> LENGTH: 50
<212> TYPE: DNA
<213> ORGANISM: Artificial Sequence
<220> FEATURE:
<223> OTHER INFORMATION: primer

<400> SEQUENCE: 28
gacctcctaa ccagcccct gtttccgagc ccaaatcttg tgacaaaact                  50

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
cggtatggta ccccaccatg tcaagctctt cctggctcct tc                        42

<210> SEQ ID NO 30
<211> LENGTH: 66
<212> TYPE: DNA
<213> ORGANISM: Artificial Sequence
<220> FEATURE:
<223> OTHER INFORMATION: primer

<400> SEQUENCE: 30
ggctatctcg agtcagtgat ggtggtgatg gtgatgatgg gaaacagggg gctggttagg      60
aggtcc                                                                66

<210> SEQ ID NO 31
<211> LENGTH: 40
<212> TYPE: DNA
<213> ORGANISM: Artificial Sequence
<220> FEATURE:
<223> OTHER INFORMATION: primer

<400> SEQUENCE: 31
ggaaatgttc agaaagcagt ctgcgctccc acagcttggg                           40

<210> SEQ ID NO 32
<211> LENGTH: 40
<212> TYPE: DNA
<213> ORGANISM: Artificial Sequence
```

```
<220> FEATURE:
<223> OTHER INFORMATION: primer

<400> SEQUENCE: 32
cccaagctgt gggagcgcag actgctttct gaacatttcc                              40

<210> SEQ ID NO 33
<211> LENGTH: 42
<212> TYPE: DNA
<213> ORGANISM: Artificial Sequence
<220> FEATURE:
<223> OTHER INFORMATION: primer

<400> SEQUENCE: 33
cggtatggta ccccaccatg tcaagctctt cctggctcct tc                           42

<210> SEQ ID NO 34
<211> LENGTH: 36
<212> TYPE: DNA
<213> ORGANISM: Artificial Sequence
<220> FEATURE:
<223> OTHER INFORMATION: primer

<400> SEQUENCE: 34
ggctatctcg agtcagtgat ggtggtgatg gtgatg                                  36

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
cggtatggat ccccaccatg gtgagcaagg                                         30

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
ggctatgtcg acttacgcca gaatgcg                                            27

<210> SEQ ID NO 37
<211> LENGTH: 60
<212> TYPE: DNA
<213> ORGANISM: Artificial Sequence
<220> FEATURE:
<223> OTHER INFORMATION: primer

<400> SEQUENCE: 37
gcctgctgaa gcaggctgga gacgtggagg agaaccctgg acctgtcttc acactcgaag        60

<210> SEQ ID NO 38
<211> LENGTH: 60
<212> TYPE: DNA
<213> ORGANISM: Artificial Sequence
<220> FEATURE:
<223> OTHER INFORMATION: primer

<400> SEQUENCE: 38
cagcctgctt cagcaggctg aagttagtag ctccgcttcc cttgtacagc tcgtccatgc        60
```

<210> SEQ ID NO 39
<211> LENGTH: 1986
<212> TYPE: DNA
<213> ORGANISM: Artificial Sequence
<220> FEATURE:
<223> OTHER INFORMATION: S fragment A

<400> SEQUENCE: 39

| | | | | | |
|---|---|---|---|---|---|
| cgatgctcac | ggatccgcca | ccatgttcgt | gtttctggtg | ctgctgcctc | tggtgtccag     60 |
| ccagtgtgtg | aacctgacca | ccagaacaca | gctgcctcca | gcctacacca | acagctttac    120 |
| cagaggcgtg | tactacccecg | acaaggtgtt | cagatccagc | gtgctgcact | ctacccagga    180 |
| cctgttcctg | cctttcttca | gcaacgtgac | ctggttccac | gccatccacg | tgtccggcac    240 |
| caatggcacc | aagagattcg | acaacccecgt | gctgccecttc | aacgacgggg | tgtactttgc    300 |
| cagcaccgag | aagtccaaca | tcatcagagg | ctggatcttg | gcaccacac | tggacagcaa    360 |
| gacccagagc | ctgctgatcg | tgaacaacgc | caccaacgtg | gtcatcaaag | tgtgcgagtt    420 |
| ccagttctgc | aacgaccect | tcctgggcgt | ctactaccac | aagaacaaca | agagctggat    480 |
| ggaaagcgag | ttccgggtgt | acagcagcgc | caacaactgc | accttcgagt | acgtgtccca    540 |
| gccetttcctg | atggacctgg | aaggcaagca | gggcaacttc | aagaacctgc | gcgagttcgt    600 |
| gttcaagaac | atcgacggct | acttcaagat | ctacagcaag | cacacccecta | tcaacctcgt    660 |
| gcgggatctg | cctcagggct | ctctgctct | ggaaccccetg | gtggatctgc | ccatcggcat    720 |
| caacatcacc | cggtttcaga | cactgctggc | cctgcacaga | agctacctga | cacctggcga    780 |
| tagcagcagc | ggatggacag | ctggtgccgc | cgcttactat | gtgggctacc | tgcagcctag    840 |
| aaccttcctg | ctgaagtaca | acgagaacgg | caccatcacc | gacgccgtgg | attgtgctct    900 |
| ggatcctctg | agcgagacaa | agtgcaccecct | gaagtccttc | accgtggaaa | agggcatcta    960 |
| ccagaccagc | aacttccggg | tgcagcccac | cgaatccatc | gtgcggttcc | ccaatatcac   1020 |
| caatctgtgc | ccecttcggcg | aggtgttcaa | tgccaccaga | ttcgcctctg | tgtacgcctg   1080 |
| gaaccggaag | cggatcagca | attgcgtggc | cgactactcc | gtgctgtaca | actccgccag   1140 |
| cttcagcacc | ttcaagtgct | acggcgtgtc | ccctaccaag | ctgaacgacc | tgtgcttcac   1200 |
| aaacgtgtac | gccgacagct | tcgtgatccg | gggagatgaa | gtgcggcaga | ttgccecctgg   1260 |
| acagacaggc | aagatcgccg | actacaacta | caagctgccc | gacgacttca | ccggctgtgt   1320 |
| gattgcctgg | aacagcaaca | acctggactc | caaagtcggc | ggcaactaca | attacctgta   1380 |
| ccggctgttc | cggaagtcca | atctgaagcc | cttcgagcgg | gacatctcca | ccgagatcta   1440 |
| tcaggccggc | agcacccectt | gtaacggcgt | ggaaggcttc | aactgctact | tcccactgca   1500 |
| gtcctacggc | tttcagccca | caaatggcgt | gggctatcag | ccctacagag | tggtggtgct   1560 |
| gagcttcgaa | ctgctgcatg | cccctgccac | agtgtgcggc | cctaagaaaa | gcaccaatct   1620 |
| cgtgaagaac | aaatgcgtga | acttcaactt | caacggcctg | accggcaccg | gcgtgctgac   1680 |
| agagagcaac | aagaagttcc | tgccattcca | gcagtttggc | cgggatatcg | ccgataccac   1740 |
| agacgccgtt | agagatcccc | agacactgga | aatcctggac | atcaccccectt | gcagcttcgg   1800 |
| cggagtgtct | gtgatcaccc | ctggcaccaa | caccagcaat | caggtggcag | tgctgtacca   1860 |
| ggacgtgaac | tgtaccgaag | tgcccgtggc | cattcacgcc | gatcagctga | cacctacatg   1920 |
| gcgggtgtac | tccaccggct | ccaatgtgtt | tcaaacgcgt | gccggctgtc | gaattcatcg   1980 |
| tcgacg | | | | |   1986 |

<210> SEQ ID NO 40
<211> LENGTH: 1957
<212> TYPE: DNA
<213> ORGANISM: Artificial Sequence
<220> FEATURE:
<223> OTHER INFORMATION: S fragment B

<400> SEQUENCE: 40

```
ggcagcaatg gaattctgtt tcagacgcgt gccggctgcc tgattggagc cgaacacgtg      60
aacaacagct acgagtgcga catccctatc ggagccggca tctgtgccag ctaccagaca     120
cagacaaaca gccccagacg ggccagatct gtggccagcc agagcatcat tgcctacacc     180
atgtctctgg gcgccgagaa cagcgtggcc tacagcaaca actctatcgc tatccccacc     240
aacttcacca tcagcgtgac caccgagatc ctgcctgtgt ccatgaccaa gaccagcgtg     300
gactgcacca tgtacatctg cggcgatagc accgagtgca gcaacctgct gctgcagtac     360
ggcagcttct gcacccagct gaatagagcc ctgaccggaa tcgccgtgga acaggacaag     420
aacacccaag aggtgttcgc ccaagtgaag cagatctaca agaccccctc tatcaaggac     480
ttcggcggct tcaacttcag ccagattctg cccgatccta gcaagcccag caagcggagc     540
ttcatcgagg acctgctgtt caacaaagtg accctggccg acgccggctt catcaagcag     600
tatggcgatt gcctgggcga cattgccgcc agggatctga tttgcgccca agagtttaac     660
ggcctgaccg tgctgcctcc tctgctgacc gatgagatga tcgcccagta cacatctgcc     720
ctgctggccg gcacaatcac aagcggctgg acatttggag ctggcgccgc tctgcagatc     780
ccctttgcta tgcagatggc ctaccggttc aacggcatcg gcgtgaccca gaacgtgctg     840
tacgagaacc agaagctgat cgccaaccag ttcaacagcg ccatcggcaa gatccaggac     900
agcctgagca gtacagccag cgctctggga aagctgcagg acgtggtcaa ccagaatgcc     960
caggctctga acaccctggt caagcagctg agcagcaact tcggcgccat cagcagcgtg    1020
ctgaacgaca tcctgagccg cctggataag gtggaagccg aggtgcagat cgaccggctg    1080
attacaggca gactgcagag cctgcagacc tacgtgacac agcagctgat cagagccgcc    1140
gagattagag cctctgccaa tctggccgcc accaagatgt ctgagtgtgt gctgggccag    1200
agcaagagag tggacttttg cggcaagggc taccacctga tgagcttccc tcagtctgct    1260
cctcacggcg tggtgtttct gcacgtgaca tacgtgcccg ctcaagagaa gaatttcacc    1320
accgctccag ccatctgcca cgacggcaaa gcccactttc tagagaagg cgtgttcgtg    1380
tccaacggca cccattggtt cgtgactcag cggaacttct acgagcccca gatcatcacc    1440
accgacaaca ccttcgtgtc cggcaactgc gacgtcgtga tcggcatcgt gaacaatacc    1500
gtgtacgacc ctctgcagcc cgagctggac agcttcaaag aggaactgga caagtacttc    1560
aagaaccaca aagcccccga cgtggacctg ggcgatatca gcggaatcaa tgccagcgtc    1620
gtgaacatcc agaaagagat cgacagactg aacgaggtgg ccaagaacct gaacgagagc    1680
ctgatcgacc tgcaagagct ggggaagtac gagcagtata tcaagtggcc ctggtacatc    1740
tggctgggct ttatcgccgg cctgattgcc atcgtgatgg tcacaatcat gctgtgctgc    1800
atgaccagct gttgcagctg cctgaagggc tgctgtagct gtggctcctg ctgcaagttc    1860
gacgaggacg attctgagcc cgtgctgaag ggcgtgaagc tgcactacac ataccccta    1920
gacgtgcccg actacgccta actcgagcgt cagcgta                             1957
```

<210> SEQ ID NO 41
<211> LENGTH: 2418
<212> TYPE: DNA

<213> ORGANISM: Homo sapiens

<400> SEQUENCE: 41

| | |
|---|---|
| atgtcaagct cttcctggct ccttctcagc cttgttgctg taactgctgc tcagtccacc | 60 |
| attgaggaac aggccaagac attttttggac aagtttaacc acgaagccga agacctgttc | 120 |
| tatcaaagtt cacttgcttc ttggaattat aacaccaata ttactgaaga gaatgtccaa | 180 |
| aacatgaata atgctgggga caaatggtct gccttttaa aggaacagtc cacacttgcc | 240 |
| caaatgtatc cactacaaga aattcagaat ctcacagtca agcttcagct gcaggctctt | 300 |
| cagcaaaatg ggtcttcagt gctctcagaa gacaagagca aacggttgaa cacaattcta | 360 |
| aatacaatga gcaccatcta cagtactgga aaagtttgta acccagataa tccacaagaa | 420 |
| tgcttattac ttgaaccagg tttgaatgaa ataatggcaa acagtttaga ctacaatgag | 480 |
| aggctctggg cttgggaaag ctggagatct gaggtcggca agcagctgag gccattatat | 540 |
| gaagagtatg tggtcttgaa aaatgagatg gcaagagcaa atcattatga ggactatggg | 600 |
| gattattgga gaggagacta tgaagtaaat ggggtagatg ctatgactca cagccgcggc | 660 |
| cagttgattg aagatgtgga acatacccttt gaagagatta accattata tgaacatctt | 720 |
| catgcctatg tgagggcaaa gttgatgaat gcctatcctt cctatatcag tccaattgga | 780 |
| tgcctccctg ctcatttgct tggtgatatg tggggtagat tttggacaaa tctgtactct | 840 |
| ttgacagttc cctttggaca gaaccaaac atagatgtta ctgatgcaat ggtggaccag | 900 |
| gcctgggatg cacagagaat attcaaggag ccgagaagt tctttgtatc tgttggtctt | 960 |
| cctaatatga ctcaaggatt ctgggaaaat tccatgctaa cggacccagg aaatgttcag | 1020 |
| aaagcagtct gccatcccac agcttgggac ctggggaagg gcgacttcag gatccttatg | 1080 |
| tgcacaaagg tgacaatgga cgacttcctg acagctcatc atgagatggg gcatatccag | 1140 |
| tatgatatgg catatgctgc acaacctttt ctgctaagaa atggagctaa tgaaggattc | 1200 |
| catgaagctg ttgggaaat catgtcactt tctgcagcca cacctaagca tttaaaatcc | 1260 |
| attggtcttc tgtcacccga ttttcaagaa gacaatgaaa cagaaataaa cttcctgctc | 1320 |
| aaacaagcac tcacgattgt tgggactctg ccatttactt acatgttaga gaagtggagg | 1380 |
| tggatggtct ttaaagggga aattcccaaa gaccagtgga tgaaaaagtg gtgggagatg | 1440 |
| aagcgagaga tagttgggt ggtggaacct gtgccccatg atgaaacata ctgtgacccc | 1500 |
| gcatctctgt ccatgtttc taatgattac tcattcattc gatattacac aaggacccctt | 1560 |
| taccaattcc agtttcaaga agcactttgt caagcagcta acatgaagg ccctctgcac | 1620 |
| aaatgtgaca tctcaaactc tacagaagct ggacagaaac tgttcaatat gctgaggctt | 1680 |
| ggaaaatcag aaccctggac cctagcattg gaaaatgttg taggagcaaa gaacatgaat | 1740 |
| gtaaggccac tgctcaacta ctttgagccc ttatttacct ggctgaaaga ccagaacaag | 1800 |
| aattcttttg tgggatggag taccgactgg agtccatatg cagaccaaag catcaaagtg | 1860 |
| aggataagcc taaaatcagc tcttggagat aaagcatatg aatggaacga caatgaaatg | 1920 |
| tacctgttcc gatcatctgt tgcatatgct atgaggcagt acttttaaa agtaaaaaat | 1980 |
| cagatgattc ttttttgggga ggaggatgtg cgagtggcta atttgaaacc aagaatctcc | 2040 |
| tttaatttct ttgtcactgc acctaaaaat gtgtctgata tcattcctag aactgaagtt | 2100 |
| gaaaaggcca tcaggatgtc ccggagccgt atcaatgatg ctttccgtct gaatgacaac | 2160 |
| agcctagagt ttctggggat acagccaaca cttggacctc ctaaccagcc ccctgttttcc | 2220 |
| atatggctga ttgttttttgg agttgtgatg ggagtgatag tggttggcat tgtcatcctg | 2280 |

-continued

```
atcttcactg ggatcagaga tcggaagaag aaaaataaag caagaagtgg agaaaatcct    2340
tatgcctcca tcgatattag caaaggagaa aataatccag gattccaaaa cactgatgat    2400
gttcagacct cctttttag                                                 2418
```

<210> SEQ ID NO 42
<211> LENGTH: 1282
<212> TYPE: PRT
<213> ORGANISM: Artificial Sequence
<220> FEATURE:
<223> OTHER INFORMATION: SARS-CoV-2 S-HA

<400> SEQUENCE: 42

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

```
Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
   1010                 1015                1020

Leu Ala Ala Thr Lys Met Ser Glu Cys Val Leu Gly Gln Ser Lys
   1025                 1030                1035

Arg Val Asp Phe Cys Gly Lys Gly Tyr His Leu Met Ser Phe Pro
   1040                 1045                1050

Gln Ser Ala Pro His Gly Val Val Phe Leu His Val Thr Tyr Val
   1055                 1060                1065

Pro Ala Gln Glu Lys Asn Phe Thr Thr Ala Pro Ala Ile Cys His
   1070                 1075                1080

Asp Gly Lys Ala His Phe Pro Arg Glu Gly Val Phe Val Ser Asn
   1085                 1090                1095

Gly Thr His Trp Phe Val Thr Gln Arg Asn Phe Tyr Glu Pro Gln
   1100                 1105                1110

Ile Ile Thr Thr Asp Asn Thr Phe Val Ser Gly Asn Cys Asp Val
   1115                 1120                1125

Val Ile Gly Ile Val Asn Asn Thr Val Tyr Asp Pro Leu Gln Pro
   1130                 1135                1140

Glu Leu Asp Ser Phe Lys Glu Glu Leu Asp Lys Tyr Phe Lys Asn
   1145                 1150                1155

His Thr Ser Pro Asp Val Asp Leu Gly Asp Ile Ser Gly Ile Asn
```

```
                1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr Tyr Pro Tyr Asp Val
    1265                1270                1275

Pro Asp Tyr Ala
    1280

<210> SEQ ID NO 43
<211> LENGTH: 1254
<212> TYPE: PRT
<213> ORGANISM: Artificial Sequence
<220> FEATURE:
<223> OTHER INFORMATION: SARS-CoV-2 delta19 S

```
                225                 230                 235                 240
        Leu Leu Ala Leu His Arg Ser Tyr Leu Thr Pro Gly Asp Ser Ser Ser
                        245                 250                 255

Gly Trp Thr Ala Gly Ala Ala Tyr Tyr Val Gly Tyr Leu Gln Pro
                        260                 265                 270

Arg Thr Phe Leu Leu Lys Tyr Asn Glu Asn Gly Thr Ile Thr Asp Ala
                        275                 280                 285

Val Asp Cys Ala Leu Asp Pro Leu Ser Glu Thr Lys Cys Thr Leu Lys
                290                 295                 300

Ser Phe Thr Val Glu Lys Gly Ile Tyr Gln Thr Ser Asn Phe Arg Val
        305                 310                 315                 320

Gln Pro Thr Glu Ser Ile Val Arg Phe Pro Asn Ile Thr Asn Leu Cys
                        325                 330                 335

Pro Phe Gly Glu Val Phe Asn Ala Thr Arg Phe Ala Ser Val Tyr Ala
                        340                 345                 350

Trp Asn Arg Lys Arg Ile Ser Asn Cys Val Ala Asp Tyr Ser Val Leu
                        355                 360                 365

Tyr Asn Ser Ala Ser Phe Ser Thr Phe Lys Cys Tyr Gly Val Ser Pro
                        370                 375                 380

Thr Lys Leu Asn Asp Leu Cys Phe Thr Asn Val Tyr Ala Asp Ser Phe
        385                 390                 395                 400

Val Ile Arg Gly Asp Glu Val Arg Gln Ile Ala Pro Gly Gln Thr Gly
                        405                 410                 415

Lys Ile Ala Asp Tyr Asn Tyr Lys Leu Pro Asp Asp Phe Thr Gly Cys
                        420                 425                 430

Val Ile Ala Trp Asn Ser Asn Asn Leu Asp Ser Lys Val Gly Gly Asn
                        435                 440                 445

Tyr Asn Tyr Leu Tyr Arg Leu Phe Arg Lys Ser Asn Leu Lys Pro Phe
                450                 455                 460

Glu Arg Asp Ile Ser Thr Glu Ile Tyr Gln Ala Gly Ser Thr Pro Cys
        465                 470                 475                 480

Asn Gly Val Glu Gly Phe Asn Cys Tyr Phe Pro Leu Gln Ser Tyr Gly
                        485                 490                 495

Phe Gln Pro Thr Asn Gly Val Gly Tyr Gln Pro Tyr Arg Val Val Val
                        500                 505                 510

Leu Ser Phe Glu Leu Leu His Ala Pro Ala Thr Val Cys Gly Pro Lys
                        515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
        545                 550                 555                 560

Pro Phe Gln Gln Phe Gly Arg Asp Ile Ala Asp Thr Thr Asp Ala Val
                        565                 570                 575

Arg Asp Pro Gln Thr Leu Glu Ile Leu Asp Ile Thr Pro Cys Ser Phe
                        580                 585                 590

Gly Gly Val Ser Val Ile Thr Pro Gly Thr Asn Thr Ser Asn Gln Val
                        595                 600                 605

Ala Val Leu Tyr Gln Asp Val Asn Cys Thr Glu Val Pro Val Ala Ile
                        610                 615                 620

His Ala Asp Gln Leu Thr Pro Thr Trp Arg Val Tyr Ser Thr Gly Ser
        625                 630                 635                 640

Asn Val Phe Gln Thr Arg Ala Gly Cys Leu Ile Gly Ala Glu His Val
                        645                 650                 655
```

```
Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
            1010                1015                1020

Leu Ala Ala Thr Lys Met Ser Glu Cys Val Leu Gly Gln Ser Lys
            1025                1030                1035

Arg Val Asp Phe Cys Gly Lys Gly Tyr His Leu Met Ser Phe Pro
            1040                1045                1050

Gln Ser Ala Pro His Gly Val Val Phe Leu His Val Thr Tyr Val
            1055                1060                1065
```

```
Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys
    1250

<210> SEQ ID NO 44
<211> LENGTH: 1263
<212> TYPE: PRT
<213> ORGANISM: Artificial Sequence
<220> FEATURE:
<223> OTHER INFORMATION: SARS-CoV-2 delta19 S-HA

<400> SEQUENCE: 44

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160
```

-continued

```
Ser Ser Ala Asn Asn Cys Thr Phe Glu Tyr Val Ser Gln Pro Phe Leu
            165                 170                 175
Met Asp Leu Glu Gly Lys Gln Gly Asn Phe Lys Asn Leu Arg Glu Phe
        180                 185                 190
Val Phe Lys Asn Ile Asp Gly Tyr Phe Lys Ile Tyr Ser Lys His Thr
        195                 200                 205
Pro Ile Asn Leu Val Arg Asp Leu Pro Gln Gly Phe Ser Ala Leu Glu
    210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
        275                 280                 285
Val Asp Cys Ala Leu Asp Pro Leu Ser Glu Thr Lys Cys Thr Leu Lys
        290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
        355                 360                 365
Tyr Asn Ser Ala Ser Phe Ser Thr Phe Lys Cys Tyr Gly Val Ser Pro
    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
        435                 440                 445
Tyr Asn Tyr Leu Tyr Arg Leu Phe Arg Lys Ser Asn Leu Lys Pro Phe
    450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
        515                 520                 525
Lys Ser Thr Asn Leu Val Lys Asn Lys Cys Val Asn Phe Asn Phe Asn
        530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
```

-continued

```
            580                 585                 590
Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
        645                 650                 655

Asn Asn Ser Tyr Glu Cys Asp Ile Pro Ile Gly Ala Gly Ile Cys Ala
        660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
        995                 1000                1005
```

```
Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Tyr Pro Tyr Asp Val Pro Asp Tyr Ala
    1250                1255                1260

<210> SEQ ID NO 45
<211> LENGTH: 1254
<212> TYPE: PRT
<213> ORGANISM: Artificial Sequence
<220> FEATURE:
<223> OTHER INFORMATION: SARS- CoV-2 D614G delta19 S

<400> SEQUENCE: 45

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

```
Lys Ser Asn Ile Ile Arg Gly Trp Ile Phe Gly Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
```

```
                 930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                 965                 970                 975

Leu Asn Asp Ile Leu Ser Arg Leu Asp Lys Val Glu Ala Glu Val Gln
                 980                 985                 990

Ile Asp Arg Leu Ile Thr Gly Arg Leu Gln Ser Leu Gln Thr Tyr Val
                 995                1000                1005

Thr Gln Gln Leu Ile Arg Ala Ala Glu Ile Arg Ala Ser Ala Asn
               1010                1015                1020

Leu Ala Ala Thr Lys Met Ser Glu Cys Val Leu Gly Gln Ser Lys
               1025                1030                1035

Arg Val Asp Phe Cys Gly Lys Gly Tyr His Leu Met Ser Phe Pro
               1040                1045                1050

Gln Ser Ala Pro His Gly Val Val Phe Leu His Val Thr Tyr Val
               1055                1060                1065

Pro Ala Gln Glu Lys Asn Phe Thr Thr Ala Pro Ala Ile Cys His
               1070                1075                1080

Asp Gly Lys Ala His Phe Pro Arg Glu Gly Val Phe Val Ser Asn
               1085                1090                1095

Gly Thr His Trp Phe Val Thr Gln Arg Asn Phe Tyr Glu Pro Gln
               1100                1105                1110

Ile Ile Thr Thr Asp Asn Thr Phe Val Ser Gly Asn Cys Asp Val
               1115                1120                1125

Val Ile Gly Ile Val Asn Asn Thr Val Tyr Asp Pro Leu Gln Pro
               1130                1135                1140

Glu Leu Asp Ser Phe Lys Glu Leu Asp Lys Tyr Phe Lys Asn
               1145                1150                1155

His Thr Ser Pro Asp Val Asp Leu Gly Asp Ile Ser Gly Ile Asn
               1160                1165                1170

Ala Ser Val Val Asn Ile Gln Lys Glu Ile Asp Arg Leu Asn Glu
               1175                1180                1185

Val Ala Lys Asn Leu Asn Glu Ser Leu Ile Asp Leu Gln Glu Leu
               1190                1195                1200

Gly Lys Tyr Glu Gln Tyr Ile Lys Trp Pro Trp Tyr Ile Trp Leu
               1205                1210                1215

Gly Phe Ile Ala Gly Leu Ile Ala Ile Val Met Val Thr Ile Met
               1220                1225                1230

Leu Cys Cys Met Thr Ser Cys Cys Ser Cys Leu Lys Gly Cys Cys
               1235                1240                1245

Ser Cys Gly Ser Cys Cys
               1250

<210> SEQ ID NO 46
<211> LENGTH: 748
<212> TYPE: PRT
<213> ORGANISM: Artificial Sequence
<220> FEATURE:
<223> OTHER INFORMATION: Soluble ACE2

<400> SEQUENCE: 46

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
```

-continued

```
                    20                  25                  30
Asn His Glu Ala Glu Asp Leu Phe Tyr Gln Ser Ser Leu Ala Ser Trp
                35                  40                  45
Asn Tyr Asn Thr Asn Ile Thr Glu Glu Asn Val Gln Asn Met Asn Asn
 50                  55                  60
Ala Gly Asp Lys Trp Ser Ala Phe Leu Lys Glu Gln Ser Thr Leu Ala
 65                  70                  75                  80
Gln Met Tyr Pro Leu Gln Glu Ile Gln Asn Leu Thr Val Lys Leu Gln
                85                  90                  95
Leu Gln Ala Leu Gln Gln Asn Gly Ser Ser Val Leu Ser Glu Asp Lys
                100                 105                 110
Ser Lys Arg Leu Asn Thr Ile Leu Asn Thr Met Ser Thr Ile Tyr Ser
                115                 120                 125
Thr Gly Lys Val Cys Asn Pro Asp Asn Pro Gln Glu Cys Leu Leu Leu
                130                 135                 140
Glu Pro Gly Leu Asn Glu Ile Met Ala Asn Ser Leu Asp Tyr Asn Glu
 145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
                180                 185                 190
Ala Asn His Tyr Glu Asp Tyr Gly Asp Tyr Trp Arg Gly Asp Tyr Glu
                195                 200                 205
Val Asn Gly Val Asp Gly Tyr Asp Tyr Ser Arg Gly Gln Leu Ile Glu
                210                 215                 220
Asp Val Glu His Thr Phe Glu Glu Ile Lys Pro Leu Tyr Glu His Leu
 225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
                260                 265                 270
Arg Phe Trp Thr Asn Leu Tyr Ser Leu Thr Val Pro Phe Gly Gln Lys
                275                 280                 285
Pro Asn Ile Asp Val Thr Asp Ala Met Val Asp Gln Ala Trp Asp Ala
 290                 295                 300
Gln Arg Ile Phe Lys Glu Ala Glu Lys Phe Phe Val Ser Val Gly Leu
 305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
                355                 360                 365
Phe Leu Thr Ala His His Glu Met Gly His Ile Gln Tyr Asp Met Ala
                370                 375                 380
Tyr Ala Ala Gln Pro Phe Leu Leu Arg Asn Gly Ala Asn Glu Gly Phe
 385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Gly
                435                 440                 445
```

```
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Phe Gln Phe Gln Glu Ala
        515                 520                 525
Leu Cys Gln Ala Ala Lys His Glu Gly Pro Leu His Lys Cys Asp Ile
    530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Gln Ser Ile Lys Val Arg Ile Ser Leu
    610                 615                 620
Lys Ser Ala Leu Gly Asp Arg Ala Tyr Glu Trp Asn Asp Asn Glu Met
625                 630                 635                 640
Tyr Leu Phe Arg Ser Ser Val Ala Tyr Ala Met Arg Gln Tyr Phe Leu
                645                 650                 655
Lys Val Lys Asn Gln Met Ile Leu Phe Gly Glu Glu Asp Val Arg Val
            660                 665                 670
Ala Asn Leu Lys Pro Arg Ile Ser Phe Asn Phe Phe Val Thr Ala Pro
        675                 680                 685
Lys Asn Val Ser Asp Ile Ile Pro Arg Thr Glu Val Glu Lys Ala Ile
    690                 695                 700
Arg Met Ser Arg Ser Arg Ile Asn Asp Ala Phe Arg Leu Asn Asp Asn
705                 710                 715                 720
Ser Leu Glu Phe Leu Gly Ile Gln Pro Thr Leu Gly Pro Pro Asn Gln
                725                 730                 735
Pro Pro Val Ser His His His His His His
            740                 745

<210> SEQ ID NO 47
<211> LENGTH: 879
<212> TYPE: PRT
<213> ORGANISM: Artificial Sequence
<220> FEATURE:
<223> OTHER INFORMATION: ACE2-microbody

<400> SEQUENCE: 47

Met Ser Ser Ser Ser Trp Leu Leu Leu Ser Leu Val Ala Val Thr Ala
1               5                   10                  15
Ala Gln Ser Thr Ile Glu Glu Gln Ala Lys Thr Phe Leu Asp Lys Phe
                20                  25                  30
Asn His Glu Ala Glu Asp Leu Phe Tyr Gln Ser Ser Leu Ala Ser Trp
            35                  40                  45
Asn Tyr Asn Thr Asn Ile Thr Glu Glu Asn Val Gln Asn Met Asn Asn
        50                  55                  60
```

```
Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480
```

-continued

```
Lys Arg Glu Ile Val Gly Val Val Glu Pro Val His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Glu Pro Lys Ser Cys Asp Lys Thr His Thr Cys Pro
            740                 745                 750

Pro Cys Gly Gly Gly Ser Ser Gly Gly Gly Ser Gly Gly Gln Pro Arg
        755                 760                 765

Glu Pro Gln Val Tyr Thr Leu Pro Pro Ser Arg Glu Glu Met Thr Lys
    770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys His His His His His His
865                 870                 875
```

<210> SEQ ID NO 48
<211> LENGTH: 879
<212> TYPE: PRT

<213> ORGANISM: Artificial Sequence
<220> FEATURE:
<223> OTHER INFORMATION: ACE2.H345A-microbody

<400

```
385                 390                 395                 400
His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
    610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Glu Pro Lys Ser Cys Asp Lys Thr His Thr Cys Pro
                740                 745                 750

Pro Cys Gly Gly Gly Ser Ser Gly Gly Gly Ser Gly Gly Gln Pro Arg
            755                 760                 765

Glu Pro Gln Val Tyr Thr Leu Pro Pro Ser Arg Glu Glu Met Thr Lys
    770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815
```

-continued

```
Thr Thr Pro Pro Val Leu Asp Ser Asp Gly Ser Phe Phe Leu Tyr Ser
            820              825              830

Lys Leu Thr Val Asp Lys Ser Arg Trp Gln Gln Gly Asn Val Phe Ser
            835              840              845

Cys Ser Val Met His Glu Ala Leu His Asn His Tyr Thr Gln Lys Ser
    850              855              860

Leu Ser Leu Ser Pro Gly Lys His His His His His His His His
865              870              875
```